United States Patent
Zhang et al.

(10) Patent No.: US 11,046,981 B2
(45) Date of Patent: Jun. 29, 2021

(54) HOST CELL MODIFIED TO PRODUCE LACTAMS

(71) Applicants: Jingwei Zhang, Fullerton, CA (US); Jay D. Keasling, Berkeley, CA (US)

(72) Inventors: Jingwei Zhang, Fullerton, CA (US); Jay D. Keasling, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/212,515

(22) Filed: Dec. 6, 2018

(65) Prior Publication Data
US 2019/0338321 A1  Nov. 7, 2019

Related U.S. Application Data

(63) Continuation of application No. PCT/US2017/036168, filed on Jun. 6, 2017.

(60) Provisional application No. 62/346,294, filed on Jun. 6, 2016.

(51) Int. Cl.
*C12P 13/02* (2006.01)
*C12N 9/10* (2006.01)
*C12N 15/52* (2006.01)

(52) U.S. Cl.
CPC ............ *C12P 13/02* (2013.01); *C12N 9/1048* (2013.01); *C12N 15/52* (2013.01)

(58) Field of Classification Search
None
See application file for complete search history.

(56) References Cited

U.S. PATENT DOCUMENTS

| | | | |
|---|---|---|---|
| 10,227,622 B2* | 3/2019 | Zhang | C12N 9/88 |
| 2004/0087654 A1 | 5/2004 | Box et al. | |
| 2008/0233623 A1 | 9/2008 | Chang et al. | |
| 2009/0081673 A1 | 3/2009 | Shen et al. | |

OTHER PUBLICATIONS

Zhang et al.,"Metabolic engineering of *Escherichia coli* for the biosynthesis of 2-pyrrolidine", Metabolic Engineering Communications 3: 1-7 (2016) Online Nov. 10, 2015. (Year: 2016).*
Stavila et al., Synthesis of lactams using enzyme-catalyzed aminolysis, Tetrahedron Letters 54: 370-372 (2013).
Zhang et al., Metabolic Engineering of *E. coli* for the biosynthesis of 2-pyrrolidone. Met Eng Comm 3:1-7 (2016).
Liu et al., Enzymatic production of 5-aminovalerate from L-lysine using L-lysine monooxygenase and 5-aminovaleramide amidohydrolase. Sci Rep 4:5657 (2014).
Park et al., Metabolic engineering of *Escherichia coli* for the production of 5-aminovalerate and glutarate as C5 platform chemicals. Metab Eng 16:42-47 (2013).
Park et al., High-level conversion of L-lysine into 5-aminovalerate that can be used for nylon 6,5 synthesis. Biotechnol J 9:1322-1328 (2014).
Ritz et al., Caprolactam. Ullmann's Encyclopedia of Industrial Chemistry. [[DOI: 10.1002/14356007.a05_031.pub2]], Oct. 15, 2011.
Kallifidas et al., The sigmaR regulon of Streptomyces coelicolor A32 reveals a key role in protein quality control during disulphide stress. Microbiology 156:1661-1672 (2010).
Turk et al., Metabolic engineering towards sustainable production of Nylon-6. ACS Synthetic Biology, ACS Synth. Biol, 5:65-73 (2015).
Hong et al., A Common Origin for Guanidinobutanoate Starter Units in Antifungal Natural Products. Angewandte Chemie 52:13096-13099 (2013).
McAlpine et al., Microbial Genomics as a Guide to Drug Discovery and Structural Elucidation: ECO-02301, a Novel Antifungal Agent, as an Example. J Nat Prod. 68: 493-496 (2005).
Zazopoulos et al., A genomics-guided approach for discovering and expressing cryptic metabolic pathways. Nat Biotechnol 21:187-190 (2003).
Zhang et al., A Three Enzyme Pathway for 2-Amino-3-hydroxycyclopent-2-enone Formation and Incorporation in Natural Product Biosynthesis. J Am Chem Soc 132:6402-6411 (2010).
Yuzawa et al., Construction of a part of a 3-hydroxypropionate cycle for heterologous polyketide biosynthesis in *Escherichia coli*. Biochemistry 51:9779-9781 (2012).
Baba et al., Construction of *Escherichia coli* K-12 in-frame, single-gene knockout mutants: the Keio collection. Molecular Systems Biology (2006).
Lee et al., BglBrick vectors and datasheets: A synthetic biology platform for gene expression. J Biol Eng 5:12 (2011).
Studier, Protein production by auto-induction in high-density shaking cultures. Protein Expression and Purification 41:207-234 (2005).
Zhang et al., Activation of the pacidamycin PacL adenylation domain by MbtH-like proteins. Biochemistry 49:9946-9947 (2010).
Bokinsky et al., HipA-Triggered Growth Arrest and β-Lactam Tolerance in *Escherichia coli* Are Mediated by RelA-Dependent ppGpp Synthesis. Journal of Bacteriology 195:3173-3182 (2013).
International Search Report and Written Opinion for PCT/US17/36168, dated Sep. 8, 2017.

* cited by examiner

*Primary Examiner* — Anand U Desai
(74) *Attorney, Agent, or Firm* — Robin C. Chiang; Lawrence Berkeley National Laboratory

(57) ABSTRACT

The present invention provides for a genetically modified host cell capable of producing a lactam comprising a 2-pyrrolidone synthase, or an enzymatically active fragment thereof, heterologous to the host cell.

17 Claims, 18 Drawing Sheets

Specification includes a Sequence Listing.

A.

B.

A.

E.

F.

I.

J.

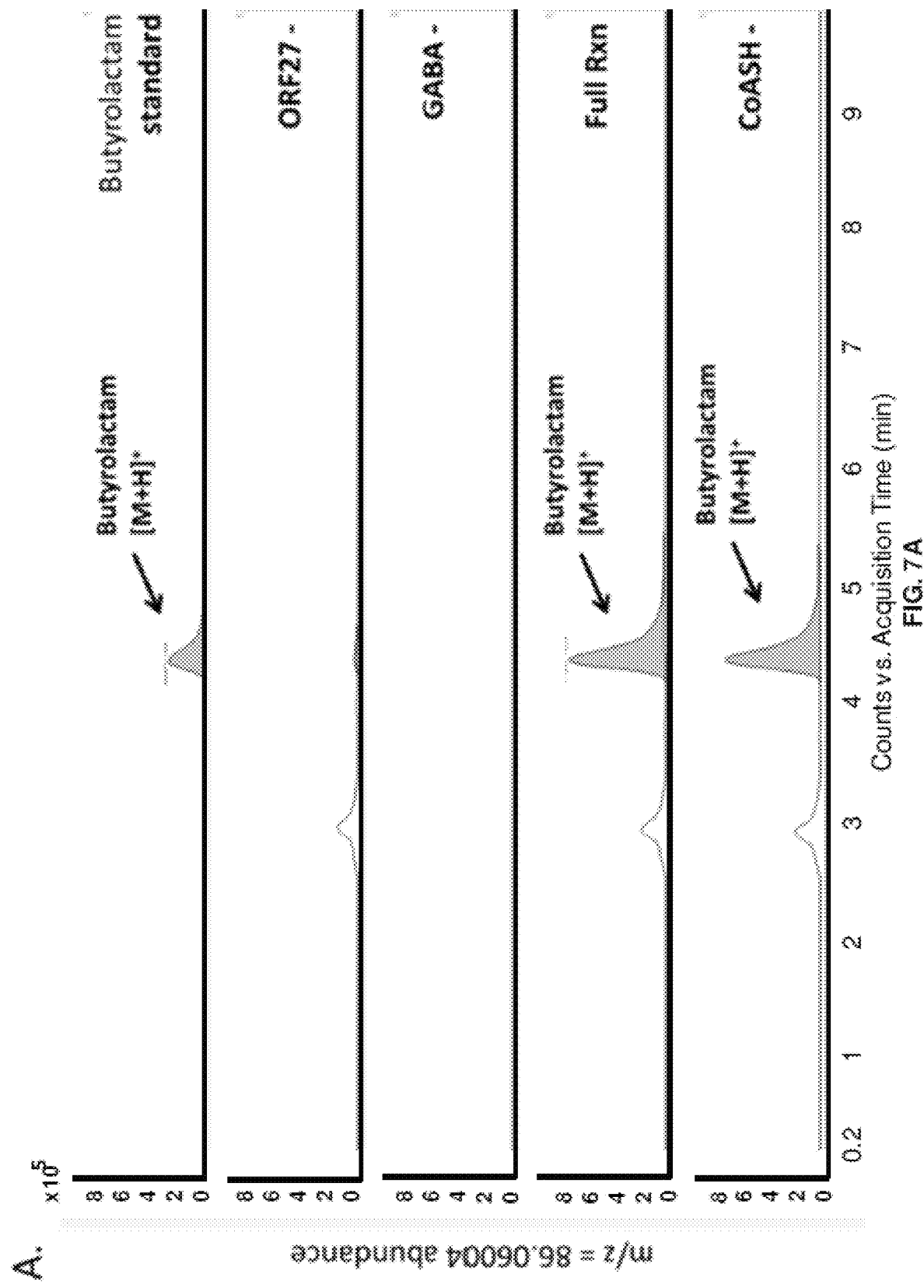

```
P. furiosus    VVIWWAMQFHELSVTQGLAEETHALCPEVEIVFEQK-PHLEDALKAAIPTGQGPDLFIWA  59
P. aerophilum  IRIWHALNPEEESVFRQIAAMYTQTHPNVQIVFENKAPDLQTRVLAAISTGEKFDLFIWA  60
E. coli        LVIWINGD-KGYDHLAEVGKHFEKDT-GIKVTVEHP-DKIEHPFQVAATGDGPDIIFWA  57
                 * *    *      **  *      *    *          * *    *** *****

P. furiosus    HDWIGKFAEAGLLEPIDEYVTEDLLNEFAPHAQHAMQYKGHYYALPFAAETVAIIYNKHN  119
P. aerophilum  HDWIGLMVEAGVLKPVDNEVADVLSRFGAPIP---PYKGHIYGLPFAAETVALICNKQH  116
E. coli        HDRFGGYAQSGLLAEITP--DKAFQDKLYPFTWDAVRYNGKLIAYPIAVEALSLIYNKDL  115
               **  *    **   *          *           * * *  * *** ***  *

P. furiosus    VQEPPKTFDEMKAIHKRYDPHNHRYGIAHPINAYFISAIAQAFHGTYFFDKT------EQ  174
P. aerophilum  VSQPPKTFADLLAIDKQFHKPP-QFYGIAYVVNPTFISAWIRDAGGYYFDDET-----EK  170
E. coli        LPNPPKTWESIPALDKELKAHS-KGAIMFHLQEPYFTWRLIAARDEHRAFKYENSGKYDIRD  174
                 *****     *    *         *          *     *    *

P. furiosus    PGLDKEETIEGFKFFFTEIWFTNAP-TGDHNTQQSIFLEGRAFHRHNGPWSINDVRKAGI  233
P. aerophilum  QKLTDPKSIRAGFTFFKSYINPYVGFNPTDKNTQVHLFLSGQAPCMVNGFWGIGAVIQRGI  230
E. coli        VGVDKAGAKAGLTFLVDLIKNEEMKADTDYSIAEAAPKKETAMTINGFWAWGNIDTGRV  234
                   *       *        *          **       *     * *     ***

P. furiosus    NFGVVFLPPIIKDGKETWPRFYGGVKLIYFAAGIENKDAAWEFAKWLTTSEEDIKTLALE  293
P. aerophilum  DVFYAPLPFVN----ATYIPKPYGGMKHFVT---ITASHEAIDFHKWFTTDPQVAKILKEG  285
E. coli        NYGVTVLPFFK----GQPSKFVGVLSAGINAASDHKEIAKEFLEMYLITDEGLEAVNKD  290
                   *   * *           *    * *        *    *   *     *

P. furiosus    DGYIPVLTRVLDEFEIKNDPVIPFGGAVQHAILMFKSPKMSRAVWDGVDKAIN-EILQDP  352
P. aerophilum  LGYVPVIKDVQ-------IQDPVVQGFYEAVKNIYLNPVSFKRQPYWGTVDLIIQNDIVSDG  340
E. coli        KPLGAVALKGY-EEELAKDFRIAATMENAQKGEIHPHTPQMCAFWKAVRTAVINAASGRQ  349
                  *        *    *      *   *                *   *       *

P. furiosus    Q--NADIEGILHKYQQ  366
P. aerophilum  RTIGLAVNDAVKDLI-  355
E. coli        T-------VDEAIKDAQT  360
                  *      *
```

FIG. 10

SEQUENCE LISTING

<160> NUMBER OF SEQ ID NOS: 24

<210> SEQ ID NO 1
<211> LENGTH: 470
<212> TYPE: PRT
<213> ORGANISM: Streptomyces aizunensis

<400> SEQUENCE: 1

```
Met Arg Pro Met Thr Ala Lys Ile Phe Ala Val Asp Ser Val Arg Pro
1               5                   10                  15

Ile Asp Glu Phe Glu Gln Asp Ala Leu Arg Val Ala Asp Val Ile Arg
            20                  25                  30

Glu Arg Gly Val Cys Leu Gly Asp Arg Val Met Leu Lys Ala Gly Asn
        35                  40                  45

Ser Ala Ser Tyr Val Cys Val Leu Tyr Ala Leu Met His Ile Gly Ala
    50                  55                  60

Ser Ile Val Leu Val Asp Gln Gln Glu His Lys Glu Thr Arg Arg
65                  70                  75                  80

Ile Ala Leu Arg Thr Gly Val Lys Val Thr Phe Val Asp Asp Glu Thr
                85                  90                  95

Pro Ile Asp Gln Asp Ala Asp Pro Ile His Leu Tyr Glu Leu Met Val
            100                 105                 110

Ala Thr Gln Asn Arg Pro Pro Met Asp Ser Ala Leu Ser Phe Asp Ala
        115                 120                 125

Trp Gly Glu Leu Ser Asp Gly Leu Ile Met Trp Thr Ser Gly Ser Thr
    130                 135                 140

Gly Ser Pro Lys Gly Val Val Lys Ser Gly Gly Lys Phe Leu Ala Asn
145                 150                 155                 160

Leu Arg Arg Asn Ala His Gln Val Gly His Arg Pro Asp Asp Val Leu
                165                 170                 175

Met Pro Leu Leu Pro Phe Ala His Gln Tyr Gly Leu Ser Met Val Leu
            180                 185                 190

Ile Ala Trp Leu Thr Arg Cys Ser Leu Val Ile Ala Pro Tyr Arg Arg
        195                 200                 205

Leu Asp Arg Ala Leu Arg Met Ala Arg Asp Ser Gly Thr Thr Val Ile
    210                 215                 220

Asp Ala Thr Pro Ser Ser Tyr Arg Ser Ile Leu Gly Leu Val Thr Arg
225                 230                 235                 240

Lys Pro Ala Leu Arg Ala His Leu Ala Gly Thr Arg Met Phe Cys Val
                245                 250                 255

Gly Ala Ala Pro Leu Asp Ala Pro Leu Val Glu Ser Tyr Val Gln Glu
            260                 265                 270
```

```
Phe Gly Leu Pro Leu Leu Asp Ser Tyr Gly Ser Thr Glu Leu Asn Asn
            275                 280                 285

Ile Ala Phe Ala Thr Leu Asp Asn Pro Val Ser Cys Gly Arg Ala Met
290                 295                 300

Glu Gly Ile Gly Leu Arg Ile Val Asp Glu Asp Gly Arg Val Ala
305                 310                 315                 320

Ala Gly Gln Pro Gly Glu Ile Glu Val Asp Thr Pro Asp Ala Leu Glu
                325                 330                 335

Gly Gln Ile Ala Glu Asp Gly Ser Ile Ile Pro Ala Pro Thr Gly Trp
            340                 345                 350

Gln Arg Thr Gly Asp Leu Gly His Leu Asp Ala Asp Gly Asn Leu Tyr
        355                 360                 365

Val Leu Gly Arg Lys Phe Ala Val His Arg Met Gly Tyr Thr Leu Tyr
    370                 375                 380

Pro Glu Leu Ile Glu Arg Lys Val Ala Ala Glu Gly Cys Pro Thr Arg
385                 390                 395                 400

Ile Val Pro Leu Pro Asp Glu Leu Arg Gly Ser Gln Leu Val Phe Phe
                405                 410                 415

Val Glu Asp Asp Glu Gln Arg Asp Ala Gly Tyr Trp Arg Glu Arg Leu
            420                 425                 430

Cys Gly Leu Leu Pro Ala Phe Glu Gln Pro Asn Lys Val Val Val Leu
        435                 440                 445

Glu Gln Phe Pro Leu Asn Arg Asn Gly Lys Pro Asp Lys Lys Glu Leu
    450                 455                 460

Thr Arg Met Ala Ala Glu
465                 470

<210> SEQ ID NO 2
<211> LENGTH: 366
<212> TYPE: PRT
<213> ORGANISM: Pyrococcus furiosus

<400> SEQUENCE: 2

Val Val Ile Trp His Ala Met Gln Pro Asn Glu Leu Glu Val Phe Gln
1               5                   10                  15

Ser Leu Ala Glu Glu Tyr Met Ala Leu Cys Pro Glu Val Glu Ile Val
            20                  25                  30

Phe Glu Gln Lys Pro Asn Leu Glu Asp Ala Leu Lys Ala Ala Ile Pro
        35                  40                  45

Thr Gly Gln Gly Pro Asp Leu Phe Ile Trp Ala His Asp Trp Ile Gly
    50                  55                  60

Lys Phe Ala Glu Ala Gly Leu Leu Glu Pro Ile Asp Glu Tyr Val Thr
65                  70                  75                  80

Glu Asp Leu Leu Asn Glu Phe Ala Pro Met Ala Gln Asp Ala Met Gln
                85                  90                  95

Tyr Lys Gly His Tyr Tyr Ala Leu Pro Phe Ala Glu Thr Val Ala
            100                 105                 110

Ile Ile Tyr Asn Lys Glu Met Val Ser Glu Pro Pro Lys Thr Phe Asp
        115                 120                 125

Glu Met Lys Ala Ile Met Glu Lys Tyr Tyr Asp Pro Ala Asn Glu Lys
    130                 135                 140

Tyr Gly Ile Ala Trp Pro Ile Asn Ala Tyr Phe Ile Ser Ala Ile Ala
145                 150                 155                 160

Gln Ala Phe Gly Gly Tyr Tyr Phe Asp Asp Lys Thr Glu Gln Pro Gly
                165                 170                 175
```

```
Leu Asp Lys Pro Glu Thr Ile Glu Gly Phe Lys Phe Phe Thr Glu
            180                 185                 190

Ile Trp Pro Tyr Met Ala Pro Thr Gly Asp Tyr Asn Thr Gln Gln Ser
        195                 200                 205

Ile Phe Leu Glu Gly Arg Ala Pro Met Met Val Asn Gly Pro Trp Ser
    210                 215                 220

Ile Asn Asp Val Lys Lys Ala Gly Ile Asn Phe Gly Val Val Pro Leu
225                 230                 235                 240

Pro Pro Ile Ile Lys Asp Gly Lys Glu Tyr Trp Pro Arg Pro Tyr Gly
                245                 250                 255

Gly Val Lys Leu Ile Tyr Phe Ala Ala Gly Ile Lys Asn Lys Asp Ala
            260                 265                 270

Ala Trp Lys Phe Ala Lys Trp Leu Thr Thr Ser Glu Glu Ser Ile Lys
        275                 280                 285

Thr Leu Ala Leu Glu Leu Gly Tyr Ile Pro Val Leu Thr Lys Val Leu
    290                 295                 300

Asp Asp Pro Glu Ile Lys Asn Asp Pro Val Ile Tyr Gly Phe Gly Gln
305                 310                 315                 320

Ala Val Gln His Ala Tyr Leu Met Pro Lys Ser Pro Lys Met Ser Ala
                325                 330                 335

Val Trp Gly Gly Val Asp Gly Ala Ile Asn Glu Ile Leu Gln Asp Pro
            340                 345                 350

Gln Asn Ala Asp Ile Glu Gly Ile Leu Lys Lys Tyr Gln Gln
        355                 360                 365

<210> SEQ ID NO 3
<211> LENGTH: 355
<212> TYPE: PRT
<213> ORGANISM: Pyrobaculum aerophilum

<400> SEQUENCE: 3

Ile Arg Ile Trp His Ala Leu Asn Pro Glu Glu Ser Val Phe Lys
1               5                   10                  15

Gln Ile Ala Ala Met Tyr Thr Gln Thr His Pro Asn Val Gln Ile Val
            20                  25                  30

Phe Glu Asn Lys Ala Pro Asp Leu Gln Thr Ala Val Leu Ala Ala Ile
        35                  40                  45

Ser Thr Gly Glu Lys Phe Asp Leu Phe Ile Trp Ala His Asp Trp Ile
    50                  55                  60

Gly Leu Met Val Glu Ala Gly Val Leu Lys Pro Val Asp Asn Glu Val
65                  70                  75                  80

Ala Asp Val Leu Ser Arg Phe Ser Ala Pro Ile Pro Gln Tyr Lys Gly
                85                  90                  95

His Ile Tyr Gly Leu Pro Phe Ala Ala Glu Thr Val Ala Leu Ile Cys
            100                 105                 110

Asn Lys Gln Met Val Ser Gln Pro Pro Lys Thr Phe Ala Asp Leu Leu
        115                 120                 125

Ala Ile Met Arg Gln Phe Asn Lys Pro Pro Gln Thr Tyr Gly Ile Ala
    130                 135                 140

Tyr Val Val Asn Pro Tyr Phe Ile Ser Ala Trp Ile His Gly Ala Gly
145                 150                 155                 160

Gly Tyr Tyr Phe Asp Asp Glu Thr Glu Lys Gln Gly Leu Thr Asp Pro
                165                 170                 175

Lys Ser Ile Ala Gly Phe Thr Phe Phe Lys Ser Tyr Ile Met Pro Tyr
            180                 185                 190
```

-continued

```
Val Gly Pro Asn Pro Thr Asp Tyr Asn Thr Gln Val Asn Leu Phe Leu
        195                 200                 205

Ser Gly Gln Ala Pro Cys Met Val Asn Gly Pro Trp Ser Ile Gly Ala
210                 215                 220

Val Lys Gln Arg Gly Ile Asp Val Phe Val Ala Pro Leu Pro Pro Val
225                 230                 235                 240

Asn Ala Thr Tyr Ile Pro Lys Pro Tyr Gly Met Lys Met Phe Tyr
                245                 250                 255

Val Thr Ile Tyr Ala Ser Lys Glu Ala Ile Asp Phe Met Lys Trp Phe
            260                 265                 270

Thr Thr Asp Pro Gln Val Ala Lys Ile Leu Met Asp Gln Leu Gly Tyr
            275                 280                 285

Val Pro Val Ile Lys Asp Val Gln Ile Gln Asp Pro Val Val Gln Gly
        290                 295                 300

Phe Tyr Glu Ala Val Lys Asn Ile Tyr Leu Met Pro Val Ser Pro Lys
305                 310                 315                 320

Met Gln Pro Val Trp Gly Thr Val Asp Leu Ile Gln Asn Ser Ile
                325                 330                 335

Val Ser Asp Gln Lys Thr Ile Ser Leu Ala Val Asn Asp Ala Val Lys
            340                 345                 350

Asp Leu Leu
        355

<210> SEQ ID NO 4
<211> LENGTH: 360
<212> TYPE: PRT
<213> ORGANISM: Escherichia coli

<400> SEQUENCE: 4

Leu Val Ile Trp Ile Asn Gly Asp Lys Gly Tyr Asn Gly Leu Ala Glu
1               5                   10                  15

Val Gly Lys Lys Phe Glu Lys Asp Thr Gly Ile Lys Val Thr Val Glu
                20                  25                  30

His Pro Asp Lys Leu Glu Glu Lys Phe Pro Gln Val Ala Ala Thr Gly
            35                  40                  45

Asp Gly Pro Asp Ile Ile Phe Trp Ala His Asp Arg Phe Gly Gly Tyr
        50                  55                  60

Ala Gln Ser Gly Leu Leu Ala Glu Ile Thr Pro Asp Lys Ala Phe Gln
65                  70                  75                  80

Asp Lys Leu Tyr Pro Phe Thr Trp Asp Ala Val Arg Tyr Asn Gly Lys
                85                  90                  95

Leu Ile Ala Tyr Pro Ile Ala Val Glu Ala Leu Ser Leu Ile Tyr Asn
            100                 105                 110

Lys Asp Leu Leu Pro Asn Pro Pro Lys Thr Trp Glu Glu Ile Pro Ala
        115                 120                 125

Leu Asp Lys Glu Leu Lys Ala Lys Gly Lys Ser Ala Leu Met Phe Asn
130                 135                 140

Leu Gln Glu Pro Tyr Phe Thr Trp Pro Leu Ile Ala Ala Asp Gly Gly
145                 150                 155                 160

Tyr Ala Phe Lys Tyr Glu Asn Gly Lys Tyr Asp Ile Lys Asp Val Gly
                165                 170                 175

Val Asp Asn Ala Gly Ala Lys Ala Gly Leu Thr Phe Leu Val Asp Leu
            180                 185                 190

Ile Lys Asn Lys His Met Asn Ala Asp Thr Asp Tyr Ser Ile Ala Glu
        195                 200                 205
```

```
Ala Ala Phe Asn Lys Gly Glu Thr Ala Met Thr Ile Asn Gly Pro Trp
210                 215                 220

Ala Trp Ser Asn Ile Asp Thr Ser Lys Val Asn Tyr Gly Val Thr Val
225                 230                 235                 240

Leu Pro Thr Phe Lys Gly Gln Pro Ser Lys Pro Phe Val Gly Val Leu
                245                 250                 255

Ser Ala Gly Ile Asn Ala Ala Ser Pro Asn Lys Glu Leu Ala Lys Glu
                260                 265                 270

Phe Leu Glu Asn Tyr Leu Leu Thr Asp Glu Gly Leu Glu Ala Val Asn
                275                 280                 285

Lys Asp Lys Pro Leu Gly Ala Val Ala Leu Lys Ser Tyr Glu Glu Glu
290                 295                 300

Leu Ala Lys Asp Pro Arg Ile Ala Ala Thr Met Glu Asn Ala Gln Lys
305                 310                 315                 320

Gly Glu Ile Met Pro Asn Ile Pro Gln Met Ser Ala Phe Trp Tyr Ala
                325                 330                 335

Val Arg Thr Ala Val Ile Asn Ala Ala Ser Gly Arg Gln Thr Val Asp
                340                 345                 350

Glu Ala Leu Lys Asp Ala Gln Thr
                355                 360

<210> SEQ ID NO 5
<211> LENGTH: 343
<212> TYPE: PRT
<213> ORGANISM: Methanococcus aeolicus

<400> SEQUENCE: 5

Met Lys Ile Pro Lys Ile Cys Val Ile Glu Gly Asp Gly Ile Gly Lys
1               5                   10                  15

Glu Val Ile Pro Glu Thr Val Arg Ile Leu Lys Glu Ile Gly Asp Phe
                20                  25                  30

Glu Phe Ile Tyr Glu His Ala Gly Tyr Glu Cys Phe Lys Arg Cys Gly
            35                  40                  45

Asp Ala Ile Pro Glu Lys Thr Leu Lys Thr Ala Lys Glu Cys Asp Ala
50                  55                  60

Ile Leu Phe Gly Ala Val Ser Thr Pro Lys Leu Asp Glu Thr Glu Arg
65                  70                  75                  80

Lys Pro Tyr Lys Ser Pro Ile Leu Thr Leu Arg Lys Glu Leu Asp Leu
                85                  90                  95

Tyr Ala Asn Val Arg Pro Ile His Lys Leu Asp Asn Ser Asp Ser Ser
                100                 105                 110

Asn Asn Ile Asp Phe Ile Ile Arg Glu Asn Thr Glu Gly Leu Tyr
                115                 120                 125

Ser Gly Val Glu Tyr Tyr Asp Glu Glu Lys Glu Leu Ala Ile Ser Glu
                130                 135                 140

Arg His Ile Ser Lys Lys Gly Ser Lys Arg Ile Ile Lys Phe Ala Phe
145                 150                 155                 160

Glu Tyr Ala Val Lys His His Arg Lys Lys Val Ser Cys Ile His Lys
                165                 170                 175

Ser Asn Ile Leu Arg Ile Thr Asp Gly Leu Phe Leu Asn Ile Phe Asn
                180                 185                 190

Glu Phe Lys Glu Lys Tyr Lys Asn Glu Tyr Asn Ile Glu Gly Asn Asp
                195                 200                 205

Tyr Leu Val Asp Ala Thr Ala Met Tyr Ile Leu Lys Ser Pro Gln Met
210                 215                 220
```

Phe Asp Val Ile Val Thr Thr Asn Leu Phe Gly Asp Ile Leu Ser Asp
225                 230                 235                 240

Glu Ala Ser Gly Leu Leu Gly Gly Leu Gly Leu Ala Pro Ser Ala Asn
            245                 250                 255

Ile Gly Asp Asn Tyr Gly Leu Phe Glu Pro Val His Gly Ser Ala Pro
            260                 265                 270

Asp Ile Ala Gly Lys Gly Val Ala Asn Pro Ile Ala Ala Val Leu Ser
            275                 280                 285

Ala Ser Met Met Leu Tyr Tyr Leu Asp Met Lys Glu Lys Ser Arg Leu
            290                 295                 300

Leu Lys Asp Ala Val Lys Gln Val Leu Ala His Lys Asp Ile Thr Pro
305                 310                 315                 320

Asp Leu Gly Gly Asn Leu Lys Thr Lys Glu Val Ser Asp Lys Ile Ile
            325                 330                 335

Glu Glu Leu Arg Lys Ile Ser
            340

<210> SEQ ID NO 6
<211> LENGTH: 898
<212> TYPE: DNA
<213> ORGANISM: Pseudomonas putida

<400> SEQUENCE: 6
cccgatcgcc ctggcggatt gaggatcttt taagaaggag atatacatat gcgcatcgct     60
ctgtaccagg gcgcacccaa gccactggat gtgcccggca acctgcaacg gctgcgccac    120
caggcgcagt tggcagccga ccgcggcgca cagttgctgg tgtgcccgga gatgttcctg    180
tccggctaca acatcggcct ggcccaggtc gagcgcctgg ccgaggccgc cgatggcccg    240
gcagccatga cggtggtgga gattgcccag gcgcaccgta tcgccattgt ctatggctac    300
ccggagcgcg gcgatgacgg ggcgatctac aacagcgtgc agctgatcga tgcgcatggc    360
cgcagcctga gcaattaccg caagacccac ctgttcggtg aactggaccg ctcgatgttc    420
agccctggtg cggaccactt cccggtggtg aactggaag gctggaaggt tggcctgctg    480
atctgctacg acatcgagtt cccggagaac gcccgacgcc tggcgctgga cggcgccgag    540
ctgatcctgg tgccgacggc gaacatgacg ccgtacgact ttacctgcca ggtgaccgtg    600
agggcacggg cgcaggaaaa ccagtgctac ctggtatatg ccaactactg cggcgcggaa    660
gacgagatcg agtattgcgg gcagagcagc atcatcggcc cggatggcag cttgctggcc    720
atggccgggc gggatgagtg ccagttgttg cagagctcg agcatgagcg ggtggtgcag    780
gggcgcaggg cgtttcccta cctgaccgat ttgcgccagg agctgcacct gcgtaaaggc    840
tgaggatcca aactcgagta aggatctcca ggcatcaaat aaaacgaaag gctcagtc     898

<210> SEQ ID NO 7
<211> LENGTH: 6146
<212> TYPE: DNA
<213> ORGANISM: Pseudomonas putida

<400> SEQUENCE: 7
gacgtcctca ctgcccgctt tccagtcggg aaacctgtcg tgccagctgc attaatgaat     60
cggccaacgc gcggggagag gcggtttgcg tattgggcgc cagggtggtt tttcttttca    120
ccagtgagac gggcaacagc tgattgcccct tcaccgcctg gccctgagag agttgcagca    180
agcggtccac gctggtttgc cccagcaggc gaaaatcctg tttgatgtg gttaacggcg    240 ggatataaca tgagctgtct tcggtatcgt cgtatcccac taccgagatg tccgcaccaa    300

```
cgcgcagccc ggactcggta atggcgcgca ttgcgcccag cgccatctga tcgttggcaa      360
ccagcatcgc agtgggaacg atgccctcat tcagcatttg catggtttgt tgaaaaccgg      420
acatggcact ccagtcgcct tcccgttccg ctatcggctg aatttgattg cgagtgagat      480
atttatgcca gccagccaga cgcagacgcg ccgagacaga acttaatggg cccgctaaca      540
gcgcgatttg ctggtgaccc aatgcgacca gatgctccac gcccagtcgc gtaccgtctt      600
catgggagaa ataatactg ttgatgggtg tctggtcaga gacatcaaga aataacgccg       660
gaacattagt gcaggcagct tccacagcaa tggcatcctg gtcatccagc ggatagttaa      720
tgatcagccc actgacgcgt tgcgcgagaa gattgtgcac cgccgcttta caggcttcga      780
cgccgcttcg ttctaccatc gacaccacca cgctggcacc cagttgatcg gcgcgagatt      840
taatcgccgc gacaatttgc gacggcgcgt gcagggccag actggaggtg gcaacgccaa      900
tcagcaacga ctgtttgccc gccagttgtt gtgccacgcg gttgggaatg taattcagct      960
ccgccatcgc cgcttccact ttttcccgcg ttttcgcaga aacgtggctg gcctggttca     1020
ccacgcggga aacggtctga taagagacac cggcatactc tgcgacatcg tataacgtta     1080
ctggtttcac attcaccacc ctgaattgac tctcttccgg gcgctatcat gccataccgc     1140
gaaaggtttt cgccattcg atggtgtccg ggatctcgac gctctccctt atgcgactcc      1200
tgcattagga agcagcccag tagtaggttg aggccgttga gcaccgccgc cgcaaggaat     1260
ggtgcatgca aggagatggc gcccaacagt cccccggcca cggggcctgc caccataccc     1320
acgccgaaac aagcgctcat gagcccgaag tggcgagccc gatcttcccc atcggtgatg     1380
tcggcgatat aggcgccagc aaccgcacct gtggcgccgg tgatgccggc cacgatgcgt     1440
ccggcgtaga ggatcgagat cgatctcgat cccgcgaaat taatacgact cactataggg     1500
gaattgtgag cggataacaa tttcagaatt caaaagatct tttaagaagg agatatacat     1560
atgaacaaga gaaccgcca ccccgccgac ggcaagaagc cgatcaccat tttcggcccg      1620 gacttcccctt ttgctttcga cgactggctg aacacccgg caggcctggg cagcattccg     1680
gctgagcgcc atggggaaga ggtggccatt gtcggtgccg gtatcgccgg cctggtagcg     1740
gcctacgagc tgatgaagct gggcctcaag ccggtggtgt acgaggcttc caagctgggc     1800
ggccggctgc gctcgcaagc cttcaatggc actgacggga tcgttgccga gctggtggc      1860 atgcgcttcc cggtgtcgtc caccgccttc taccactacg tcgacaagct gggcctggag     1920
accaagccct tccccaaccc gctgaccccg gcttcgggca gcacggtgat cgacctggaa     1980
ggccagacct actacgccga gaagcccacc gacctgccgc aactgttttca tgaggtagcc     2040 gacgcttggg ccgatgctct ggagagcggt gcgcagttcg ccgatatcca gcaggccatc     2100
cgcgaccgtg atgtaccgcg cctgaaggaa ctctggaaca agctggtgcc actgtgggac     2160
gaccgcacct tctacgactt cgtcgccacc tcgcgctctt ttgccaagct gagcttccag     2220
caccgcgaag tgttcggcca ggtcggttttc ggcaccggcg gttgggactc ggacttcccc     2280
aactcgatgc tggaaatctt ccgcgtggtg atgaccaact gcgacgacca ccagcacctg     2340
gtggtcgggg gcgtggaaca agtgccacaa ggcatctggc gcgacgtacc ggaacgctgc     2400
gtgcattggc cagagggcac cagcctgagc acgctgcatg gcggcgcacc gcgtaccggg     2460
gtcaagcgca ttgcccgcgc cgccgatggc cgcctggcgg tcaccgacaa ctggggcgat     2520
acccgccact acagcgcagt actcgccacc tgccagacct ggttgctgac caccagatc     2580 gactgcgagg aatcgctgtt ctcgcaaaag atgtggatgg ccctgaccg tacccgctac     2640 atgcagtcgt cgaaaacctt cgtcatggtc gaccgcccgt tctggaagga caaggacccg     2700
```

```
gaaaccggcc gtgacctgct gagcatgacc ctcaccgacc gcctcacccg cggcacttac    2760
ctgttcgaca acggcaacga caagcccggg gtgatctgcc tgtcgtactc gtggatgagc    2820
gacgcgctga agatgctgcc gcacccggtg aaaagcgcg tacaactggc cctggatgcg    2880
ctgaagaaga tctacccgaa gaccgatatc gccgggcaca tcatcggcga cccgatcacg    2940
gtttcctggg aggccgaccc gtacttcctc ggcgccttca aaggcgcgct tccgggccat    3000
taccgctaca accagcgcat gtacgcgcac ttcatgcagc aggacatgcc ggcggagcag    3060
cgcggtatct tcattgccgg tgacgacgtg tcatggaccc ccgcctgggt tgaaggcgcg    3120
gtgcagacgt cgctgaatgc ggtgtggggt atcatgaacc actttggtgg ccacacccac    3180
cccgacaacc ccggcccggg cgatgtgttc aacgaaatcg gcccgatcgc cctggcggat    3240
tgaggatctt ttaagaagga gatatacata tgcgcatcgc tctgtaccag ggcgcaccca    3300
agccactgga tgtgcccggc aacctgcaac ggctgcgcca ccaggcgcag ttggcagccg    3360
accgcggcgc acagttgctg gtgtgcccgg agatgttcct gtccggctac aacatcggcc    3420
tggcccaggt cgagcgcctg gccgaggccg ccgatgcccc ggcagccatg acggtggtgg    3480
agattgccca ggcgcaccgt atcgccattg tctatggcta cccggagcgc ggcgatgacg    3540
gggcgatcta caacagcgtg cagctgatcg atgcgcatgg ccgcagcctg agcaattacc    3600
gcaagaccca cctgttcggt gaactggacc gctcgatgtt cagccctggt gcggaccact    3660
tcccggtggt ggaactggaa ggctggaagg ttggcctgct gatctgctac gacatcgagt    3720
tcccggagaa cgcccgacgc ctggcgctgg acggcgccga gctgatcctg gtgccgacgg    3780
cgaacatgac gccgtacgac tttacctgcc aggtgaccgt gagggcacgg gcgcaggaaa    3840
accagtgcta cctggtatat gccaactact gcggcgcgga agacgagatc gagtattgcg    3900
ggcagagcag catcatcggc ccggatggca gcttgctggc catggccggg cgggatgagt    3960
gccagttgtt ggcagagctc gagcatgagc gggtggtgca ggggcgcagg gcgtttccct    4020
acctgaccga tttgcgccag gagctgcacc tgcgtaaagg ctgaggatcc aaactcgagt    4080
aaggatctcc aggcatcaaa taaaacgaaa ggctcagtcg aaagactggg cctttcgttt    4140
tatctgttgt ttgtcggtga acgctctcta ctagagtcac actggctcac cttcgggtgg    4200
gcctttctgc gtttatacct agggatatat tccgcttcct cgctcactga ctcgctacgc    4260
tcggtcgttc gactgcggcg agcggaaatg gcttacgaac ggggcggaga tttcctggaa    4320
gatgccagga agatacttaa cagggaagtg agagggccgc ggcaaagccg ttttttccata    4380 ggctccgccc ccctgacaag catcacgaaa tctgacgctc aaatcagtgg tggcgaaacc    4440
cgacaggact ataaagatac caggcgtttc ccctggcgg ctccctcgtg cgctctcctg    4500
ttcctgcctt tcggtttacc ggtgtcattc cgctgttatg gccgcgtttg tctcattcca    4560
cgcctgacac tcagttccgg gtaggcagtt cgctccaagc tggactgtat gcacgaaccc    4620
cccgttcagt ccgaccgctg cgccttatcc ggtaactatc gtcttgagtc aacccggaa    4680 agacatgcaa aagcaccact ggcagcagcc actggtaatt gatttagagg agttagtctt    4740
gaagtcatgc gccggttaag gctaaactga aggacaagt tttggtgact gcgctcctcc    4800
aagccagtta cctcggttca aagagttggt agctcagaga accttcgaaa aaccgccctg    4860
caaggcggtt ttttcgtttt cagagcaaga gattacgcgc agaccaaaac gatctcaaga    4920
agatcatctt attaatcaga taaaatattt ctagatttca gtgcaattta tctcttcaaa    4980
tgtagcacct gaagtcagcc ccatacgata taagttgtta ctagtgcttg gattctcacc    5040
aataaaaaac gcccggcggc aaccgagcgt tctgaacaaa tccagatgga gttctgaggt    5100
```

```
cattactgga tctatcaaca ggagtccaag cgagctcgta aacttggtct gacagttacc      5160
aatgcttaat cagtgaggca cctatctcag cgatctgtct atttcgttca tccatagttg      5220
cctgactccc cgtcgtgtag ataactacga tacgggaggg cttaccatct ggccccagtg      5280
ctgcaatgat accgcgagac ccacgctcac cggctccaga tttatcagca ataaaccagc      5340
cagccggaag ggccgagcgc agaagtggtc ctgcaacttt atccgcctcc atccagtcta      5400
ttaattgttg ccgggaagct agagtaagta gttcgccagt taatagtttg cgcaacgttg      5460
ttgccattgc tacaggcatc gtggtgtcac gctcgtcgtt tggtatggct tcattcagct      5520
ccggttccca acgatcaagg cgagttacat gatcccccat gttgtgcaaa aaagcggtta      5580
gctccttcgg tcctccgatc gttgtcagaa gtaagttggc cgcagtgtta tcactcatgg      5640
ttatggcagc actgcataat tctcttactg tcatgccatc cgtaagatgc ttttctgtga      5700
ctggtgagta ctcaaccaag tcattctgag aatagtgtat gcggcgaccg agttgctctt      5760
gcccggcgtc aatacgggat aataccgcgc cacatagcag aactttaaaa gtgctcatca      5820
ttggaaaacg ttcttcgggg cgaaaactct caaggatctt accgctgttg agatccagtt      5880
cgatgtaacc cactcgtgca cccaactgat cttcagcatc ttttactttc accagcgttt      5940
ctgggtgagc aaaaacagga aggcaaaatg ccgcaaaaaa gggaataagg gcgacacgga      6000
aatgttgaat actcatactc ttcctttttc aatattattg aagcatttat cagggttatt      6060
gtctcatgag cggatacata tttgaatgta tttagaaaaa taaacaaata ggggttccgc      6120
gcacatttcc ccgaaaagtg ccacct                                           6146

<210> SEQ ID NO 8
<211> LENGTH: 7856
<212> TYPE: DNA
<213> ORGANISM: Streptomyces aizunensis

<400> SEQUENCE: 8
tggcgaatgg gacgcgccct gtagcggcgc attaagcgcg gcgggtgtgg tggttacgcg        60
cagcgtgacc gctacacttg ccagcgccct agcgcccgct cctttcgctt tcttcccttc       120
cttcctcgcc acgttcgccg gctttccccg tcaagctcta aatcggggc tccctttagg        180 gttccgattt agtgctttac ggcacctcga ccccaaaaaa cttgattagg gtgatggttc       240
acgtagtggg ccatcgccct gatagacggt ttttcgccct ttgacgttgg agtccacgtt       300
ctttaatagt ggactcttgt tccaaactgg aacaacactc aaccctatct cggtctattc       360
ttttgattta agggatttt gccgatttc ggcctattgg ttaaaaaatg agctgattta         420
acaaaaattt aacgcgaatt ttaacaaaat attaacgttt acaatttcag gtggcacttt       480
tcggggaaat gtgcgcggaa cccctatttg tttattttc taaatacatt caaatatgta       540
tccgctcatg aattaattct tagaaaaact catcgagcat caaatgaaac tgcaatttat       600
tcatatcagg attatcaata ccatatttt gaaaagccg tttctgtaat gaaggagaaa        660
actcaccgag gcagttccat aggatggcaa gatcctggta tcggtctgcg attccgactc      720
gtccaacatc aatacaacct attaatttcc cctcgtcaaa ataaggtta tcaagtgaga       780 aatcaccatg agtgacgact gaatccggtg agaatggcaa aagtttatgc atttctttcc     840
agacttgttc aacaggccag ccattacgct cgtcatcaaa atcactcgca tcaaccaaac      900
cgttattcat tcgtgattgc gcctgagcga gacgaaatac gcgatcgctg ttaaaaggac     960
aattacaaac aggaatcgaa tgcaaccggc gcaggaacac tgccagcgca tcaacaatat    1020
tttcacctga atcaggatat tcttctaata cctggaatgc tgttttcccg gggatcgcag    1080
```

-continued

```
tggtgagtaa ccatgcatca tcaggagtac ggataaaatg cttgatggtc ggaagaggca       1140
taaattccgt cagccagttt agtctgacca tctcatctgt aacatcattg caacgctac        1200 ctttgccatg tttcagaaac aactctggcg catcgggctt cccatacaat cgatagattg      1260
tcgcacctga ttgcccgaca ttatcgcgag cccatttata cccatataaa tcagcatcca     1320
tgttggaatt taatcgcggc ctagagcaag acgtttcccg ttgaatatgg ctcataacac      1380
cccttgtatt actgtttatg taagcagaca gttttattgt tcatgaccaa aatcccttaa    1440
cgtgagtttt cgttccactg agcgtcagac cccgtagaaa agatcaaagg atcttcttga       1500
gatccttttt ttctgcgcgt aatctgctgc ttgcaaacaa aaaaaccacc gctaccagcg       1560
gtggtttgtt tgccggatca agagctacca actcttttc cgaaggtaac tggcttcagc        1620
agagcgcaga taccaaatac tgtccttcta gtgtagccgt agttaggcca ccacttcaag      1680
aactctgtag caccgcctac atacctcgct ctgctaatcc tgttaccagt ggctgctgcc       1740
agtggcgata gtcgtgtct taccgggttg gactcaagac gatagttacc ggataaggcg       1800
cagcggtcgg gctgaacggg gggttcgtgc acacagccca gcttggagcg aacgacctac     1860
accgaactga gatacctaca gcgtgagcta tgagaaagcg ccacgcttcc gaagggaga      1920 aaggcggaca ggtatccggt aagcggcagg gtcggaacag gagagcgcac gagggagctt      1980 ccaggggaa acgcctggta tctttatagt cctgtcgggt ttcgccacct ctgacttgag         2040
cgtcgatttt tgtgatgctc gtcagggggg cggagcctat ggaaaaacgc cagcaacgcg       2100
gcctttttac ggttcctggc cttttgctgg ccttttgctc acatgttctt cctgcgtta         2160 tcccctgatt ctgtggataa ccgtattacc gcctttgagt gagctgatac cgctcgccgc       2220
agccgaacga ccgagcgcag cgagtcagtg agcgaggaag cggaagagcg cctgatgcgg       2280
tattttctcc ttacgcatct gtgcggtatt tcacaccgca tatatggtgc actctcagta       2340
caatctgctc tgatgccgca tagttaagcc agtatacact ccgctatcgc tacgtgactg      2400
ggtcatggct gcgccccgac acccgccaac acccgctgac gcgccctgac gggcttgtct       2460
gctcccggca tccgcttaca gacaagctgt gaccgtctcc gggagctgca tgtgtcagag      2520
gttttcaccg tcatcaccga aacgcgcgag gcagctgcgg taaagctcat cagcgtggtc      2580
gtgaagcgat tcacagatgt ctgcctgttc atccgcgtcc agctcgttga gtttctccag      2640
aagcgttaat gtctggcttc tgataaagcg ggccatgtta agggcggttt tttcctgttt     2700
ggtcactgat gcctccgtgt aagggggatt tctgttcatg ggggtaatga taccgatgaa     2760
acgagagagg atgctcacga tacgggttac tgatgatgaa catgcccggt tactggaacg      2820
ttgtgagggt aaacaactgg cggtatggat gcggcgggac cagagaaaaa tcactcaggg      2880
tcaatgccag cgcttcgtta atacagatgt aggtgttcca cagggtagcc agcagcatcc      2940
tgcgatgcag atccggaaca taatggtgca gggcgctgac ttccgcgttt ccagacttta      3000
cgaaacacgg aaaccgaaga ccattcatgt tgttgctcag gtcgcagacg ttttgcagca      3060
gcagtcgctt cacgttcgct cgcgtatcgg tgattcattc tgctaaccag taaggcaacc     3120
ccgccagcct agccgggtcc tcaacgacag gagcacgatc atgcgcaccc gtggggccgc       3180
catgccggcg ataatggcct gcttctcgcc gaaacgtttg gtggcgggac cagtgacgaa      3240
ggcttgagcg agggcgtgca agattccgaa taccgcaagc gacaggccga tcatcgtcgc       3300
gctccagcga aagcggtcct cgccgaaaat gacccagagc gctgccggca cctgtcctac      3360
gagttgcatg ataagaaga cagtcataag tgcggcgacg atagtcatgc cccgcgccca      3420
ccggaaggag ctgactgggt tgaaggctct caagggcatc ggtcgagatc ccggtgccta      3480
```

-continued

```
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg cgcgcattg    3840 cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tccgcgtttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatatacc atgggcagca gccatcatca tcatcatcac   5100
agcagcggca aaatcgaaga aggtaaactg gtaatctgga ttaacggcga taaaggctat   5160
aacggtctcg ctgaagtcgg taagaaattc gagaaagata ccggaattaa agtcaccgtt   5220
gagcatccgg ataaactgga agagaaattc ccacaggttg cggcaactgg cgatggccct   5280
gacattatct ctgggcaca cgaccgcttt ggtggctacg ctcaatctgg cctgttggct    5340
gaaatcaccc cggacaaagc gttccaggac aagctgtatc cgtttacctg ggatgccgta   5400
cgttacaacg gcaagctgat tgcttacccg atcgctgttg aagcgttatc gctgatttat   5460
aacaaagatc tgctgccgaa cccgccaaaa acctgggaag atcccggc gctggataaa    5520 gaactgaaag cgaaaggtaa gagcgcgctg atgttcaacc tgcaagaacc gtacttcacc   5580
tggccgctga ttgctgctga cggggttat gcgttcaagt atgaaaacgg caagtacgac   5640 attaagacg tgggcgtgga taacgctggc gcgaaagcgg gtctgacctt cctggttgac   5700
ctgattaaaa acaaacacat gaatgcagac accgattact ccatcgcaga agctgccttt   5760
aataaaggcg aaacagcgat gaccatcaac ggcccgtggg catggtccaa catcgacacc   5820
agcaaagtga attatggtgt aacggtactg ccgaccttca agggtcaacc atccaaaccg   5880
```

-continued

| | |
|---|---|
| ttcgttggcg tgctgagcgc aggtattaac gccgccagtc cgaacaaaga gctggcaaaa | 5940 |
| gagttcctcg aaaactatct gctgactgat gaaggtctgg aagcggttaa taaagacaaa | 6000 |
| ccgctgggtg ccgtagcgct gaagtcttac gaggaagagt tggcgaaaga tccacgtatt | 6060 |
| gccgccacta tggaaaacgc ccagaaaggt gaaatcatgc cgaacatccc gcagatgtcc | 6120 |
| gctttctggt atgccgtgcg tactgcggtg atcaacgccg ccagcggtcg tcagactgtc | 6180 |
| gatgaagccc tgaaagacgc gcagactagc agcggcctgg tgccgcgcgg cagccatatg | 6240 |
| cgcccaatga ccgctaaaat cttcgccgtc gactccgtcc gtccgatcga cgagtttgag | 6300 |
| caggacgcac tgcgcgttgc ggatgtgatt cgcgaacgtg gcgtgtgtct gggtgaccgt | 6360 |
| gtgatgttga aggcgggcaa cagcgcgtcg tacgtttgcg ttttgtatgc gctgatgcac | 6420 |
| atcggtgcga gcatcgtttt ggtcgatcag caagagcata agaggaaaac ccgtcgtatc | 6480 |
| gcgctgcgta ccggcgtaaa agtcacgttt gtggatgatg aaaccccgat tgatcaagat | 6540 |
| gcggacccga ttcacctgta cgagctgatg gtggctaccc agaaccgtcc tccgatggac | 6600 |
| agcgcactga gcttcgacgc gtggggtgaa ctgtctgacg gtctgattat gtggacgagc | 6660 |
| ggcagcaccg gtagcccgaa gggtgtcgtg aagagcggtg gtaaattcct ggcgaatctg | 6720 |
| cgccgtaacg cgcatcaagt gggtcatcgt ccggatgacg tgctgatgcc gctgctgccg | 6780 |
| ttcgcgcacc agtacggtct gtctatggtg ctgattgcat ggctgacgcg ctgctccctg | 6840 |
| gttattgcgc ataccgccg tctggatcgt gctttgcgta tggcccgtga cagcggcacg | 6900 |
| accgttatcg atgccacgcc gagcagctat cgcagcatcc tgggcctggt cacgcgtaaa | 6960 |
| ccggccctgc gtgcacacct ggccggcacc cgcatgttct gtgtgggcgc agcgccgttg | 7020 |
| gatgcgccgc tggtcgaaag ctacgttcaa gagtttggtc tgccgctgtt ggacagctat | 7080 |
| ggttctaccg agctgaacaa tatcgctttc gcgaccctgg ataatccggt ttcctgtggt | 7140 |
| cgcgcaatgg aaggtatcgg tctgcgtatt gttgacgaag atggtcgtga agttgcggca | 7200 |
| ggccaaccgg cgaaatcga ggttgacact ccggatgccc tggagggtca aatcgccgag | 7260 |
| gatggtagca ttattccggc accgaccggc tggcagcgta cgggcgatct gggtcacttg | 7320 |
| gacgccgacg gcaacctgta tgtcctgggt cgtaagtttg cggtccaccg catgggttat | 7380 |
| actttgtacc cagagctgat tgagcgcaaa gtggccgctg agggctgccc gacccgcatt | 7440 |
| gttccgctgc cggacgagct gcgtggtagc caactggtct ttttcgtgga agatgatgaa | 7500 |
| cagcgtgacg caggttactg gcgtgaacgt ctgtgcggtt tgctgccggc gttcgagcag | 7560 |
| ccgaacaagg tggtcgttct ggagcagttt cctctgaatc gcaatggcaa gccggacaag | 7620 |
| aaagagctga cccgtatggc ggcagaatga taaggatccg aattcgagct ccgtcgacaa | 7680 |
| gcttgcggcc gcactcgagc accaccacca ccaccactga gatccggctg ctaacaaagc | 7740 |
| ccgaaaggaa gctgagttgg ctgctgccac cgctgagcaa taactagcat aaccccttgg | 7800 |
| ggcctctaaa cgggtcttga ggggttttt gctgaaagga ggaactatat ccggat | 7856 |

<210> SEQ ID NO 9
<211> LENGTH: 264
<212> TYPE: PRT
<213> ORGANISM: Pseudomonas putida

<400> SEQUENCE: 9

Met Arg Ile Ala Leu Tyr Gln Gly Ala Pro Lys Pro Leu Asp Val Pro
1               5                   10                  15

Gly Asn Leu Gln Arg Leu Arg His Gln Ala Gln Leu Ala Ala Glu Arg
            20                  25                  30

Gly Ala Gln Leu Leu Val Cys Pro Glu Met Phe Leu Thr Gly Tyr Asn
            35                  40                  45

Ile Gly Leu Ala Gln Val Glu Arg Leu Ala Glu Ala Ala Asp Gly Pro
 50                  55                  60

Ala Ala Met Thr Val Val Glu Ile Ala Gln Ala His Arg Ile Ala Ile
 65                  70                  75                  80

Val Tyr Gly Tyr Pro Glu Arg Gly Asp Asp Gly Ala Ile Tyr Asn Ser
                 85                  90                  95

Val Gln Leu Ile Asp Ala His Gly Arg Ser Leu Ser Asn Tyr Arg Lys
            100                 105                 110

Thr His Leu Phe Gly Glu Leu Asp Arg Ser Met Phe Ser Pro Gly Ala
            115                 120                 125

Asp His Phe Pro Val Val Glu Leu Glu Gly Trp Lys Val Gly Leu Leu
130                 135                 140

Ile Cys Tyr Asp Ile Glu Phe Pro Glu Asn Ala Arg Arg Leu Ala Leu
145                 150                 155                 160

Asp Gly Ala Glu Leu Ile Leu Val Pro Thr Ala Asn Met Thr Pro Tyr
                165                 170                 175

Asp Phe Thr Cys Gln Val Thr Val Arg Ala Arg Ala Gln Glu Asn Gln
            180                 185                 190

Cys Tyr Leu Val Tyr Ala Asn Tyr Cys Gly Ala Glu Asp Glu Ile Glu
            195                 200                 205

Tyr Cys Gly Gln Ser Ser Ile Ile Gly Pro Asp Gly Ser Leu Leu Ala
            210                 215                 220

Met Ala Gly Arg Asp Glu Cys Gln Leu Leu Ala Glu Leu Glu His Glu
225                 230                 235                 240

Arg Val Val Gln Gly Arg Thr Ala Phe Pro Tyr Leu Thr Asp Leu Arg
                245                 250                 255

Gln Glu Leu His Leu Arg Lys Gly
            260

<210> SEQ ID NO 10
<211> LENGTH: 560
<212> TYPE: PRT
<213> ORGANISM: Pseudomonas putida

<400> SEQUENCE: 10

Met Asn Lys Lys Asn Arg His Pro Ala Asp Gly Lys Lys Pro Ile Thr
 1               5                  10                  15

Ile Phe Gly Pro Asp Phe Pro Phe Ala Phe Asp Asp Trp Leu Glu His
                20                  25                  30

Pro Ala Gly Leu Gly Ser Ile Pro Ala Glu Arg His Gly Glu Glu Val
            35                  40                  45

Ala Ile Val Gly Ala Gly Ile Ala Gly Leu Val Ala Ala Tyr Glu Leu
 50                  55                  60

Met Lys Leu Gly Leu Lys Pro Val Val Tyr Glu Ala Ser Lys Leu Gly
 65                  70                  75                  80

Gly Arg Leu Arg Ser Gln Ala Phe Asn Gly Thr Asp Gly Ile Val Ala
                85                  90                  95

Glu Leu Gly Gly Met Arg Phe Pro Val Ser Ser Thr Ala Phe Tyr His
            100                 105                 110

Tyr Val Asp Lys Leu Gly Leu Glu Thr Lys Pro Phe Pro Asn Pro Leu
            115                 120                 125

Thr Pro Ala Ser Gly Ser Thr Val Ile Asp Leu Glu Gly Gln Thr Tyr
130                 135                 140

-continued

Tyr Ala Glu Lys Pro Thr Asp Leu Pro Gln Leu Phe His Glu Val Ala
145                 150                 155                 160

Asp Ala Trp Ala Asp Ala Leu Glu Ser Gly Ala Gln Phe Ala Asp Ile
            165                 170                 175

Gln Gln Ala Ile Arg Asp Arg Asp Val Pro Arg Leu Lys Glu Leu Trp
            180                 185                 190

Asn Lys Leu Val Pro Leu Trp Asp Asp Arg Thr Phe Tyr Asp Phe Val
            195                 200                 205

Ala Thr Ser Arg Ser Phe Ala Lys Leu Ser Phe Gln His Arg Glu Val
            210                 215                 220

Phe Gly Gln Val Gly Phe Gly Thr Gly Gly Trp Asp Ser Asp Phe Pro
225                 230                 235                 240

Asn Ser Met Leu Glu Ile Phe Arg Val Val Met Thr Asn Cys Asp Asp
            245                 250                 255

His Gln His Leu Val Val Gly Val Glu Gln Val Pro Gln Gly Ile
            260                 265                 270

Trp Arg His Val Pro Glu Arg Cys Val His Trp Pro Glu Gly Thr Ser
            275                 280                 285

Leu Ser Thr Leu His Gly Gly Ala Pro Arg Thr Gly Val Lys Arg Ile
            290                 295                 300

Ala Arg Ala Ser Asp Gly Arg Leu Ala Val Thr Asp Asn Trp Gly Asp
305                 310                 315                 320

Thr Arg His Tyr Ser Ala Val Leu Ala Thr Cys Gln Thr Trp Leu Leu
            325                 330                 335

Thr Thr Gln Ile Asp Cys Glu Glu Ser Leu Phe Ser Gln Lys Met Trp
            340                 345                 350

Met Ala Leu Asp Arg Thr Arg Tyr Met Gln Ser Ser Lys Thr Phe Val
            355                 360                 365

Met Val Asp Arg Pro Phe Trp Lys Asp Lys Asp Pro Glu Thr Gly Arg
            370                 375                 380

Asp Leu Leu Ser Met Thr Leu Thr Asp Arg Leu Thr Arg Gly Thr Tyr
385                 390                 395                 400

Leu Phe Asp Asn Gly Asn Asp Lys Pro Gly Val Ile Cys Leu Ser Tyr
            405                 410                 415

Ser Trp Met Ser Asp Ala Leu Lys Met Leu Pro His Pro Val Glu Lys
            420                 425                 430

Arg Val Gln Leu Ala Leu Asp Ala Leu Lys Lys Ile Tyr Pro Lys Thr
            435                 440                 445

Asp Ile Ala Gly His Ile Ile Gly Asp Pro Ile Thr Val Ser Trp Glu
450                 455                 460

Ala Asp Pro Tyr Phe Leu Gly Ala Phe Lys Gly Ala Leu Pro Gly His
465                 470                 475                 480

Tyr Arg Tyr Asn Gln Arg Met Tyr Ala His Phe Met Gln Gln Asp Met
            485                 490                 495

Pro Ala Glu Gln Arg Gly Ile Phe Ile Ala Gly Asp Val Ser Trp
            500                 505                 510

Thr Pro Ala Trp Val Glu Gly Ala Val Gln Thr Ser Leu Asn Ala Val
            515                 520                 525

Trp Gly Ile Met Asn His Phe Gly His Thr His Pro Asp Asn Pro
530                 535                 540

Gly Pro Gly Asp Val Phe Asn Glu Ile Gly Pro Ile Ala Leu Ala Asp
545                 550                 555                 560

-continued

```
<210> SEQ ID NO 11
<211> LENGTH: 41
<212> TYPE: DNA
<213> ORGANISM: Artificial Sequence
<220> FEATURE:
<223> OTHER INFORMATION: Primer designed to target C-6xHis-ORF27

<400> SEQUENCE: 11
gcgcgccatg ggcatgcgcc caatgaccgc taaaatcttc g                              41

<210> SEQ ID NO 12
<211> LENGTH: 33
<212> TYPE: DNA
<213> ORGANISM: Artificial Sequence
<220> FEATURE:
<223> OTHER INFORMATION: Primer designed to target C-6xHis-ORF27

<400> SEQUENCE: 12
gcgcgctcga gttctgccgc catacgggtc agc                                      33

<210> SEQ ID NO 13
<211> LENGTH: 859
<212> TYPE: PRT
<213> ORGANISM: Streptomyces aizunensis

<400> SEQUENCE: 13
```

Met Gly Ser Ser His His His His His Ser Ser Gly Lys Ile Glu
1               5                   10                  15

Glu Gly Lys Leu Val Ile Trp Ile Asn Gly Asp Lys Gly Tyr Asn Gly
            20                  25                  30

Leu Ala Glu Val Gly Lys Lys Phe Glu Lys Asp Thr Gly Ile Lys Val
        35                  40                  45

Thr Val Glu His Pro Asp Lys Leu Glu Glu Lys Phe Pro Gln Val Ala
    50                  55                  60

Ala Thr Gly Asp Gly Pro Asp Ile Ile Phe Trp Ala His Asp Arg Phe
65                  70                  75                  80

Gly Gly Tyr Ala Gln Ser Gly Leu Leu Ala Glu Ile Thr Pro Asp Lys
                85                  90                  95

Ala Phe Gln Asp Lys Leu Tyr Pro Phe Thr Trp Asp Ala Val Arg Tyr
            100                 105                 110

Asn Gly Lys Leu Ile Ala Tyr Pro Ile Ala Val Glu Ala Leu Ser Leu
        115                 120                 125

Ile Tyr Asn Lys Asp Leu Leu Pro Asn Pro Pro Lys Thr Trp Glu Glu
    130                 135                 140

Ile Pro Ala Leu Asp Lys Glu Leu Lys Ala Lys Gly Lys Ser Ala Leu
145                 150                 155                 160

Met Phe Asn Leu Gln Glu Pro Tyr Phe Thr Trp Pro Leu Ile Ala Ala
                165                 170                 175

Asp Gly Gly Tyr Ala Phe Lys Tyr Glu Asn Gly Lys Tyr Asp Ile Lys
            180                 185                 190

Asp Val Gly Val Asp Asn Ala Gly Ala Lys Ala Gly Leu Thr Phe Leu
        195                 200                 205

Val Asp Leu Ile Lys Asn Lys His Met Asn Ala Asp Thr Asp Tyr Ser
    210                 215                 220

Ile Ala Glu Ala Ala Phe Asn Lys Gly Glu Thr Ala Met Thr Ile Asn
225                 230                 235                 240

Gly Pro Trp Ala Trp Ser Asn Ile Asp Thr Ser Lys Val Asn Tyr Gly
                245                 250                 255

```
Val Thr Val Leu Pro Thr Phe Lys Gly Gln Pro Ser Lys Pro Phe Val
            260                 265                 270

Gly Val Leu Ser Ala Gly Ile Asn Ala Ala Ser Pro Asn Lys Glu Leu
        275                 280                 285

Ala Lys Glu Phe Leu Glu Asn Tyr Leu Leu Thr Asp Glu Gly Leu Glu
    290                 295                 300

Ala Val Asn Lys Asp Lys Pro Leu Gly Ala Val Ala Leu Lys Ser Tyr
305                 310                 315                 320

Glu Glu Glu Leu Ala Lys Asp Pro Arg Ile Ala Ala Thr Met Glu Asn
                325                 330                 335

Ala Gln Lys Gly Glu Ile Met Pro Asn Ile Pro Gln Met Ser Ala Phe
            340                 345                 350

Trp Tyr Ala Val Arg Thr Ala Val Ile Asn Ala Ala Ser Gly Arg Gln
        355                 360                 365

Thr Val Asp Glu Ala Leu Lys Asp Ala Gln Thr Ser Ser Gly Leu Val
    370                 375                 380

Pro Arg Gly Ser His Met Arg Pro Met Thr Ala Lys Ile Phe Ala Val
385                 390                 395                 400

Asp Ser Val Arg Pro Ile Asp Glu Phe Glu Gln Asp Ala Leu Arg Val
                405                 410                 415

Ala Asp Val Ile Arg Glu Arg Gly Val Cys Leu Gly Asp Arg Val Met
            420                 425                 430

Leu Lys Ala Gly Asn Ser Ala Ser Tyr Val Cys Val Leu Tyr Ala Leu
        435                 440                 445

Met His Ile Gly Ala Ser Ile Val Leu Val Asp Gln Gln Glu His Lys
    450                 455                 460

Glu Glu Thr Arg Arg Ile Ala Leu Arg Thr Gly Val Lys Val Thr Phe
465                 470                 475                 480

Val Asp Asp Glu Thr Pro Ile Asp Gln Asp Ala Asp Pro Ile His Leu
                485                 490                 495

Tyr Glu Leu Met Val Ala Thr Gln Asn Arg Pro Pro Met Asp Ser Ala
            500                 505                 510

Leu Ser Phe Asp Ala Trp Gly Glu Leu Ser Asp Gly Leu Ile Met Trp
        515                 520                 525

Thr Ser Gly Ser Thr Gly Ser Pro Lys Gly Val Val Lys Ser Gly Gly
    530                 535                 540

Lys Phe Leu Ala Asn Leu Arg Arg Asn Ala His Gln Val Gly His Arg
545                 550                 555                 560

Pro Asp Asp Val Leu Met Pro Leu Leu Pro Phe Ala His Gln Tyr Gly
                565                 570                 575

Leu Ser Met Val Leu Ile Ala Trp Leu Thr Arg Cys Ser Leu Val Ile
            580                 585                 590

Ala Pro Tyr Arg Arg Leu Asp Arg Ala Leu Arg Met Ala Arg Asp Ser
        595                 600                 605

Gly Thr Thr Val Ile Asp Ala Thr Pro Ser Ser Tyr Arg Ser Ile Leu
    610                 615                 620

Gly Leu Val Thr Arg Lys Pro Ala Leu Arg Ala His Leu Ala Gly Thr
625                 630                 635                 640

Arg Met Phe Cys Val Gly Ala Ala Pro Leu Asp Ala Pro Leu Val Glu
                645                 650                 655

Ser Tyr Val Gln Glu Phe Gly Leu Pro Leu Leu Asp Ser Tyr Gly Ser
            660                 665                 670
```

Thr Glu Leu Asn Asn Ile Ala Phe Ala Thr Leu Asp Asn Pro Val Ser
            675                 680                 685

Cys Gly Arg Ala Met Glu Gly Ile Gly Leu Arg Ile Val Asp Glu Asp
        690                 695                 700

Gly Arg Glu Val Ala Ala Gly Gln Pro Gly Glu Ile Glu Val Asp Thr
705                 710                 715                 720

Pro Asp Ala Leu Glu Gly Gln Ile Ala Glu Asp Gly Ser Ile Ile Pro
                725                 730                 735

Ala Pro Thr Gly Trp Gln Arg Thr Gly Asp Leu Gly His Leu Asp Ala
            740                 745                 750

Asp Gly Asn Leu Tyr Val Leu Gly Arg Lys Phe Ala Val His Arg Met
        755                 760                 765

Gly Tyr Thr Leu Tyr Pro Glu Leu Ile Glu Arg Lys Val Ala Ala Glu
    770                 775                 780

Gly Cys Pro Thr Arg Ile Val Pro Leu Pro Asp Glu Leu Arg Gly Ser
785                 790                 795                 800

Gln Leu Val Phe Phe Val Glu Asp Asp Glu Gln Arg Asp Ala Gly Tyr
                805                 810                 815

Trp Arg Glu Arg Leu Cys Gly Leu Leu Pro Ala Phe Glu Gln Pro Asn
            820                 825                 830

Lys Val Val Leu Glu Gln Phe Pro Leu Asn Arg Asn Gly Lys Pro
        835                 840                 845

Asp Lys Lys Glu Leu Thr Arg Met Ala Ala Glu
    850                 855

<210> SEQ ID NO 14
<211> LENGTH: 10
<212> TYPE: PRT
<213> ORGANISM: Artificial Sequence
<220> FEATURE:
<223> OTHER INFORMATION: Peptide designed to link MBP and ORF27

<400> SEQUENCE: 14

Ser Ser Gly Leu Val Pro Arg Gly Ser His
1               5                   10

<210> SEQ ID NO 15
<211> LENGTH: 447
<212> TYPE: PRT
<213> ORGANISM: Escherichia coli

<400> SEQUENCE: 15

Met Asp Gln Thr Tyr Ser Leu Glu Ser Phe Leu Asn His Val Gln Lys
1               5                   10                  15

Arg Asp Pro Asn Gln Thr Glu Phe Ala Gln Ala Val Arg Glu Val Met
                20                  25                  30

Thr Thr Leu Trp Pro Phe Leu Glu Gln Asn Pro Lys Tyr Arg Gln Met
            35                  40                  45

Ser Leu Leu Glu Arg Leu Val Glu Pro Glu Arg Val Ile Gln Phe Arg
        50                  55                  60

Val Val Trp Val Asp Asp Arg Asn Gln Ile Gln Val Asn Arg Ala Trp
65                  70                  75                  80

Arg Val Gln Phe Ser Ser Ala Ile Gly Pro Tyr Lys Gly Gly Met Arg
                85                  90                  95

Phe His Pro Ser Val Asn Leu Ser Ile Leu Lys Phe Leu Gly Phe Glu
                100                 105                 110

-continued

```
Gln Thr Phe Lys Asn Ala Leu Thr Thr Leu Pro Met Gly Gly Gly Lys
            115                 120                 125

Gly Gly Ser Asp Phe Asp Pro Lys Gly Lys Ser Glu Gly Glu Val Met
130                 135                 140

Arg Phe Cys Gln Ala Leu Met Thr Glu Leu Tyr Arg His Leu Gly Ala
145                 150                 155                 160

Asp Thr Asp Val Pro Ala Gly Asp Ile Gly Val Gly Gly Arg Glu Val
                165                 170                 175

Gly Phe Met Ala Gly Met Met Lys Lys Leu Ser Asn Asn Thr Ala Cys
            180                 185                 190

Val Phe Thr Gly Lys Gly Leu Ser Phe Gly Gly Ser Leu Ile Arg Pro
        195                 200                 205

Glu Ala Thr Gly Tyr Gly Leu Val Tyr Phe Thr Glu Ala Met Leu Lys
    210                 215                 220

Arg His Gly Met Gly Phe Glu Gly Met Arg Val Ser Val Ser Gly Ser
225                 230                 235                 240

Gly Asn Val Ala Gln Tyr Ala Ile Glu Lys Ala Met Glu Phe Gly Ala
                245                 250                 255

Arg Val Ile Thr Ala Ser Asp Ser Ser Gly Thr Val Val Asp Glu Ser
            260                 265                 270

Gly Phe Thr Lys Glu Lys Leu Ala Arg Leu Ile Glu Ile Lys Ala Ser
        275                 280                 285

Arg Asp Gly Arg Val Ala Asp Tyr Ala Lys Glu Phe Gly Leu Val Tyr
    290                 295                 300

Leu Glu Gly Gln Gln Pro Trp Ser Leu Pro Val Asp Ile Ala Leu Pro
305                 310                 315                 320

Cys Ala Thr Gln Asn Glu Leu Asp Val Asp Ala Ser His Gln Leu Ile
                325                 330                 335

Ala Asn Gly Val Lys Ala Val Ala Glu Gly Ala Asn Met Pro Thr Thr
            340                 345                 350

Ile Glu Ala Thr Glu Leu Phe Gln Gln Ala Gly Val Leu Phe Ala Pro
        355                 360                 365

Gly Lys Ala Ala Asn Ala Gly Gly Val Ala Thr Ser Gly Leu Glu Met
    370                 375                 380

Ala Gln Asn Ala Ala Arg Leu Gly Trp Lys Ala Glu Lys Val Asp Ala
385                 390                 395                 400

Arg Leu His His Ile Met Leu Asp Ile His Ala Cys Val Glu His
                405                 410                 415

Gly Gly Glu Gly Glu Gln Thr Asn Tyr Val Gln Gly Ala Asn Ile Ala
            420                 425                 430

Gly Phe Val Lys Val Ala Asp Ala Met Leu Ala Gln Gly Val Ile
        435                 440                 445
```

<210> SEQ ID NO 16
<211> LENGTH: 390
<212> TYPE: PRT
<213> ORGANISM: Haloferax volcanii

<400> SEQUENCE: 16

```
Met Ser Pro Ala Pro Thr Asp Ile Val Glu Glu Phe Thr Arg Arg Asp
1               5                   10                  15

Trp Gln Gly Asp Asp Val Thr Gly Thr Val Arg Val Ala Met Ile Gly
                20                  25                  30

Leu Gly Trp Trp Thr Arg Asp Glu Ala Ile Pro Ala Val Glu Ala Ser
            35                  40                  45
```

-continued

```
Glu Phe Cys Glu Thr Thr Val Val Ser Ser Lys Glu Lys Ala
 50                  55                  60

Glu Gly Ala Thr Ala Leu Thr Glu Ser Ile Thr His Gly Leu Thr Tyr
 65                  70                  75                  80

Asp Glu Phe His Glu Gly Val Ala Ala Asp Ala Tyr Asp Ala Val Tyr
                 85                  90                  95

Val Val Thr Pro Asn Gly Leu His Leu Pro Tyr Val Glu Thr Ala Ala
                100                 105                 110

Glu Leu Gly Lys Ala Val Leu Cys Glu Lys Pro Leu Glu Ala Ser Val
                115                 120                 125

Glu Arg Ala Glu Lys Leu Val Ala Ala Cys Asp Arg Ala Asp Val Pro
130                 135                 140

Leu Met Val Ala Tyr Arg Met Gln Thr Glu Pro Ala Val Arg Arg Ala
145                 150                 155                 160

Arg Glu Leu Val Glu Ala Gly Val Ile Gly Glu Pro Val Phe Val His
                165                 170                 175

Gly His Met Ser Gln Arg Leu Leu Asp Glu Val Val Pro Asp Pro Asp
                180                 185                 190

Gln Trp Arg Leu Asp Pro Glu Leu Ser Gly Gly Ala Thr Val Met Asp
                195                 200                 205

Ile Gly Leu Tyr Pro Leu Asn Thr Ala Arg Phe Val Leu Asp Ala Asp
210                 215                 220

Pro Val Arg Val Arg Ala Thr Ala Arg Val Asp Asp Glu Ala Phe Glu
225                 230                 235                 240

Ala Val Gly Asp Glu His Val Ser Phe Gly Val Asp Phe Asp Asp Gly
                245                 250                 255

Thr Leu Ala Val Cys Thr Ala Ser Gln Ser Ala Tyr Gln Leu Ser His
                260                 265                 270

Leu Arg Val Thr Gly Thr Glu Gly Glu Leu Glu Ile Glu Pro Ala Phe
                275                 280                 285

Tyr Asn Arg Gln Lys Arg Gly Phe Arg Leu Ser Trp Gly Asp Gln Ser
290                 295                 300

Ala Asp Tyr Asp Phe Glu Gln Val Asn Gln Met Thr Glu Glu Phe Asp
305                 310                 315                 320

Tyr Phe Ala Ser Arg Leu Leu Ser Asp Ser Pro Ala Pro Asp Gly
                325                 330                 335

Asp His Ala Leu Val Asp Met Arg Ala Met Asp Ala Ile Tyr Ala Ala
                340                 345                 350

Ala Glu Arg Gly Thr Asp Val Ala Val Asp Ala Asp Ser Asp Ser
                355                 360                 365

Ala Asp Ser Asp Ser Ala Asp Ala Ala Ala Asn His Asp Ala Asp
370                 375                 380

Pro Asp Ser Asp Gly Thr
385                 390

<210> SEQ ID NO 17
<211> LENGTH: 412
<212> TYPE: PRT
<213> ORGANISM: Haloferax volcanii

<400> SEQUENCE: 17

Met Val Glu Gln Ala Lys Leu Ser Asp Pro Asn Ala Glu Tyr Thr Met
 1               5                   10                  15

Arg Asp Leu Ser Ala Glu Thr Ile Asp Ile Thr Asn Pro Arg Gly Gly
                 20                  25                  30
```

-continued

Val Arg Asp Ala Glu Ile Thr Asp Val Gln Thr Thr Met Val Asp Gly
         35                  40                  45

Asn Tyr Pro Trp Ile Leu Val Arg Val Tyr Thr Asp Ala Gly Val Val
 50                  55                  60

Gly Thr Gly Glu Ala Tyr Trp Gly Gly Asp Thr Ala Ile Ile Glu
 65                  70                  75                  80

Arg Met Lys Pro Phe Leu Val Gly Glu Asn Pro Leu Asp Ile Asp Arg
                 85                  90                  95

Leu Tyr Glu His Leu Val Gln Lys Met Ser Gly Glu Gly Ser Val Ser
             100                 105                 110

Gly Lys Val Ile Ser Ala Ile Ser Gly Ile Glu Ile Ala Leu His Asp
         115                 120                 125

Val Ala Gly Lys Leu Leu Asp Val Pro Ala Tyr Gln Leu Val Gly Gly
 130                 135                 140

Lys Tyr Arg Asp Glu Val Arg Val Tyr Cys Asp Leu His Thr Glu Asp
145                 150                 155                 160

Glu Ala Asn Pro Gln Ala Cys Ala Glu Glu Gly Val Arg Val Val Glu
                165                 170                 175

Glu Leu Gly Tyr Asp Ala Ile Lys Phe Asp Leu Asp Val Pro Ser Gly
            180                 185                 190

His Glu Lys Asp Arg Ala Asn Arg His Leu Arg Asn Pro Glu Ile Asp
        195                 200                 205

His Lys Val Glu Ile Val Glu Ala Val Thr Glu Ala Val Gly Asp Arg
    210                 215                 220

Ala Asp Val Ala Phe Asp Cys His Trp Ser Phe Thr Gly Gly Ser Ala
225                 230                 235                 240

Lys Arg Leu Ala Ser Glu Leu Glu Asp Tyr Asp Val Trp Trp Leu Glu
                245                 250                 255

Asp Pro Val Pro Pro Glu Asn His Asp Val Gln Lys Leu Val Thr Gln
            260                 265                 270

Ser Thr Thr Thr Pro Ile Ala Val Gly Glu Asn Val Tyr Arg Lys Phe
        275                 280                 285

Gly Gln Arg Thr Leu Leu Glu Pro Gln Ala Val Asp Ile Ile Ala Pro
    290                 295                 300

Asp Leu Pro Arg Val Gly Gly Met Arg Glu Thr Arg Lys Ile Ala Asp
305                 310                 315                 320

Leu Ala Asp Met Tyr Tyr Ile Pro Val Ala Met His Asn Val Ser Ser
                325                 330                 335

Pro Ile Gly Thr Met Ala Ser Ala Gln Val Ala Ala Ile Pro Asn
            340                 345                 350

Ser Leu Ala Leu Glu Tyr His Ser Tyr Gln Leu Gly Trp Trp Glu Asp
        355                 360                 365

Leu Val Glu Glu Asp Asp Leu Ile Gln Asn Gly His Met Glu Ile Pro
    370                 375                 380

Glu Lys Pro Gly Leu Gly Leu Thr Leu Asp Leu Asp Ala Val Glu Ala
385                 390                 395                 400

His Met Val Glu Gly Glu Thr Leu Phe Asp Glu Glu
                405                 410

<210> SEQ ID NO 18
<211> LENGTH: 289
<212> TYPE: PRT
<213> ORGANISM: Haloferax volcanii

<400> SEQUENCE: 18

Met His Tyr His Gln Leu Ala Val Ser Gly Glu Arg Arg Leu Thr Ala
1               5                   10                  15

Ser Arg Asp Ser Thr Thr Tyr Asp Leu Thr Ser Ala Asp Ala Asp Leu
            20                  25                  30

Arg Thr Phe Gly Asp Leu Ala Arg Val Ala Ser Ile Ala Arg Thr Ser
        35                  40                  45

Val Asp Arg Leu Ala Ala Glu Leu Thr Glu Asp Ala Asp Val Val Asp
    50                  55                  60

Asp Ala Phe Val Asp Arg His Ala Thr Val Pro Val Asp Ala Glu Glu
65                  70                  75                  80

Ile Trp Ala Ala Gly Val Thr Tyr Gln Ile Ser Glu Gln Ala Arg Glu
                85                  90                  95

Glu Glu Ser Ser Met Pro Asp Met Tyr Phe Asp Val Tyr Asp Ala Asp
            100                 105                 110

Arg Pro Glu Val Phe Phe Lys Ala Thr Pro Ser Arg Thr Val Glu Pro
        115                 120                 125

Gly Asp Ala Ile Gly Val Arg Gly Asp Ser Glu Trp Asp Val Pro Glu
    130                 135                 140

Pro Glu Leu Gly Ile Val Leu Arg Arg Gly Glu Ile Val Gly Tyr Thr
145                 150                 155                 160

Val Gly Asn Asp Val Ser Ser Arg Ser Ile Glu Gly Glu Asn Pro Leu
                165                 170                 175

Tyr Leu Pro Gln Ala Lys Val Tyr Asp Arg Cys Cys Ser Ile Gly Pro
            180                 185                 190

Cys Val Val Thr Pro Glu Asp Val Glu Asp Pro His Glu Leu Glu Met
        195                 200                 205

Ser Met Thr Ile Glu Arg Asp Gly Glu Val Ile Tyr Asp Asp Ala Thr
    210                 215                 220

Asn Thr Ser Glu Met Val Arg Ser Cys Asp Glu Leu Val Ser Tyr Phe
225                 230                 235                 240

Thr Arg His Asn Thr Val Pro Glu Leu Ala Val Ile Leu Thr Gly Thr
                245                 250                 255

Ser Leu Val Pro Glu Gln Pro Phe Asp Leu Gln Glu Gly Asp His Val
            260                 265                 270

Asp Ile Thr Ile Glu Gly Ile Gly Thr Leu Ser Asn Ser Val Thr Thr
        275                 280                 285

Val

<210> SEQ ID NO 19
<211> LENGTH: 482
<212> TYPE: PRT
<213> ORGANISM: Haloferax volcanii

<400> SEQUENCE: 19

Met Thr Asp Pro Ser Lys Asn Tyr Val Asn Gly Glu Trp Val Thr Ser
1               5                   10                  15

Glu Thr Gly Glu Thr Thr Glu Val Thr Asn Pro Ala Asn Pro Ser Glu
            20                  25                  30

Val Val Ala Ala Tyr Gln His Ser Asn Glu Asn Asp Ala Ala Ala Ala
        35                  40                  45

Val Asp Ala Ala Val Ala Ala Glu Asp Glu Trp Arg Asn Thr Pro Gly
    50                  55                  60

```
Pro Glu Arg Gly Arg Ile Leu Arg Glu Ala Gly Thr Leu Leu Ala Gln
 65                  70                  75                  80

Arg Lys Asp Glu Leu Thr Glu Ile Leu Thr Ala Glu Glu Gly Lys Ala
                 85                  90                  95

Arg Pro Glu Ala Ala Gly Glu Val Gln Arg Ala Ile Asp Ile Phe His
            100                 105                 110

Tyr Phe Ser Ser Lys Ala Ala Asp Leu Gly Gly Thr Lys Lys Gly Ala
        115                 120                 125

Ser Gly Pro Asn Thr Asn Leu Tyr Thr Arg Gln Glu Pro Val Gly Val
    130                 135                 140

Ala Ala Leu Ile Thr Pro Trp Asn Tyr Pro Ile Ala Ile Pro Ala Trp
145                 150                 155                 160

Lys Leu Ala Pro Ala Leu Ala Ala Gly Asn Thr Val Val Leu Lys Pro
                165                 170                 175

Ala Ser Ile Ala Pro Gly Val Val Ile Glu Ile Ala Arg Ala Leu Asp
            180                 185                 190

Glu Ala Gly Leu Pro Asp Gly Val Leu Asn Val Val Thr Gly Pro Gly
        195                 200                 205

Ser Ser Val Gly Ser Glu Phe Ile Gly Asn Glu Gly Thr Asp Leu Val
    210                 215                 220

Ser Phe Thr Gly Ser Ser Gln Val Gly Glu Met Val Tyr Glu Gln Ala
225                 230                 235                 240

Thr Asp Ala Gly Lys Arg Val Gln Thr Glu Leu Gly Gly Lys Asn Pro
                245                 250                 255

Thr Leu Val Ala Asp Ser Ala Asn Pro Ala Glu Ala Ala Asp Ile Val
            260                 265                 270

Ala Asn Gly Gly Phe Gly Thr Thr Gly Gln Ser Cys Thr Ala Cys Ser
        275                 280                 285

Arg Ala Ile Val His Glu Asp Val Tyr Asp Asp Phe Val Ala Glu Leu
    290                 295                 300

Val Asp Arg Ala Glu Ser Leu Asp Val Gly Pro Gly Thr Asp His Glu
305                 310                 315                 320

Met Gly Pro Gln Val Ser Glu Ser Glu Leu Ser Ser Thr Leu Glu Tyr
                325                 330                 335

Ile Asp Ile Ala Glu Ala Glu Gly Ala Thr Leu Val Ala Gly Gly Gly
            340                 345                 350

Val Pro Glu Gly Glu Ala Val Glu Thr Gly His Phe Val Glu Pro Thr
        355                 360                 365

Val Phe Thr Asp Val Asp Pro Asp Met Arg Ile Ala Gln Glu Glu Val
    370                 375                 380

Phe Gly Pro Val Val Ala Val Ile Glu Val Ser Asp Phe Asp Glu Gly
385                 390                 395                 400

Leu Ala Val Ala Asn Asp Val Asp Tyr Gly Leu Ser Ala Ser Ile Val
                405                 410                 415

Thr Asp Asp His Thr Glu Ala Asn Arg Phe Val Asp Glu Val Glu Ala
            420                 425                 430

Gly Val Val Lys Val Asn Asp Lys Thr Thr Gly Leu Glu Leu His Val
        435                 440                 445

Pro Phe Gly Gly Phe Lys Arg Ser Ser Glu Thr Trp Arg Glu Gln
    450                 455                 460

Gly Asp Ala Gly Leu Asp Phe Tyr Thr Ile Glu Lys Thr Val Tyr Asp
465                 470                 475                 480

Ser Tyr
```

<210> SEQ ID NO 20
<211> LENGTH: 547
<212> TYPE: PRT
<213> ORGANISM: Lactococcus lactis

<400> SEQUENCE: 20

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser Arg Glu Asp Met Lys Trp Ile Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Ile
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Asp Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Tyr
    130                 135                 140

Glu Ile Asp Arg Val Leu Ser Gln Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ala Leu Ser Leu Glu Lys Glu Ser Ser Thr Thr Asn Thr Thr Glu Gln
            180                 185                 190

Val Ile Leu Ser Lys Ile Glu Glu Ser Leu Lys Asn Ala Gln Lys Pro
        195                 200                 205

Val Val Ile Ala Gly His Glu Val Ile Ser Phe Gly Leu Glu Lys Thr
    210                 215                 220

Val Thr Gln Phe Val Ser Glu Thr Lys Leu Pro Ile Thr Thr Leu Asn
225                 230                 235                 240

Phe Gly Lys Ser Ala Val Asp Glu Ser Leu Pro Ser Phe Leu Gly Ile
                245                 250                 255

Tyr Asn Gly Lys Leu Ser Glu Ile Ser Leu Lys Asn Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asp Glu Asn Lys Met Ile Ser Leu Asn
    290                 295                 300

Ile Asp Glu Gly Ile Ile Phe Asn Lys Val Val Glu Asp Phe Asp Phe
305                 310                 315                 320

Arg Ala Val Val Ser Ser Leu Ser Glu Leu Lys Gly Ile Glu Tyr Glu
                325                 330                 335

Gly Gln Tyr Ile Asp Lys Gln Tyr Glu Glu Phe Ile Pro Ser Ser Ala
            340                 345                 350

Pro Leu Ser Gln Asp Arg Leu Trp Gln Ala Val Glu Ser Leu Thr Gln
        355                 360                 365

Ser Asn Glu Thr Ile Val Ala Glu Gln Gly Thr Ser Phe Phe Gly Ala
    370                 375                 380

-continued

Ser Thr Ile Phe Leu Lys Ser Asn Ser Arg Phe Ile Gly Gln Pro Leu
385                 390                 395                 400

Trp Gly Ser Ile Gly Tyr Thr Phe Pro Ala Ala Leu Gly Ser Gln Ile
            405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ser Ile Arg Glu Lys Leu Asn
        435                 440                 445

Pro Ile Cys Phe Ile Ile Asn Asn Asp Gly Tyr Thr Val Glu Arg Glu
        450                 455                 460

Ile His Gly Pro Thr Gln Ser Tyr Asn Asp Ile Pro Met Trp Asn Tyr
465                 470                 475                 480

Ser Lys Leu Pro Glu Thr Phe Gly Ala Thr Glu Asp Arg Val Val Ser
            485                 490                 495

Lys Ile Val Arg Thr Glu Asn Glu Phe Val Ser Val Met Lys Glu Ala
            500                 505                 510

Gln Ala Asp Val Asn Arg Met Tyr Trp Ile Glu Leu Val Leu Glu Lys
        515                 520                 525

Glu Asp Ala Pro Lys Leu Leu Lys Lys Met Gly Lys Leu Phe Ala Glu
530                 535                 540

Gln Asn Lys
545

<210> SEQ ID NO 21
<211> LENGTH: 453
<212> TYPE: PRT
<213> ORGANISM: Vibrio fluvialis

<400> SEQUENCE: 21

Met Asn Lys Pro Gln Ser Trp Glu Ala Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val Asn Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Phe Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Val His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Arg Glu Gly Ala Asp Thr Ile Ala Gly Phe Phe Ala Glu Pro
   210                 215                 220

Val Met Gly Ala Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
                260                 265                 270

Thr Tyr Asp Phe Thr Pro Asp Ala Ile Ile Ser Ser Lys Asn Leu Thr
                275                 280                 285

Ala Gly Phe Phe Pro Met Gly Ala Val Ile Leu Gly Pro Glu Leu Ser
           290                 295                 300

Lys Arg Leu Glu Thr Ala Ile Glu Ala Ile Glu Glu Phe Pro His Gly
305                 310                 315                 320

Phe Thr Ala Ser Gly His Pro Val Gly Cys Ala Ile Ala Leu Lys Ala
                325                 330                 335

Ile Asp Val Val Met Asn Glu Gly Leu Ala Glu Asn Val Arg Arg Leu
                340                 345                 350

Ala Pro Arg Phe Glu Glu Arg Leu Lys His Ile Ala Glu Arg Pro Asn
           355                 360                 365

Ile Gly Glu Tyr Arg Gly Ile Gly Phe Met Trp Ala Leu Glu Ala Val
   370                 375                 380

Lys Asp Lys Ala Ser Lys Thr Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
           420                 425                 430

Gln Met Asp Glu Met Phe Asp Lys Leu Glu Lys Ala Leu Asp Lys Val
           435                 440                 445

Phe Ala Glu Val Ala
   450

<210> SEQ ID NO 22
<211> LENGTH: 384
<212> TYPE: PRT
<213> ORGANISM: Azotobacter vinelandii

<400> SEQUENCE: 22

Met Ala Ser Val Ile Ile Asp Asp Thr Thr Leu Arg Asp Gly Glu Gln
1               5                   10                  15

Ser Ala Gly Val Ala Phe Asn Ala Asp Glu Lys Ile Ala Ile Ala Arg
            20                  25                  30

Ala Leu Ala Glu Leu Gly Val Pro Glu Leu Glu Ile Gly Ile Pro Ser
        35                  40                  45

Met Gly Glu Glu Glu Arg Glu Val Met His Ala Ile Ala Gly Leu Gly
    50                  55                  60

Leu Ser Ser Arg Leu Leu Ala Trp Cys Arg Leu Cys Asp Val Asp Leu
65                  70                  75                  80

Ala Ala Ala Arg Ser Thr Gly Val Thr Met Val Asp Leu Ser Leu Pro
                85                  90                  95

Val Ser Asp Leu Met Leu His His Lys Leu Asn Arg Asp Arg Asp Trp
            100                 105                 110

Ala Leu Arg Glu Val Ala Arg Leu Val Gly Glu Ala Arg Met Ala Gly
        115                 120                 125

Leu Glu Val Cys Leu Gly Cys Glu Asp Ala Ser Arg Ala Asp Leu Glu
130                 135                 140

Phe Val Gln Val Gly Glu Val Ala Gln Ala Gly Ala Arg Arg
145                 150                 155                 160

Leu Arg Phe Ala Asp Thr Val Gly Val Met Glu Pro Phe Gly Met Leu
                165                 170                 175

Asp Arg Phe Arg Phe Leu Ser Arg Arg Leu Asp Met Glu Leu Glu Val
            180                 185                 190

His Ala His Asp Asp Phe Gly Leu Ala Thr Ala Asn Thr Leu Ala Ala
            195                 200                 205

Val Met Gly Gly Ala Thr His Ile Asn Thr Thr Val Asn Gly Leu Gly
210                 215                 220

Glu Arg Ala Gly Asn Ala Ala Leu Glu Glu Cys Val Leu Ala Leu Lys
225                 230                 235                 240

Asn Leu His Gly Ile Asp Thr Gly Ile Asp Thr Arg Gly Ile Pro Ala
                245                 250                 255

Ile Ser Ala Leu Val Glu Arg Ala Ser Gly Arg Gln Val Ala Trp Gln
            260                 265                 270

Lys Ser Val Val Gly Ala Gly Val Phe Thr His Glu Ala Gly Ile His
275                 280                 285

Val Asp Gly Leu Leu Lys His Arg Arg Asn Tyr Glu Gly Leu Asn Pro
290                 295                 300

Asp Glu Leu Gly Arg Ser His Ser Leu Val Leu Gly Lys His Ser Gly
305                 310                 315                 320

Ala His Met Val Arg Asn Thr Tyr Arg Asp Leu Gly Ile Glu Leu Ala
                325                 330                 335

Asp Trp Gln Ser Gln Ala Leu Leu Gly Arg Ile Arg Ala Phe Ser Thr
            340                 345                 350

Arg Thr Lys Arg Ser Pro Gln Pro Ala Glu Leu Gln Asp Phe Tyr Arg
            355                 360                 365

Gln Leu Cys Glu Gln Gly Asn Pro Glu Leu Ala Ala Gly Gly Met Ala
370                 375                 380

<210> SEQ ID NO 23
<211> LENGTH: 421
<212> TYPE: PRT
<213> ORGANISM: Methanococcus aeolicus

<400> SEQUENCE: 23

Met Thr Leu Ala Glu Glu Ile Leu Ser Lys Lys Val Gly Lys Lys Val
1               5                   10                  15

Lys Ala Gly Asp Val Val Glu Ile Asp Ile Asp Leu Ala Met Thr His
                20                  25                  30

Asp Gly Thr Thr Pro Leu Ser Ala Lys Ala Phe Lys Gln Ile Thr Asp
            35                  40                  45

Lys Val Trp Asp Asn Lys Lys Ile Val Ile Val Phe Asp His Asn Val
        50                  55                  60

Pro Ala Asn Thr Leu Lys Ala Ala Asn Met Gln Lys Ile Thr Arg Glu
65                  70                  75                  80

Phe Ile Lys Glu Gln Asn Ile Ile Asn His Tyr Leu Asp Gly Glu Gly
                85                  90                  95

Val Cys His Gln Val Leu Pro Glu Asn Gly His Ile Gln Pro Asn Met
            100                 105                 110

Val Ile Ala Gly Gly Asp Ser His Thr Cys Thr Tyr Gly Ala Phe Gly
        115                 120                 125

Ala Phe Ala Thr Gly Phe Gly Ala Thr Asp Met Gly Asn Ile Tyr Ala
            130                 135                 140

Thr Gly Lys Thr Trp Leu Lys Val Pro Lys Thr Ile Arg Ile Asn Val
145                 150                 155                 160

Asn Gly Glu Asn Asp Lys Ile Thr Gly Lys Asp Ile Ile Leu Lys Ile
                165                 170                 175

Cys Lys Glu Val Gly Arg Ser Gly Ala Thr Tyr Met Ala Leu Glu Tyr
            180                 185                 190

Gly Gly Glu Ala Ile Lys Lys Leu Ser Met Asp Glu Arg Met Val Leu
        195                 200                 205

Ser Asn Met Ala Ile Glu Met Gly Gly Lys Val Gly Leu Ile Glu Ala
210                 215                 220

Asp Glu Thr Thr Tyr Asn Tyr Leu Arg Asn Val Gly Ile Ser Glu Glu
225                 230                 235                 240

Lys Ile Leu Glu Leu Lys Lys Asn Gln Ile Thr Ile Asp Glu Asn Asn
                245                 250                 255

Ile Asp Asn Asp Asn Tyr Tyr Lys Ile Ile Asn Ile Asp Ile Thr Asp
            260                 265                 270

Met Glu Glu Gln Val Ala Cys Pro His His Pro Asp Asn Val Lys Asn
        275                 280                 285

Ile Ser Glu Val Lys Gly Ala Pro Ile Asn Gln Val Phe Ile Gly Ser
290                 295                 300

Cys Thr Asn Gly Arg Leu Asn Asp Leu Arg Ile Ala Ser Lys Tyr Leu
305                 310                 315                 320

Lys Gly Lys Val His Asn Asp Val Arg Leu Ile Val Ile Pro Ala
                325                 330                 335

Ser Lys Ser Ile Phe Lys Gln Ala Leu Lys Glu Gly Leu Ile Asp Ile
            340                 345                 350

Phe Val Asp Ala Gly Ala Leu Ile Cys Thr Pro Gly Cys Gly Pro Cys
        355                 360                 365

Leu Gly Ala His Gln Gly Val Leu Gly Asp Gly Glu Val Cys Leu Ala
370                 375                 380

Thr Thr Asn Arg Asn Phe Lys Gly Arg Met Gly Asn Thr Thr Ala Glu
385                 390                 395                 400

Ile Tyr Leu Ser Ser Pro Ala Ile Ala Ala Lys Ser Ala Ile Lys Gly
                405                 410                 415

Tyr Ile Thr Asn Glu
            420

<210> SEQ ID NO 24
<211> LENGTH: 165
<212> TYPE: PRT
<213> ORGANISM: Methanococcus aeolicus

<400> SEQUENCE: 24

Met Ile Ile Lys Gly Asn Ile His Leu Phe Gly Asp Asp Ile Asp Thr
1               5                   10                  15

Asp Ala Ile Ile Pro Gly Ala Tyr Leu Lys Thr Thr Asp Pro Lys Glu
                20                  25                  30

Leu Ala Ser His Cys Met Ala Gly Ile Asp Glu Lys Phe Ser Thr Lys
            35                  40                  45

Val Lys Asp Gly Asp Ile Ile Val Ala Gly Glu Asn Phe Gly Cys Gly
        50                  55                  60

Ser Ser Arg Glu Gln Ala Pro Ile Ser Ile Lys His Thr Gly Ile Lys
65                  70                  75                  80

-continued

```
Ala Val Val Ala Glu Ser Phe Ala Arg Ile Phe Tyr Arg Asn Cys Ile
                85                  90                  95
Asn Ile Gly Leu Ile Pro Ile Thr Cys Glu Gly Ile Asn Glu Gln Ile
           100                 105                 110
Gln Asn Leu Lys Asp Gly Asp Thr Ile Glu Ile Asp Leu Gln Asn Glu
            115                 120                 125
Thr Ile Lys Ile Asn Ser Met Met Leu Asn Cys Gly Ala Pro Lys Gly
            130             135                 140
Ile Glu Lys Glu Ile Leu Asp Ala Gly Gly Leu Val Gln Tyr Thr Lys
145                 150                 155                 160
Asn Lys Leu Lys Lys
                165
```

HOST CELL MODIFIED TO PRODUCE LACTAMS

CROSS-REFERENCE TO RELATED APPLICATIONS

The application claims priority as a continuation application to PCT International Patent Application No. PCT/US2017/036168, filed Jun. 6, 2017, which claims priority to U.S. Provisional Patent Application Ser. No. 62/346,294, filed Jun. 6, 2016, which are herein incorporated by reference in their entireties.

STATEMENT OF GOVERNMENTAL SUPPORT

The invention was made with government support under Contract Nos. DE-AC02-05CH11231 awarded by the U.S. Department of Energy and grant no. NSF EEC 0540879 awarded by the National Science Foundation. The government has certain rights in the invention.

FIELD OF THE INVENTION

The present invention is in the field of microbial production of lactams.

BACKGROUND OF THE INVENTION

Lactams are important compounds used in the manufacture of commercial polymers. ε-Caprolactam (caprolactam) is used in the production of nylon 6 found in fabrics, coatings, plastics of many compositions, lubricants, etc. The worldwide use of nylons requires the production of approximately four million metric tons of caprolactam annually (1). δ-Valerolactam (valerolactam) has been proposed as a monomer for nylon 5 and nylon 6,5 synthesis, addition of which tunes the properties of the resulting polymers (2-4).

Currently, both caprolactam and valerolactam are synthesized from starting materials extracted from petroleum. Caprolactam production starts from cyclohexanone, which is first converted to its oxime. Treatment of this oxime with acid induces the Beckmann rearrangement to give caprolactam (5). Such production involves energy intensive processes and harsh acidic reaction conditions and produces large amount of waste salts. On the other hand, due to the lack of raw five-carbon petrochemical feedstocks, valerolactam is still too costly to achieve wide adoption for nylon synthesis.

Unlike chemical dehydration, enzymatic or whole-cell-catalyzed reactions can be performed at lower temperature and pressure. Although several ω-amino fatty acids have been biosynthesized (3, 6, 7), full biosynthetic pathways to produce lactams are largely unknown. This is due to a lack of enzymes capable of performing the last ring closing step. In terms of polymer chemistry, ring open polymerization of these lactam monomers is preferred over condensation of their corresponding ω-amino fatty acids, because condensation chemistry generates water during each monomer addition, and adversely impacts polymer properties such as molecular weight and polydispersity, and leads to undesirable thermal and mechanical properties. To date, only one enzyme, *Candida antarctica* lipase B (CALB, commercially available as N435), was reported to conduct a reversible aminolysis reaction that can be utilized for valerolactam and caprolactam synthesis (8). However, the reported enzymatic reaction occurs under vacuum over $P_2O_5$, and requires high temperature and long reaction times to overcome the energy barrier of lactam formation (70% conversion at 90° C. and 20% conversion at 55° C. over a three-day period). Also, the intermolecular aminolysis reaction results in multiple side products, including macrocyclic dimer and trimer lactams, which are hard to eliminate during product purification. As such, there is no suitable enzyme capable of synthesizing industrially important lactams under microbial fermentation conditions.

Previously, ORF27 from *Streptomyces aizunensis*, was hypothesized to be either a 4-aminobutyryl-CoA synthetase or a 4-guanidinobutyryl-CoA synthase (9-12), although we demonstrated that expression of ORF27 in vivo resulted in the formation of γ-butyrolactam from 4-aminobutyric acid (13).

SUMMARY OF THE INVENTION

The present invention provides for a genetically modified host cell comprising an ORF27 (or 2-pyrrolidone synthase), or an enzymatically active fragment thereof, or a fusion protein comprising an ORF27, or an enzymatically active fragment thereof, linked to a saccharide binding protein. In some embodiments, the ORF27 is heterologous to the host cell. In some embodiments, the 2-pyrrolidone synthase is *Streptomyces aizunensis* 2-pyrrolidone synthase or ORF27, or any enzyme capable of catalyzing the following reaction (1):

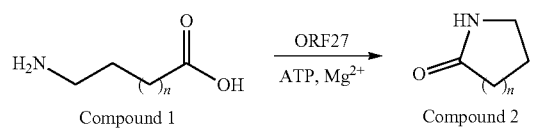

or reaction (2):

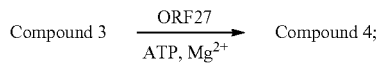

wherein Compound 3 is a "Substrate" and Compound 4 is a "Product" as indicated in Table 2 herein.

The present invention provides for a method of producing a Compound 2 in a genetically modified host cell, comprising: (a) culturing the genetically modified host cell in a medium under a suitable condition such that the culturing results in the genetically modified host cell producing a Compound 2. The host cell comprises an enzyme capable of catalyzing a Compound 1 into the Compound 2. In some embodiments, the method further comprises introducing one or more nucleic acid(s) into the host cell encoding the enzyme operably linked to a suitable promoter capable of transcription in the host cell, and optionally encoding the one or more enzyme(s) of a pathway for synthesizing Compound 1 from an endogenous produced substrate compound, such as produced from a carbon source, or a substrate compound obtained from the medium; wherein the introducing step is prior to the culturing step. In some embodiments, the method further comprises separating Compound 2 from the host cell and/or the medium, wherein the separating step is subsequent, concurrent or partially concurrent with the culturing step.

In some embodiments, the Compound 1 is aminobutyrate, and Compound 2 is 2-pyrrolidone. In some embodiments, Compound 1 is 5-AVA, and Compound 2 is valerolactam. In some embodiments, Compound 1 is 6-AHA, and Compound 2 is caprolactam.

In some embodiments, the fusion protein comprises the N-terminal of the ORF27, or an enzymatically active fragment thereof, linked to the C-terminal of the saccharide binding protein. In some embodiments, the fusion protein comprises the C-terminal of the ORF27, or an enzymatically active fragment thereof, linked to the N-terminal of the saccharide binding protein. In some embodiments, the saccharide binding protein is a disaccharide binding protein, such as a maltose binding protein (MBP), lactose binding protein, or sucrose binding protein. Suitable MBP include, but are not limited to, the MBPs of *Pyrococcus furiosus*, *Pyrobaculum aerophilum*, and *E. coli*. In some embodiments, the saccharide binding protein and ORF27 are linked via a peptide linker. In some embodiments, peptide linker is one to about twenty amino acid residues long. In some embodiments, peptide linker is about five to about fifteen amino acid residues long. In some embodiments, peptide linker is about ten amino acid residues long. A suitable peptide linker comprises: SSGLVPRGSH (SEQ ID NO:14). The peptide linker is any sequence of amino acid residues that does not interfere or reduce the enzymatic activity of the ORF27, or enzymatically active fragment thereof, and does not interfere or reduce the ability of the saccharide binding protein to stabilize the ORF27, or enzymatically active fragment thereof.

The present invention further provides for an isolated compound 2 produced from the method of the present invention.

ORF27 is an enzyme involved in the biosynthesis of ECO-02301 in *Streptomyces aizunensis*. ORF27 has a broad substrate spectrum and cyclizes γ-aminobutyric acid into butyrolactam, 5-aminovaleric acid (5-AVA) into 6-valerolactam, and 6-aminohexanoic acid (6-AHA) into ε-caprolactam. In one embodiment, the host cell, such as *E. coli*, expressing ORF27 produces valerolactam and/or caprolactam when 5-AVA and/or 6-AHA, respectively, are added to the culture medium. When integrated with a 5-AVA or 6-AHA precursor biosynthetic pathway, the host cell is able to produce valerolactam or caprolactam, respectively, from a substrate compound, such as lysine, which in turn can be synthesized from a carbon source, such as glucose. The carbon source can be a renewable source. U.S. Pat. No. 8,404,465 discloses the metabolic pathway, and corresponding enzymes, for synthesizing 6-AHA from lysine.

BRIEF DESCRIPTION OF THE DRAWINGS

The foregoing aspects and others will be readily appreciated by the skilled artisan from the following description of illustrative embodiments when read in conjunction with the accompanying drawings.

FIG. 7A. ORF27 catalyzed butyrolactam formation. A reaction mixture containing 57 μM of ORF27, 5 mM ω-amino fatty acids substrates, 1 mM ATP or ADP, 0.5 mM CoASH and 1 mM Mg(Cl)$_2$ in 100 mM HEPES (pH=8) was incubated at 25° C. for 19 h and quenched with methanol. The quenched reaction was filtered to get rid of protein aggregates before loading onto LC-MS.

FIG. 10. Sequence alignment of different maltose-binding periplasmic proteins (MBPs) from Pyrococcus furiosus, Pyrobaculum aerophilum, and E. coli (SEQ ID NOs:2-4, respectively). Amino acid sequences are aligned using ClustalW2 Multiple sequence alignment. Conserved amino acid residues are indicated by "*", ":", or "."

DETAILED DESCRIPTION OF THE INVENTION

Figure 1:
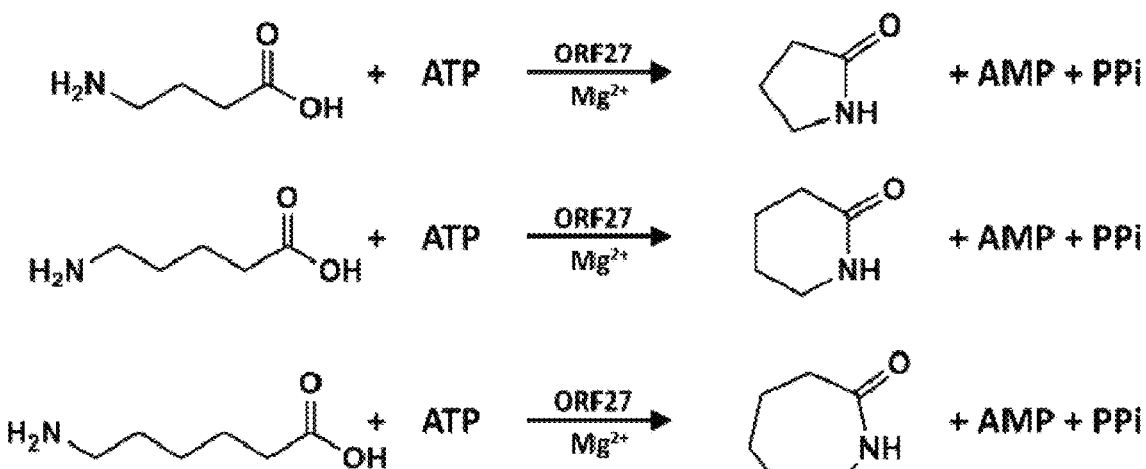
FIG. 1. Proposed butyrolactam, valerolactam and caprolactam formation from their respective linear substrates catalyzed by ORF27.

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

In order to more fully appreciate the invention the following definitions are provided.

As used in the specification and the appended claims, the singular forms "a," "an," and "the" include plural referents unless the context clearly dictates otherwise. Thus, for example, reference to an "expression vector" includes a single expression vector as well as a plurality of expression vectors, either the same (e.g., the same operon) or different; reference to "cell" includes a single cell as well as a plurality of cells; and the like.

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The term "enzymatically active fragment" is any enzyme that has an amino acid sequence that is at least 70%, 75%, 80%, 85%, 90%, 95% or 99% identical to the amino acid sequence of the indicated amino acid sequence. The enzymatically active fragment retains amino acids residues that are recognized as conserved for the enzyme. The enzymatically active fragment may have non-conserved amino acid residues replaced or found to be of a different amino acid, or amino acid(s) inserted or deleted, but which does not affect or has insignificant effect on the enzymatic activity of the enzymatically active fragment. The enzymatically active fragment may be found in nature or be an engineered mutant thereof.

The terms "host cell" and "host microorganism" are used interchangeably herein to refer to a living biological cell that can be transformed via insertion of an expression vector.

Thus, a host organism or cell as described herein may be a prokaryotic organism (e.g., an organism of the kingdom Eubacteria) or a eukaryotic cell. As will be appreciated by one of ordinary skill in the art, a prokaryotic cell lacks a membrane-bound nucleus, while a eukaryotic cell has a membrane-bound nucleus.

The term "heterologous DNA" as used herein refers to a polymer of nucleic acids wherein at least one of the following is true: (a) the sequence of nucleic acids is foreign to (i.e., not naturally found in) a given host microorganism; (b) the sequence may be naturally found in a given host microorganism, but in an unnatural (e.g., greater than expected) amount; or (c) the sequence of nucleic acids comprises two or more subsequences that are not found in the same relationship to each other in nature. For example, regarding instance (c), a heterologous nucleic acid sequence that is recombinantly produced will have two or more sequences from unrelated genes arranged to make a new functional nucleic acid. Specifically, the present invention describes the introduction of an expression vector into a host microorganism, wherein the expression vector contains a nucleic acid sequence coding for an enzyme that is not normally found in a host microorganism. With reference to the host microorganism's genome, then, the nucleic acid sequence that codes for the enzyme is heterologous.

The terms "expression vector" or "vector" refer to a compound and/or composition that transduces, transforms, or infects a host microorganism, thereby causing the cell to express nucleic acids and/or proteins other than those native to the cell, or in a manner not native to the cell. An "expression vector" contains a sequence of nucleic acids (ordinarily RNA or DNA) to be expressed by the host microorganism. Optionally, the expression vector also comprises materials to aid in achieving entry of the nucleic acid into the host microorganism, such as a virus, liposome, protein coating, or the like. The expression vectors contemplated for use in the present invention include those into which a nucleic acid sequence can be inserted, along with any preferred or required operational elements. Further, the expression vector must be one that can be transferred into a host microorganism and replicated therein. Preferred expression vectors are plasmids, particularly those with restriction sites that have been well documented and that contain the operational elements preferred or required for transcription of the nucleic acid sequence. Such plasmids, as well as other expression vectors, are well known to those of ordinary skill in the art.

The term "transduce" as used herein refers to the transfer of a sequence of nucleic acids into a host microorganism or cell. Only when the sequence of nucleic acids becomes stably replicated by the cell does the host microorganism or cell become "transformed." As will be appreciated by those of ordinary skill in the art, "transformation" may take place either by incorporation of the sequence of nucleic acids into the cellular genome, i.e., chromosomal integration, or by extrachromosomal integration. In contrast, an expression vector, e.g., a virus, is "infective" when it transduces a host microorganism, replicates, and (without the benefit of any complementary virus or vector) spreads progeny expression vectors, e.g., viruses, of the same type as the original transducing expression vector to other microorganisms, wherein the progeny expression vectors possess the same ability to reproduce.

The terms "isolated" or "biologically pure" refer to material that is substantially or essentially free of components that normally accompany it in its native state.

As used herein, the terms "nucleic acid sequence," "sequence of nucleic acids," and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing nonnucleotidic backbones, provided that the polymers contain nucleobases in a configuration that allows for base pairing and base stacking, as found in DNA and RNA. Thus, these terms include known types of nucleic acid sequence modifications, for example, substitution of one or more of the naturally occurring nucleotides with an analog; internucleotide modifications, such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters); those containing pendant moieties, such as, for example, proteins (including nucleases, toxins, antibodies, signal peptides, poly-L-lysine, etc.); those with intercalators (e.g., acridine, psoralen, etc.); and those containing chelators (e.g., metals, radioactive metals, boron, oxidative metals, etc.). As used herein, the symbols for nucleotides and polynucleotides are those recommended by the IUPAC-IUB Commission of Biochemical Nomenclature (*Biochem.* 9:4022, 1970).

The term "operably linked" refers to a functional linkage between a nucleic acid expression control sequence (such as a promoter) and a second nucleic acid sequence, wherein the expression control sequence directs transcription of the nucleic acid corresponding to the second sequence.

The amino acid sequence of *Streptomyces aizunensis* ORF27 is:

```
                                                        (SEQ ID NO: 1)
  1mrpmtakifa vdsvrpidef eqdalrvadv irergvclgd rvmlkagnsa syvcvlyalm 61higasivlvd qqehkeetrr ialrtgvkvt fvddetpidq dadpihlyel mvatqnrppm 121dsalsfdawg elsdglimwt sgstgspkgv vksggkflan lrrnahqvgh rpddvlmpll 181pfahqyglsm vliawltrcs lviapyrrld ralrmardsg ttvidatpss yrsilglvtr 241kpalrahlag trmfcvgaap ldaplvesyv qefglpllds ygstelnnia fatldnpvsc 301gramegiglr ivdedgreva agqpgeievd tpdalegqia edgsiipapt gwqrtgdlgh 361ldadgnlyvl grkfavhrmg ytlypelier kvaaegcptr ivplpdelrg sqlvffvedd 421eqrdagywre rlcgllpafe qpnkvvvleq fplnrngkpd kkeltrmaae
```

The enzymatically active fragment is any polypeptide capable of catalyzing reaction (1). The enzymatically active fragment is an enzyme that has an amino acid sequence that is at least 70%, 75%, 80%, 85%, 90%, 95% or 99% identical to the amino acid sequence of SEQ ID NO:1. The enzymatically active fragment retains amino acids residues that are recognized as conserved for the enzyme. The enzymatically active fragment may have non-conserved amino acid residues replaced or found to be of a different amino acid, or amino acid(s) inserted or deleted, but which does not affect or has insignificant effect on the enzymatic activity of the enzymatically active fragment. The enzymatically active fragment may be found in nature or be an engineered mutant thereof. The enzymatically active fragment can comprise one or more of the following conserved amino acid sites/residues:acyl-activating enzyme (AAE) consensus motif (residues 137, 140-145, 147-148), acyl-activating enzyme (AAE) consensus motif (residues 140, 257-258, 279-284, 357, 369, 372, 382, 458), AMP binding site (residues 140, 180-181, 227, 229-230, 233, 257-258, 279-284, 357, 369, 372, 379-382, 439), and CoA binding site (residues 180, 229-230, 233, 257, 379-381, 433, 439).

Suitable saccharide binding protein include any polypeptide when linked to ORF27 stabilizes ORF27, and having an amino acid sequence that is at least 70%, 75%, 80%, 85%, 90%, 95% or 99% identical to the amino acid sequence of SEQ ID NO:2, 3, or 4. The polypeptide when linked to ORF27 stabilizes ORF2 retains amino acids residues that are recognized as conserved for the enzyme, such as one or more conserved amino acid residues indicated in FIG. 10. In some embodiments, the polypeptide comprises all of the conserved amino acid residues indicated by "*", indicated by "*"and":", or indicated by "*", ":", and "." (as shown in FIG. 10); wherein for the conserved amino acid residues indicated by ":"and"." the amino acid residue can be the corresponding amino acid residue for any one of SEQ ID NOs: 2-4. The polypeptide when linked to ORF27 stabilizes ORF2 may have non-conserved amino acid residues replaced or found to be of a different amino acid, or amino acid(s) inserted or deleted, but which does not affect or has insignificant effect on the enzymatic activity of the enzymatically active fragment. The polypeptide when linked to ORF27 stabilizes ORF2 may be found in nature or be an engineered mutant thereof.

The amino acid sequence of a fusion MBP-ORF27 (the linker peptide is underlined and in bold) is the following:

```
                                              (SEQ ID NO: 13)
MGSSHHHHHH SSGKIEEGKL VIWINGDKGY NGLAEVGKKF

EKDTGIKVTV EHPDKLEEKF PQVAATGDGP DIIFWAHDRF
```

-continued
```
GGYAQSGLLA EITPDKAFQD KLYPFTWDAV RYNGKLIAYP

IAVEALSLIY NKDLLPNPPK TWEEIPALDK ELKAKGKSAL

MFNLQEPYFT WPLIAADGGY AFKYENGKYD IKDVGVDNAG

AKAGLTFLVD LIKNKHMNAD TDYSIAEAAF NKGETAMTIN

GPWAWSNIDT SKVNYGVTVL PTFKGQPSKP FVGVLSAGIN

AASPNKELAK EFLENYLLTD EGLEAVNKDK PLGAVALKSY

EEELAKDPRI AATMENAQKG EIMPNIPQMS AFWYAVRTAV

INAASGRQTV DEALKDAQTS SGLVPRGSHM RPMTAKIFAV

DSVRPIDEFE QDALRVADVI RERGVCLGDR VMLKAGNSAS

YVCVLYALMH IGASIVLVDQ QEHKEETRRI ALRTGVKVTF
```

VDDETPIDQD ADPIHLYELM VATQNRPPMD SALSFDAWGE

LSDGLIMWTS GSTGSPKGVV KSGGKFLANL RRNAHQVGHR

PDDVLMPLLP FAHQYGLSMV LIAWLTRCSL VIAPYRRLDR

ALRMARDSGT TVIDATPSSY RSILGLVTRK PALRAHLAGT

RMFCVGAAPL DAPLVESYVQ EFGLPLLDSY GSTELNNIAF

ATLDNPVSCG RAMEGIGLRI VDEDGREVAA GQPGEIEVDT

PDALEGQIAE DGSIIPAPTG WQRTGDLGHL DADGNLYVLG

RKFAVHRMGY TLYPELIERK VAAEGCPTRI VPLPDELRGS

QLVFFVEDDE QRDAGYWRER LCGLLPAFEQ PNKVVVLEQF

PLNRNGKPDK KELTRMAAE*

The nucleotide sequence of gBlock davB is the following:

(SEA ID NO: 5)
tatagggaattgtgagcggataacaatttcagaattcaaaagatctttt
aagaaggagatatacatatgaacaagaagaaccgccaccccgccgacggc
aagaagccgatcaccattttcggcccggacttccctttttgctttcgacga
ctggctggaacaccggcaggcctgggcagcattccggctgagcgccatg
gggaagaggtggccattgtcggtgccggtatcgccggcctggtagcggcc
tacgagctgatgaagctgggcctcaagccggtggtgtacgaggcttccaa
gctgggcggccggctgcgctcgcaagccttcaatggcactgacgggatcg
ttgccgagctgggtggcatgcgcttcccggtgtcgtccaccgccttctac
cactacgtcgacaagctgggcctggagaccaagcccttccccaacccgct
gaccccggcttcgggcagcacggtgatcgacctggaaggccagacctact
acgccgagaagcccaccgacctgccgcaactgtttcatgaggtagccgac
gcttgggccgatgtctctggagagcggtgcgcagttcgccgatatccagca
ggccatccgcgaccgtgatgtaccgcgcctgaaggaactctggaacaagc
tggtgccactgtgggacgaccgcacctttctacgacttcgtcgccacctcg
cgctcttttgccaagctgagcttccagcaccgcgaagtgttcggccaggt
cggtttcggcaccggcggtttgggactcggacttccccaactcgatgctgg
aaatcttccgcgtggtgatgaccaactgcgacgaccaccagcacctggtg
gtcggggcgtggaacaagtgccacaaggcatctggcgcgacgtaccgga
acgctgcgtgcattggccagagggcaccagcctgagcacgctgcatggcg
gcgcaccgcgtaccggggtcaagcgcattgcccgcgccgccgatggccgc
ctggcggtcaccgacaactggggcgatacccgccactacagcgcagtact
cgccacctgccagacctggttgctgaccacccagatcgactgcgaggaat
cgctgttctcgcaaaagatgtggatgccctggaccgtaccgtacatg
cagtcgtcgaaaaccttcgtcatggtcgaccgccgttctggaaggacaa
ggacccggaaaccggccgtgacctgctgagcatgaccctcaccgaccgcc
tcacccgcggcacttacctgttcgacaacggcaacgacaagcccggggtg
atctgcctgtcgtactcgtggatgagcgacgcgctgaagatgctgccgca
cccggtggaaaagcgcgtacaactggccctggatgcgctgaagaagatct acccgaagaccgatatcgccgggcacatcatcggcgacccgatcacggtt
tcctgggaggccgacccgtacttcctcggcgccttcaaaggcgcgcttcc
gggccattaccgctacaaccagcgcatgtacgcgcacttcatgcagcagg
acatgccggcggagcagcgcggtatcttcattgccggtgacgacgtgtca
tggaccccgcctgggttgaaggcgcggtgcagacgtcgctgaatgcggt
gtggggtatcatgaaccactttggtggccacacccaccccgacaacccg
gcccgggcgatgtgttcaacgaaatcggcccgatcgccctggcggattga
ggatcttttaagaaggagatatacatatgcgcatcgctct The nucleotide sequence of gBlock davA is the following:

(SEQ ID NO: 6)
Cccgatcgccctggcggattgaggatcttttaagaaggagatatacatat
gcgcatcgctctctgtaccagggcgcacccaagccactggatgtgcccggca
acctgcaacggctgcgccaccaggcgcagttggcagccgaccgcggcgca
cagttgctggtgtgcccggagatgttcctgtccggctacaacatcggcct
ggcccaggtcgagcgcctggccgaggccgccgatggcccggcagccatga
cggtggtggagattgcccaggcgcaccgtatcgccattgtctatggctac
ccggagcgcggcgatgacggggcgatctacaacagcgtgcagctgatcga
tgcgcatggccgcagcctgagcaattaccgcaagacccacctgttcggtg
aactggaccgctcgatgttcagccctggtgcggaccacttcccggtggtg
gaactggaaggctggaaggttggcctgctgatctgctacgacatcgagtt
cccggagaacgcccgacgcctggcgctggacggcgccgagctgatcctgg
tgccgacggcgaacatgacgccgtacgactttacctgccaggtgaccgtg
agggcacgggcgcaggaaaaccagtgctacctggtatatgccaactactg
cggcgcggaagacgagatcgagtattgcgggcagagcagcatcatcggcc
cggatggcagcttgctggccatggccgggcgggatgagtgccagttgttg
gcagagctcgagcatgagcgggtggtgcaggggcgcagggcgtttcccta
cctgaccgatttgcgccaggagctgcacctgcgtaaaggctgaggatcca
aactcgagtaaggatctccaggcatcaaatataaaacgaaaggctcagtc The nucleotide sequence of plasmid pBbA7a-DavB-DavA is the following:

(SEQ ID NO: 7)
gacgtcctcactgcccgctttccagtcgggaaacctgtcgtgccagctgc
attaatgaatcggccaacgcgcggggagaggcggtttgcgtattgggcgc
cagggtggttttcttttcaccagtgagacgggcaacagctgattgccct
tcaccgcctggccctgagagagttgcagcaagcggtccacgctggtttgc
cccagcaggcgaaaatcctgtttgatggtggttaacggcgggatataaca
tgagctgtcttcggtatcgtcgtatcccactaccgagatgtccgcaccaa
cgcgcagcccggactcggtaatgcgcgcattgcgcccagcgccatctga
tcgttggcaaccagcatcgcagtgggaacgatgccctcattcagcatttg
catggtttgttgaaaaccggacatggcactccagtcgccttcccgttccg
ctatcggctgaatttgattgcgagtgagatatttatgccagccagccaga -continued cgcagacgcgccgagacagaacttaatgggcccgctaacagcgcgatttg
ctggtgacccaatgcgaccagatgctccacgcccagtcgcgtaccgtctt
catgggagaaaataatactgttgatgggtgtctggtcagagacatcaaga
ataacgccggaacattagtgcaggcagcttccacagcaatggcatcctg
gtcatccagcggatagttaatgatcagcccactgacgcgttgcgcgagaa
gattgtgcaccgccgctttacaggcttcgacgccgcttcgttctaccatc
gacaccaccacgctggcacccagttgatcggcgcgagatttaatcgccgc
gacaatttgcgacggcgcgtgcagggccagactggaggtggcaacgccaa
tcagcaacgactgtttgcccgccagttgttgtgccacgcggttgggaatg
taattcagctccgccatcgccgcttccactttttcccgcgttttcgcaga
aacgtggctggcctggttcaccacgcgggaaacggtctgataagagacac
cggcatactctgcgacatcgtataacgttactggtttcacattcaccacc
ctgaattgactctcttccgggcgctatcatgccataccgcgaaaggtttt
gcgccattcgatggtgtccgggatctcgacgctctcccttatgcgactcc
tgcattaggaagcagcccagtagtaggttgaggccgttgagcaccgccgc
cgcaaggaatggtgcatgcaaggagatggcgcccaacagtccccggcca
cggggcctgccaccatacccacgccgaaacaagcgctcatgagcccgaag
tggcgagcccgatcttccccatcggtgatgtcggcgatataggcgccagc
aaccgcacctgtggcgccggtgatgccggccacgatgcgtccggcgtaga
ggatcgagatcgatctcgatcccgcgaaattaatacgactcactataggg
gaattgtgagcggataacaatttcagaattcaaaagatcttttaagaagg
agatatacatatgaacaagaagaaccgccaccccgccgacggcaagaagc
cgatcaccattttcggcccggacttcccttttgctttcgacgactggctg
gaacacccggcaggcctgggcagcattccggctgagcgccatggggaaga
ggtggccattgtcggtgccggtatcgccggcctggtagcggcctacgagc
tgatgaagctgggcctcaagccggtggtgtacgaggcttccaagctgggc
ggccggctgcgctcgcaagccttcaatggcactgacgggatcgttgccga
gctgggtggcatgcgcttcccggtgtcgtccaccgccttctaccactacg
tcgacaagctgggcctggagaccaagcccttccccaacccgctgaccccg
gcttcgggcagcacggtgatcgacctggaaggccagacctactacgccga
gaagcccaccgacctgccgcaactgtttcatgaggtagccgacgcttggg
ccgatgctctggagagcggtgcgcagttcgccgatatccagcaggccatc
cgcgaccgtgatgtaccgcgcctgaaggaactctggaacaagctggtgcc
actgtgggacgaccgcaccttctacgacttcgtcgccacctcgcgctctt
ttgccaagctgagcttccagcaccgcgaagtgttcggccaggtcggtttc
ggcaccggcggtttgggactcggacttccccaactcgatgctggaaatctt
ccgcgtggtgatgaccaactgcgacgaccaccagcacctggtggtcgggg
gcgtggaacaagtgccacaaggcatctggcgcgacgtaccggaacgctgc
gtgcattggccagagggcaccagcctgagcacgctgcatggcggcgcacc
gcgtaccgggtcaagcgcattgcccgcgccgccgatggccgcctggcgg
tcaccgacaactggggcgatacccgccactacagcgcagtactcgccacc -continued tgccagacctggttgctgaccacccagatcgactgcgaggaatcgctgtt
ctcgcaaaagatgtggatggccctggaccgtacccgctacatgcagtcgt
cgaaaaccttcgtcatggtcgaccgcccgttctggaaggacaaggacccg
gaaaccggccgtgacctgctgagcatgaccctcaccgaccgcctcacccg
cggcacttacctgttcgacaacggcaacgacaagcccggggtgatctgcc
tgtcgtactcgtggatgagcgacgcgctgaagatgctgccgcacccggtg
gaaaagcgcgtacaactggccctggatgcgctgaagaagatctacccgaa
gaccgatatcgccgggcacatcatcggcgacccgatcacggtttcctggg
aggccgaccgtacttcctcggcgccttcaaaggcgcgcttccgggccat
taccgctacaaccagcgcatgtacgcgcacttcatgcagcaggacatgcc
ggcgagcagcgcggtatcttcattgccggtgacgacgtgtcatggaccc
ccgcctgggttgaaggcgcggtgcagacgtcgctgaatgcggtgtggggt
atcatgaaccactttggtggccacacccaccccgacaaccccggcccggg
cgatgtgttcaacgaaatcggcccgatcgccctggcggattgaggatctt
ttaagaaggagatatacatatgcgcatcgctctgtaccagggcgcaccca
agccactggatgtgcccggcaacctgcaacggctgcgccaccaggcgcag
ttggcagccgaccgcggcacagttgctggtgtgcccggagatgttcct
gtccggctacaacatcggcctggcccaggtcgagcgcctggccgaggccg
ccgatggccggcagccatgacggtggtggagattgcccaggcgcaccgt
atcgccattgtctatggctacccggagcgcggcgatgacggggcgatcta
caacagcgtgcagctgatcgatgcgcatggccgcagcctgagcaattacc
gcaagacccacctgttcggtgaactggaccgctcgatgttcagccctggt
gcggaccacttcccggtggtggaactggaaggctggaaggttggcctgct
gatctgctacgacatcgagttcccggagaacgcccgacgcctggcgctgg
acgcgccgagctgatcctggtgccgacggcgaacatgacgccgtacgac
tttacctgccaggtgaccgtgagggcacgggcgcaggaaaaccagtgcta
cctggtatatgccaactactgcggcgcggaagacgagatcgagtattgcg
ggcagagcagcatcatcggcccggatggcagcttgctggccatggccggg
cgggatgagtgccagttgttggcagagctcgagcatgagcgggtggtgca
ggggcgcagggcgtttccctacctgaccgatttgcgccaggagctgcacc
tgcgtaaaggctgaggatccaaactcgagtaaggatctccaggcatcaaa
taaaacgaaaggctcagtcgaaagactgggcctttcgttttatctgttgt
ttgtcggtgaacgctctctactagagtcacactggctcaccttcggtgg
gcctttctgcgtttataccctagggatatattccgcttcctcgctcactga
ctcgctacgctcggtcgttcgactgcggcgagcggaaatggcttacgaac
ggggcggagatttcctggaagatgccaggaagatacttaacagggaagtg
agagggccgcggcaaagccgttttccataggctccgccccctgacaag
catcacgaaatctgacgctcaaatcagtggtggcgaaacccgacaggact
ataaagataccaggcgtttccccctggcggctccctcgtgcgctctcctg
ttcctgcctttcggtttaccggtgtcattccgctgttatggccgcgtttg
tctcattccacgcctgacactcagttccgggtaggcagttcgctccaagc -continued tggactgtatgcacgaaccccccgttcagtccgaccgctgcgccttatcc ggtaactatcgtcttgagtccaacccggaaagacatgcaaaagcaccact ggcagcagccactggtaattgatttagaggagttagtcttgaagtcatgc gccggttaaggctaaactgaaaggacaagttttggtgactgcgctcctcc aagccagttacctcggttcaaagagttggtagctcagagaaccttcgaaa aaccgccctgcaaggcggttttttcgttttcagagcaagagattacgcgc agaccaaaacgatctcaagaagatcatcttattaatcagataaaatattt ctagatttcagtgcaatttatctcttcaaatgtagcacctgaagtcagcc ccatacgatataagttgttactagtgcttggattctcaccaataaaaaac gcccggcggcaaccgagcgttctgaacaaatccagatggagttctgaggt cattactggatctatcaacaggagtccaagcgagctcgtaaacttggtct gacagttaccaatgcttaatcagtgaggcacctatctcagcgatctgtct atttcgttcatccatagttgcctgactccccgtcgtgtagataactacga tacgggagggcttaccatctggccccagtgctgcaatgataccgcgagac ccacgctcaccggctccagatttatcagcaataaaccagccagccggaag ggccgagcgcagaagtggtcctgcaactttatccgcctccatccagtcta -continued ttaattgttgccgggaagctagagtaagtagttcgccagttaatagtttg cgcaacgttgttgccattgctacaggcatcgtggtgtcacgctcgtcgtt tggtatggcttcattcagctccggttcccaacgatcaaggcgagttacat gatcccccatgttgtgcaaaaaagcggttagctccttcggtcctccgatc gttgtcagaagtaagttggccgcagtgttatcactcatggttatggcagc actgcataattctcttactgtcatgccatccgtaagatgcttttctgtga ctggtgagtactcaaccaagtcattctgagaatagtgtatgcggcgaccg agttgctcttgcccggcgtcaatacgggataataccgcgccacatagcag aactttaaaagtgctcatcattggaaaacgttcttcggggcgaaaactct caaggatcttaccgctgttgagatccagttcgatgtaacccactcgtgca cccaactgatcttcagcatcttttactttcaccagcgtttctgggtgagc aaaaacaggaaggcaaatgccgcaaaaaagggaataagggcgacacgga aatgttgaatactcatactcttccttttcaatattattgaagcatttat cagggttattgtctcatgagcggatacatatttgaatgtatttagaaaaa taaacaaataggggttccgcgcacatttccccgaaaagtgccacct The nucleotide sequence of plasmid pET28a-MBP-ORF27 is the following:

(SEQ ID NO: 8)
tggcgaatgggacgcgccctgtagcggcgcattaagcgcggcgggtgtggtggttacgcgcagc gtgaccgctacacttgccagcgccctagcgcccgctcctttcgctttcttcccttcctttctcg ccacgttcgccggctttccccgtcaagctctaaatcgggggctccctttagggttccgatttag tgctttacggcacctcgaccccaaaaaacttgattagggtgatggttcacgtagtgggccatcg ccctgatagacggtttttcgccctttgacgttggagtccacgttctttaatagtggactcttgt tccaaactggaacaacactcaaccctatctcggtctattcttttgatttataagggattttgcc gatttcggcctattggttaaaaaatgagctgatttaacaaaaatttaacgcgaattttaacaaa atattaacgtttacaatttcaggtggcacttttcggggaaatgtgcgcggaaccccctatttgtt tatttttctaaatacattcaaatatgtatccgctcatgaattaattcttagaaaaactcatcga gcatcaaatgaaactgcaatttattcatatcaggattatcaataccatattttgaaaaagccg tttctgtaatgaaggagaaaactcaccgaggcagttccataggatggcaagatcctggtatcgg tctgcgattccgactcgtccaacatcaatacaacctattaatttcccctcgtcaaaaataaggt tatcaagtgagaaatcaccatgagtgacgactgaatccggtgagaatggcaaaagtttatgcat ttctttccagacttgttcaacaggccagccattacgctcgtcatcaaaatcactcgcatcaacc aaaccgttattcattcgtgattgcgcctgagcgagacgaaatacgcgatcgctgttaaaaggac aattacaaacaggaatcgaatgcaaccggcgcaggaacactgccagcgcatcaacaatattttc acctgaatcaggatattcttctaatacctggaatgctgttttcccggggatcgcagtggtgagt aaccatgcatcatcaggagtacggataaaatgcttgatggtcggaagaggcataaattccgtca gccagtttagtctgaccatctcatctgtaacatcattggcaacgctacctttgccatgtttcag aaacaactctggcgcatcgggcttcccatacaatcgatagattgtcgcacctgattgcccgaca ttatcgcgagcccatttatacccatataaatcagcatccatgttggaatttaatcgcggcctag agcaagacgtttcccgttgaatatggctcataacaccccttgtattactgtttatgtaagcaga -continued

```
cagttttattgttcatgaccaaaatcccttaacgtgagttttcgttccactgagcgtcagaccc cgtagaaaagatcaaaggatcttcttgagatcctttttttctgcgcgtaatctgctgcttgcaa acaaaaaaccaccgctaccagcggtggtttgtttgccggatcaagagctaccaactcttttc cgaaggtaactggcttcagcagagcgcagataccaaatactgtccttctagtgtagccgtagtt aggccaccacttcaagaactctgtagcaccgcctacatacctcgctctgctaatcctgttacca gtggctgctgccagtggcgataagtcgtgtcttaccgggttggactcaagacgatagttaccgg ataaggcgcagcggtcgggctgaacggggggttcgtgcacacagcccagcttggagcgaacgac ctacaccgaactgagatacctacagcgtgagctatgagaaagcgccacgcttcccgaagggaga aaggcggacaggtatccggtaagcggcagggtcggaacaggagagcgcacgagggagcttccag ggggaaacgcctggtatctttatagtcctgtcgggtttcgccacctctgacttgagcgtcgatt tttgtgatgctcgtcagggggcggagcctatggaaaaacgccagcaacgcggccttttacgg ttcctggccttttgctggccttttgctcacatgttctttcctgcgttatcccctgattctgtgg ataaccgtattaccgcctttgagtgagctgataccgctcgccgcagccaacgaccgagcgcag cgagtcagtgagcgaggaagcggaagagcgcctgatgcggtattttctccttacgcatctgtgc ggtatttcacaccgcatatatggtgcactctcagtacaatctgctctgatgccgcatagttaag ccagtatacactccgctatcgctacgtgactgggtcatggctgcgccccgacacccgccaacac ccgctgacgcgccctgacgggcttgtctgctcccggcatccgcttacagacaagctgtgaccgt ctccgggagctgcatgtgtcagaggttttcaccgtcatcaccgaaacgcgcgaggcagctgcgg taaagctcatcagcgtggtcgtgaagcgattcacagatgtctgcctgttcatccgcgtccagct cgttgagtttctccagaagcgttaatgtctggcttctgataaagcgggccatgttaagggcggt ttttcctgtttggtcactgatgcctccgtgtaaggggatttctgttcatgggggtaatgata ccgatgaaacgagagaggatgctcacgatacgggttactgatgatgaacatgcccggttactgg aacgttgtgagggtaaacaactggcggtatggatgcggcgggaccagagaaaaatcactcaggg tcaatgccagcgcttcgttaatacagatgtaggtgttccacagggtagccagcagcatcctgcg atgcagatccggaacataatggtgcagggcgctgacttccgcgtttccagactttacgaaacac ggaaaccgaagaccattcatgttgttgctcaggtcgcagacgttttgcagcagcagtcgcttca cgttcgctcgcgtatcggtgattcattctgctaaccagtaaggcaaccccgccagcctagccgg gtcctcaacgacaggagcacgatcatgcgcacccgtggggccgccatgccggcgataatggcct gcttctcgccgaaacgtttggtggcgggaccagtgacgaaggcttgagcgagggcgtgcaagat tccgaataccgcaagcgacaggccgatcatcgtcgcgctccagcgaaagcggtcctcgccgaaa atgacccagagcgctgccggcacctgtcctacgagttgcatgataaagaagacagtcataagtg cggcgacgatagtcatgccccgcgcccaccggaaggagctgactgggttgaaggctctcaaggg catcggtcgagatcccggtgcctaatgagtgagctaacttacattaattgcgttgcgctcactg cccgctttccagtcgggaaacctgtcgtgccagctgcattaatgaatcggccaacgcgcgggga gaggcggtttgcgtattgggcgccagggtggttttttcttttcaccagtgagacgggcaacagct gattgcccttcaccgcctggccctgagagagttgcagcaagcggtccacgctggtttgccccag caggcgaaaatcctgtttgatggtggttaacggcgggatataacatgagctgtcttcggtatcg tcgtatcccactaccgagatatccgcaccaacgcgcagcccggactcggtaatggcgcgcattg cgcccagcgccatctgatcgttggcaaccagcatcgcagtgggaacgatgccctcattcagcat ttgcatggtttgttgaaaaccggacatggcactccagtcgccttcccgttccgctatcggctga atttgattgcgagtgagatatttatgccagccagccagacgcagacgcgccgagacagaactta
```

-continued

```
atgggcccgctaacagcgcgatttgctggtgaccaatgcgaccagatgctccacgcccagtcg cgtaccgtcttcatgggagaaaataatactgttgatgggtgtctggtcagagacatcaagaaat aacgccggaacattagtgcaggcagcttccacagcaatggcatcctggtcatccagcggatagt taatgatcagcccactgacgcgttgcgcgagaagattgtgcaccgccgctttacaggcttcgac gccgcttcgttctaccatcgacaccaccacgctggcacccagttgatcggcgcgagatttaatc gccgcgacaatttgcgacggcgcgtgcagggccagactggaggtggcaacgccaatcagcaacg actgtttgcccgccagttgttgtgccacgcggttgggaatgtaattcagctccgccatcgccgc ttccactttttcccgcgttttcgcagaaacgtggctggcctggttcaccacgcgggaaacggtc tgataagagacaccggcatactctgcgacatcgtataacgttactggttttcacattcaccaccc tgaattgactctcttccggcgctatcatgccataccgcgaaaggttttgcgccattcgatggt gtccgggatctcgacgctctcccttatgcgactcctgcattaggaagcagcccagtagtaggtt gaggccgttgagcaccgccgccgcaaggaatggtgcatgcaaggagatggcgcccaacagtccc ccggccacggggcctgccaccatacccacgccgaaacaagcgctcatgagcccgaagtggcgag cccgatcttccccatcggtgatgtcggcgatataggcgccagcaaccgcacctgtggcgccggt gatgccggccacgatgcgtccggcgtagaggatcgagatctcgatcccgcgaaattaatacgac tcactatagggaattgtgagcggataacaattcccctctagaaataattttgtttaactttaa gaaggagatataccatgggcagcagccatcatcatcatcatcacagcagcggcaaaatcgaaga aggtaaactggtaatctggattaacggcgataaaggctataacggtctcgctgaagtcggtaag aaattcgagaaagataccggaattaaagtcaccgttgagcatccggataaactggaagagaaat tcccacaggttgcggcaactggcgatggccctgacattatcttctgggcacacgaccgctttgg tggctacgctcaatctggcctgttggctgaaatcaccccggacaaagcgttccaggacaagctg tatccgtttacctgggatgccgtacgttacaacggcaagctgattgcttacccgatcgctgttg aagcgttatcgctgatttataacaaagatctgctgccgaacccgccaaaaacctgggaagagat cccggcgctggataaagaactgaaagcgaaaggtaagagcgcgctgatgttcaacctgcaagaa ccgtacttcacctggccgctgattgctgctgacggggttatgcgttcaagtatgaaaacggca agtacgacattaaagacgtgggcgtggataacgctggcgcgaaagcgggtctgaccttcctggt tgacctgattaaaaacaaacacatgaatgcagacaccgattactccatcgcagaagctgccttt aataaaggcgaaacagcgatgaccatcaacggcccgtgggcatggtccaacatcgacaccagca aagtgaattatggtgtaacggtactgccgaccttcaagggtcaaccatccaaaccgttcgttgg cgtgctgagcgcaggtattaacgccgccagtccgaacaaagagctggcaaaagagttcctcgaa aactatctgctgactgatgaaggtctggaagcggttaataaagacaaaccgctgggtgccgtag cgctgaagtcttacgaggaagagttggcgaaagatccacgtattgccgccactatggaaaacgc ccagaaaggtgaaatcatgccgaacatcccgcagatgtccgctttctggtatgccgtgcgtact gcggtgatcaacgccgccagcggtcgtcagactgtcgatgaagccctgaaagacgcgcagacta gcagcggcctggtgccgcgcggcagcCATATGCCCAATGACCGCTAAAATCTTCGCCGTCGA

CTCCGTCCGTCCGATCGACGAGTTTGAGCAGGACGCACTGCGCGTTGCGGATGTGATTCGCGAA

CGTGGCGTGTGTCTGGGTGACCGTGTGATGTTGAAGGCGGGCAACAGCGCGTCGTACGTTTGCG

TTTTGTATGCGCTGATGCACATCGGTGCGAGCATCGTTTTGGTCGATCAGCAAGAGCATAAAGA

GGAAACCCGTCGTATCGCGCTGCGTACCGGCGTAAAAGTCACGTTTGTGGATGATGAAACCCCG

ATTGATCAAGATGCGGACCCGATTCACCTGTACGAGCTGATGGTGGCTACCCAGAACCGTCCTC

CGATGGACAGCGCACTGAGCTTCGACGCGTGGGGTGAACTGTCTGACGGTCTGATTATGTGGAC
```

```
-continued
GAGCGGCAGCACCGGTAGCCCGAAGGGTGTCGTGAAGAGCGGTGGTAAATTCCTGGCGAATCTG

CGCCGTAACGCGCATCAAGTGGGTCATCGTCCGGATGACGTGCTGATGCCGCTGCTGCCGTTCG

CGCACCAGTACGGTCTGTCTATGGTGCTGATTGCATGGCTGACGCGCTGCTCCCTGGTTATTGC

GCCATACCGCCGTCTGGATCGTGCTTTGCGTATGGCCCGTGACAGCGGCACGACCGTTATCGAT

GCCACGCCGAGCAGCTATCGCAGCATCCTGGGCCTGGTCACGCGTAAACCGGCCCTGCGTGCAC

ACCTGGCCGGCACCCGCATGTTCTGTGTGGGCGCAGCGCCGTTGGATGCGCCGCTGGTCGAAAG

CTACGTTCAAGAGTTTGGTCTGCCGCTGTTGGACAGCTATGGTTCTACCGAGCTGAACAATATC

GCTTTCGCGACCCTGGATAATCCGGTTTCCTGTGGTCGCGCAATGGAAGGTATCGGTCTGCGTA

TTGTTGACGAAGATGGTCGTGAAGTTGCGGCAGGCCAACCGGGCGAAATCGAGGTTGACACTCC

GGATGCCCTGGAGGGTCAAATCGCCGAGGATGGTAGCATTATTCCGGCACCGACCGGCTGGCAG

CGTACGGGCGATCTGGGTCACTTGGACGCCGACGGCAACCTGTATGTCCTGGGTCGTAAGTTTG

CGGTCCACCGCATGGGTTATACTTTGTACCCAGAGCTGATTGAGCGCAAAGTGGCCGCTGAGGG

CTGCCCGACCCGCATTGTTCCGCTGCCGGACGAGCTGCGTGGTAGCCAACTGGTCTTTTTCGTG

GAAGATGATGAACAGCGTGACGCAGGTTACTGGCGTGAACGTCTGTGCGGTTTGCTGCCGGCGT

TCGAGCAGCCGAACAAGGTGGTCGTTCTGGAGCAGTTTCCTCTGAATCGCAATGGCAAGCCGGA

CAAGAAAGAGCTGACCCGTATGGCGGCAGAATGATAAGGATCCgaattcgagctccgtcgacaa gcttgcggccgcactcgagcaccaccaccaccactgagatccggctgctaacaaagcccga aaggaagctgagttggctgctgccaccgctgagcaataactagcataacccttggggcctcta aacgggtcttgaggggttttttgctgaaaggaggaactatatccggat
```

In some embodiments, the host cell is capable of synthesizing Compound 1 or uptaking Compound 1 from the environment or culture. In some embodiments, the host cell further comprises one or more enzymes of a pathway for synthesizing Compound 1 from a carbon source. In some embodiments, the pathway for synthesizing Compound 1 from a carbon source is native to the host cell. In some embodiments, the pathway for synthesizing Compound 1 from a carbon source is heterologous to the host cell. In some embodiments, the carbon source is a carbon source the host cell in the wild-type form is capable of uptaking.

In some embodiments, the host cell comprises a first one or more nucleic acids encoding the 2-pyrrolidone synthase, or an enzymatically active fragment thereof, operably linked to a promoter capable of expressing the 2-pyrrolidone synthase, or an enzymatically active fragment thereof, in the host cell. In some embodiments, the host cell comprises a second one or more nucleic acids encoding one or more enzymes of a pathway for synthesizing Compound 1 from a carbon source, operably linked to a promoter capable of expressing the one or more enzymes of a pathway for synthesizing Compound 1 from a carbon source in the host cell. In some embodiments, the first and/or second nucleic acids are stably integrated into a chromosome of the host cell. In some embodiments, the first and/or second nucleic acids are capable of stable introduction into the host cell. In some embodiments, the first and/or second nucleic acids are vectors, or expression vectors. In some embodiments, the first and/or second nucleic acids are the same nucleic acid. In some embodiments, the first and/or second nucleic acids are separate nucleic acids.

In some embodiments, the host cell lacks, or is disrupted for, an endogenous gene encoding betaine-CoA ligase. In some embodiments, the host cell lacks, or is disrupted for, an endogenous gene encoding a GABA transaminase, such as a gabT gene. In some embodiments, the host cell comprises an endogenous gene encoding a GadB, or the host cell expresses a heterologous GadB. In some embodiments, the host cell expresses a GadB mutant lacking amino acid residues H465 and T466, GadB_ΔHT (13).

In some embodiments, the host cell comprises endogenous or heterologous genes encoding a L-lysine monoxygenase, such as *Pseudomonas putida* davB gene, or enzymatically active fragment thereof, and a 5-aminovaleramide amidohydrolase, such as *Pseudomonas putida* davA gene, or enzymatically active fragment thereof.

The amino acid sequence of *Pseudomonas putida* DavA is:

```
                                              (SEQ ID NO: 9)
           10         20         30         40
    MRIALYQGAP KPLDVPGNLQ RLRHQAQLAA ERGAQLLVCP 50         60         70         80
    EMFLTGYNIG LAQVERLAEA ADGPAAMTVV EIAQAHRIAI 90        100        110        120
    VYGYPERGDD GAIYNSVQLI DAHGRSLSNY RKTHLFGELD 130        140        150        160
    RSMFSPGADH FPVVELEGWK VGLLICYDIE FPENARRLAL 170        180        190        200
    DGAELILVPT ANMTPYDFTC QVTVRARAQE NQCYLVYANY 210        220        230        240
    CGAEDEIEYC GQSSIIGPDG SLLAMAGRDE CQLLAELEHE 250        260
    RVVQGRTAFP YLTDLRQELH LRKG
```

The amino acid sequence of *Pseudomonas putida* DavB is:

```
                                          (SEQ ID NO: 10)
         10         20         30         40
MNKKNRHPAD GKKPITIFGP DFPFAFDDWL EHPAGLGSIP 50         60         70         80
AERHGEEVAI VGAGIAGLVA AYELMKLGLK PVVYEASKLG 90        100        110        120
GRLRSQAFNG TDGIVAELGG MRFPVSSTAF YHYVDKLGLE 130        140        150        160
TKPFPNPLTP ASGSTVIDLE GQTYYAEKPT DLPQLFHEVA 170        180        190        200
DAWADALESG AQFADIQQAI RDRDVPRLKE LWNKLVPLWD 210        220        230        240
DRTFYDFVAT SRSFAKLSFQ HREVFGQVGF GTGGWDSDFP 250        260        270        280
NSMLEIFRVV MTNCDDHQHL VVGGVEQVPQ GIWRHVPERC 290        300        310        320
VHWPEGTSLS TLHGGAPRTG VKRIARASDG RLAVTDNWGD 330        340        350        360
TRHYSAVLAT CQTWLLTTQI DCEESLFSQK MWMALDRTRY 370        380        390        400
MQSSKTFVMV DRPFWKDKDP ETGRDLLSMT LTDRLTRGTY 410        420        430        440
LFDNGNDKPG VICLSYSWMS DALKMLPHPV EKRVQLALDA 450        460        470        480
LKKIYPKTDI AGHIIGDPIT VSWEADPYFL GAFKGALPGH 490        500        510        520
YRYNQRMYAH FMQQDMPAEQ RGIFIAGDDV SWTPAWVEGA 530        540        550        560
VQTSLNAVWG IMNHFGGHTH PDNPGPGDVF NEIGPIALAD
```

In some embodiments, n is an integer from 1 to 20. In some embodiments, n is an integer from 1 to 10. In some embodiments, n is an integer from 1 to 9. In some embodiments, n is an integer from 1 to 8. In some embodiments, n is an integer from 1 to 7. In some embodiments, n is an integer from 1 to 6. In some embodiments, n is an integer from 1 to 7. In some embodiments, n is an integer from 1 to 6. In some embodiments, n is an integer from 1 to 5. In some embodiments, n is an integer from 1 to 4. In some embodiments, n is an integer from 1 to 3. When n is 1, compound 2 is butyrolactam (2-pyrrolidone). When n is 2, compound 2 is valerolactam (2-piperidinone). When n is 3, compound 2 is caprolactam.

The host cell can be any eukaryotic cell, such as a yeast, or prokaryotic cell, such as a bacterium. In some embodiments, the host cell is yeast. Yeast host cells suitable for practice of the methods of the invention include, but are not limited to, Yarrowia, Candida, Bebaromyces, Saccharomyces, Schizosaccharomyces and Pichia, including engineered strains provided by the invention. In one embodiment, Saccharomyces cerevisae is the host cell. In one embodiment, the yeast host cell is a species of Candida, including but not limited to C. tropicalis, C. maltosa, C. apicola, C. paratropicalis, C. albicans, C. cloacae, C. guillermondii, C. intermedia, C. lipolytica, C. panapsilosis, C. zeylenoides, and C. tropicalis. In some embodiments the host cell is a bacterium, such as a Gram-positive or Gram-negative cell. Bacterial host cells suitable for practice of the methods of the invention include, but are not limited to, Escherichia, Bacillus, Salmonella, Klebsiella, Enterobacter, Pseudomonas, Streptomyces, Cynechocystis, Cynechococcus, Sinorhizobium, and Caulobacter, including engineered strains provided by the invention. In some embodiments, the 2-pyrrolidone synthase is heterologous to the host cell.

Figure 11:
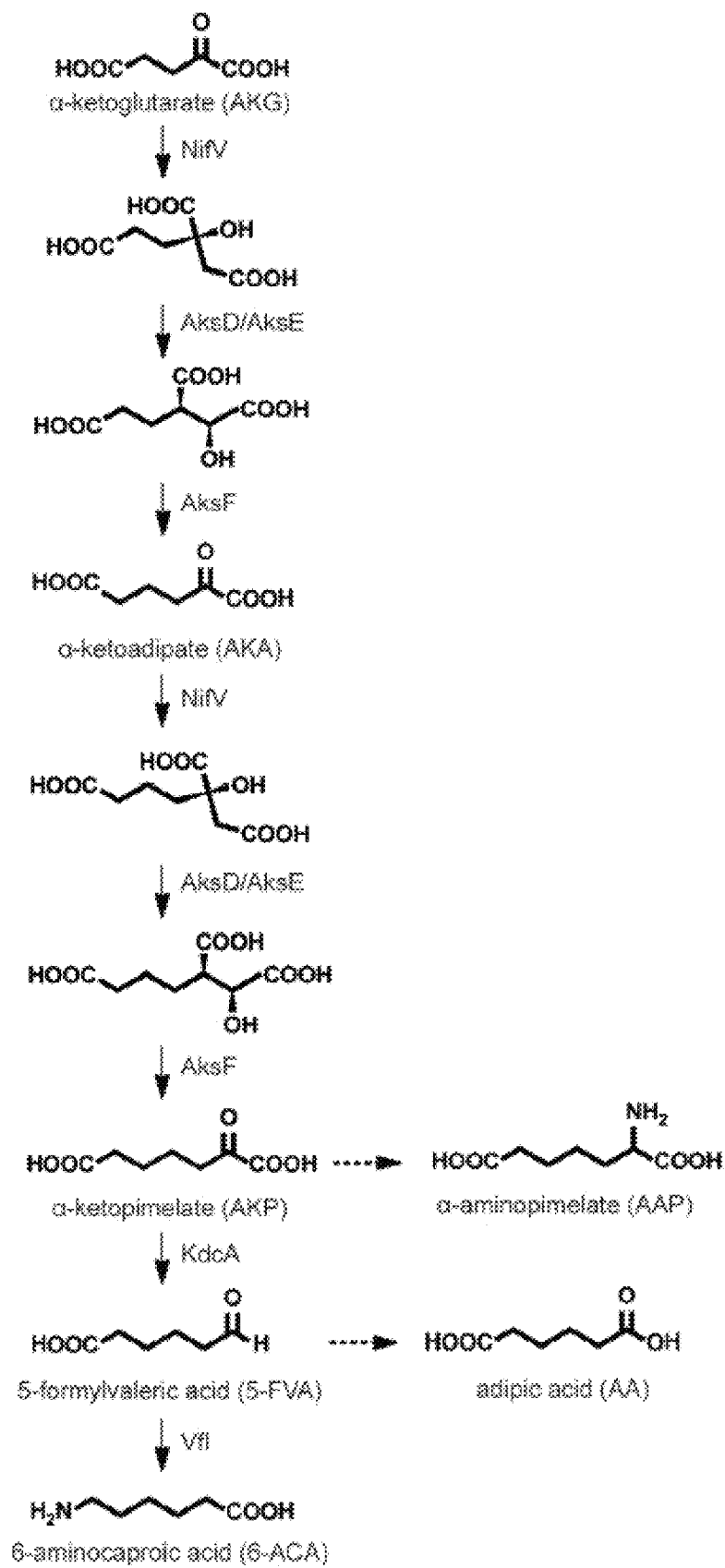
FIG. 11. The biosynthetic pathway from α-ketoglutarate to 6-ACA, AA, and/or AAP, and the respective enzymes which catalyzes each step.

In some embodiments, the host cell further comprises one or more, or all, of the biosynthetic enzymes, or enzymatically active fragments thereof, to convert α-ketoglutarate into 6-ACA, AA, and/or AAP, or any product in the pathway, shown in FIG. 11. The enzymes are taught in Zhou et al., "Algorithmic co-optimization of genetic constructs and growth conditions: application to 6-ACA, a potential nylon-6 precursor," Nucleic Acids Res 43(21): 10560 (2015).

In some embodiments, the host cell further comprises one or more endogenous or heterologous genes encoding a glutamate dehydrogenase, such as Escherichia coli glutamate dehydrogenase gene, or enzymatically active fragments thereof. The host cell is capable of expressing or overexpressing a glutamate dehydrogenase for conversion of glutamate to α-ketoglutarate.

The amino acid sequence of Escherichia coli glutamate dehydrogenase is:

```
                                          (SEQ ID NO: 15)
MDQTYSLESFLNHVQKRDPNQTEFAQAVREVMTTLWPFLEQNPKYRQMSL

LERLVEPERVIQFRVVWVDDRNQIQVNRAWRVQFSSAIGPYKGGMRFHPS

VNLSILKFLGFEQTFKNALTTLPMGGGKGGSDFDPKGKSEGEVMRFCQAL

MTELYRHLGADTDVPAGDIGVGGREVGFMAGMMKKLSNNTACVFTGKGLS

FGGSLIRPEATGYGLVYFTEAMLKRHGMGFEGMRVSVSGSGNVAQYAIEK

AMEFGARVITASDSSGTVVDESGFTKEKLARLIEIKASRDGRVADYAKEF

GLVYLEGQQPWSLPVDIALPCATQNELDVDASHQLIANGVKAVAEGANMP

TTIEATELFQQAGVLFAPGKAANAGGVATSGLEMAQNAARLGWKAEKVDA

RLHHIMLDIHHACVEHGGEGEQTNYVQGANIAGFVKVADAMLAQGVI
```

In some embodiments, the host cell further comprises endogenous and/or heterologous genes encoding a D-xylose dehydrogenase, such as Haloferax volcanii Hv-xdh gene, or enzymatically active fragments thereof, a D-xylonate dehydratase, such as Haloferax volcanii Hv-xad gene, or enzymatically active fragments thereof, a 2-keto-3-deoxyxylonate dehydratase, such as Haloferax volcanii Hv-HVO-B0027 gene, or enzymatically active fragments thereof, and an α-ketoglutarate semialdehyde dehydrogenase, such as Haloferax volcanii Hv-HVO-B0039 gene, or enzymatically active fragments thereof. The host cell is capable of expressing or overexpressing of the four-enzymes pathway from Haloferax volcanii for conversion of xylose to α-ketoglutarate production.

The amino acid sequence of Haloferax volcanii Hv-xdh is:

```
                                          (SEQ ID NO: 16)
MSPAPTDIVEEFTRRDWQGDDVTGTVRVAMIGLGWWTRDEAIPAVEASEF

CETTVVVSSSKEKAEGATALTESITHGLTYDEFHEGVAADAYDAVYVVTP

NGLHLPYVETAAELGKAVLCEKPLEASVERAEKLVAACDRADVPLMVAYR

MQTEPAVRRARELVEAGVIGEPVFVHGHMSQRLLDEVVPDPDQWRLDPEL

SGGATVMDIGLYPLNTARFVLDADPVRVRATARVDDEAFEAVGDEHVSFG

VDFDDGTLAVCTASQSAYQLSHLRVTGTEGELEIEPAFYNRQKRGFRLSW

GDQSADYDFEQVNQMTEEFDYFASRLLSDSDPAPDGDHALVDMRAMDAIY

AAAERGTDVAVDAADSDSADSDSADAAAANHDADPDSDGT
```

The amino acid sequence of *Haloferax volcanii* Hv-xad is:

(SEQ ID NO: 17)
MVEQAKLSDPNAEYTMRDLSAETIDITNPRGGVRDAEITDVQTTMVDGNY

PWILVRVYTDAGVVGTGEAYWGGGDTAIIERMKPFLVGENPLDIDRLYEH

LVQKMSGEGSVSGKVISAISGIEIALHDVAGKLLDVPAYQLVGGKYRDEV

RVYCDLHTEDEANPQACAEEGVRVVEELGYDAIKFDLDVPSGHEKDRANR

HLRNPEIDHKVEIVEAVTEAVGDRADVAFDCHWSFTGGSAKRLASELEDY

DVWWLEDPVPPENHDVQKLVTQSTTTPIAVGENVYRKFGQRTLLEPQAVD

IIAPDLPRVGGMRETRKIADLADMYYIPVAMHNVSSPIGTMASAQVAAAI

PNSLALEYHSYQLGWWEDLVEEDDLIQNGHMEIPEKPGLGLTLDLDAVEA

HMVEGETLFDEE

The amino acid sequence of *Haloferax volcanii* Hv-HVO-B0027 is:

(SEQ ID NO: 18)
MHYHQLAVSGERRLTASRDSTTYDLTSADADLRTFGDLARVASIARTSVD

RLAAELTEDADVVDDAFVDRHATVPVDAEEIWAAGVTYQISEQAREEESS

MPDMYFDVYDADRPEVFFKATPSRTVEPGDAIGVRGDSEWDVPEPELGIV

LRRGEIVGYTVGNDVSSRSIEGENPLYLPQAKVYDRCCSIGPCVVTPEDV

EDPHELEMSMTIERDGEVIYDDATNTSEMVRSCDELVSYFTRHNTVPELA

VILTGTSLVPEQPFDLQEGDHVDITIEGIGTLSNSVTTV

The amino acid sequence of *Haloferax volcanii* Hv-HVO-B0039 is:

(SEQ ID NO: 19)
MTDPSKNYVNGEWVTSETGETTEVTNPANPSEVVAAYQHSNENDAAAAVD

AAVAAEDEWRNTPGPERGRILREAGTLLAQRKDELTEILTAEEGKARPEA

AGEVQRAIDIFHYFSSKAADLGGTKKGASGPNTNLYTRQEPVGVAALITP

WNYPIAIPAWKLAPALAAGNTVVLKPASIAPGVVIEIARALDEAGLPDGV

LNVVTGPGSSVGSEFIGNEGTDLVSFTGSSQVGEMVYEQATDAGKRVQTE

LGGKNPTLVADSANPAEAADIVANGGFGTTGQSCTACSRAIVHEDVYDDF

VAELVDRAESLDVGPGTDHEMGPQVSESELSSTLEYIDIAEAEGATLVAG

GGVPEGEAVETGHFVEPTVFTDVDPDMRIAQEEVFGPVVAVIEVSDFDEG

LAVANDVDYGLSASIVTDDHTEANRFVDEVEAGVVKVNDKTTGLELHVPF

GGFKRSSSETWREQGDAGLDFYTIEKTVYDSY

In some embodiments, the host cell further comprises endogenous or heterologous genes encoding a indole-3-pyruvate decarboxylae, such as *Lactococcus lactis* KdcA gene, or enzymatically active fragments thereof, a pyruvate transaminase, such as *Vibrio fluvialis* Vfl gene, or enzymatically active fragments thereof, a homocitrate synthase, such as *Azotobacter vinelandii* NifVgene, or enzymatically active fragments thereof, a 3-isopropylmalate dehydratase large subunit, such as *Methanococcus aeolicus* AksD gene, or enzymatically active fragments thereof, a 3-isopropylmalate dehydratase small subunit, such as *Methanococcus aeolicus* AksE gene, or enzymatically active fragments thereof, a isopropylmalate/isohomocitrate dehydrogenase, such as *Methanococcus aeolicus* AksF gene, or enzymatically active fragments thereof. The host cell is capable of expressing or overexpressing of the six-enzyme pathway for 6-aminocaproic acid production.

The amino acid sequence of *Lactococcus lactis* KdcA is:

(SEQ ID NO: 20)
MYTVGDYLLDRLHELGIEEIFGVPGDYNLQFLDQIISREDMKWIGNANEL

NASYMADGYARTKKAAAFLTTFGVGELSAINGLAGSYAENLPVVEIVGSP

TSKVQNDGKFVHHTLADGDFKHFMKMHEPVTAARTLLTAENATYEIDRVL

SQLLKERKPVYINLPVDVAAAKAEKPALSLEKESSTTNTTEQVILSKIEE

SLKNAQKPVVIAGHEVISFGLEKTVTQFVSETKLPITTLNFGKSAVDESL

PSFLGIYNGKLSEISLKNFVESADFILMLGVKLTDSSTGAFTHHLDENKM

ISLNIDEGIIFNKVVEDFDFRAVVSSLSELKGIEYEGQYIDKQYEEFIPS

SAPLSQDRLWQAVESLTQSNETIVAEQGTSFFGASTIFLKSNSRFIGQPL

WGSIGYTFPAALGSQIADKESRHLLFIGDGSLQLTVQELGLSIREKLNPI

CFIINNDGYTVEREIHGPTQSYNDIPMWNYSKLPETFGATEDRVVSKIVR

TENEFVSVMKEAQADVNRMYWIELVLEKEDAPKLLKKMGKLFAEQNK

The amino acid sequence of *Vibrio fluvialis* Vfl is:

(SEQ ID NO: 21)
MNKPQSWEARAETYSLYGFTDMPSLHQRGTVVVTHGEGPYIVDVNGRRYL

DANSGLWNMVAGFDHKGLIDAAKAQYERFPGYHAFFGRMSDQTVMLSEKL

VEVSPFDSGRVFYTNSGSEANDTMVKMLWFLHAAEGKPQKRKILTRWNAY

HGVTAVSASMTGKPYNSVFGLPLPGFVHLTCPHYWRYGEEGETEEQFVAR

LARELEETIQREGADTIAGFFAEPVMGAGGVIPPAKGYFQAILPILRKYD

IPVISDEVICGFGRTGNTWGCVTYDFTPDAIISSKNLTAGFFPMGAVILG

PELSKRLETAIEAIEEFPHGFTASGHPVGCAIALKAIDVVMNEGLAENVR

RLAPRFEERLKHIAERPNIGEYRGIGFMWALEAVKDKASKTPFDGNLSVS

ERIANTCTDLGLICRPLGQSVVLCPPFILTEAQMDEMFDKLEKALDKVFA

EVA

The amino acid sequence of *Azotobacter vinelandii* NifV is:

(SEQ ID NO: 22)
MASVIIDDTTLRDGEQSAGVAFNADEKIAIARALAELGVPELEIGIPSMG

EEEREVMHAIAGLGLSSRLLAWCRLCDVDLAAARSTGVTMVDLSLPVSDL

MLHHKLNRDRDWALREVARLVGEARMAGLEVCLGCEDASRADLEFVVQVG

EVAQAAGARRLRFADTVGVMEPFGMLDRFRFLSRRLDMELEVHAHDDFGL

ATANTLAAVMGGATHINTTVNGLGERAGNAALEECVLALKNLHGIDTGID

TRGIPAISALVERASGRQVAWQKSVVGAGVFTHEAGIHVDGLLKHRRNYE

GLNPDELGRSHSLVLGKHSGAHMVRNTYRDLGIELADWQSQALLGRIRAF

STRTKRSPQPAELQDFYRQLCEQGNPELAAGGMA

The amino acid sequence of *Methanococcus aeolicus* AksD is:

(SEQ ID NO: 23)
MTLAEEILSKKVGKKVKAGDVVEIDIDLAMTHDGTTPLSAKAFKQITDKV

WDNKKIVIVFDHNVPANTLKAANMQKITREFIKEQNIINHYLDGEGVCHQ

VLPENGHIQPNMVIAGGDSHTCTYGAFGAFATGFGATDMGNIYATGKTWL

KVPKTIRINVNGENDKITGKDIILKICKEVGRSGATYMALEYGGEAIKKL

SMDERMVLSNMAIEMGGKVGLIEADETTYNYLRNVGISEEKILELKKNQI

TIDENNIDNDNYYKIINIDITDMEEQVACPHHPDNVKNISEVKGAPINQV

FIGSCTNGRLNDLRIASKYLKGKKVHNDVRLIVIPASKSIFKQALKEGLI

DIFVDAGALICTPGCGPCLGAHQGVLGDGEVCLATTNRNFKGRMGNTTAE

IYLSSPAIAAKSAIKGYITNE

The amino acid sequence of *Methanococcus aeolicus* AksE is:

(SEQ ID NO: 24)
MIIKGNIHLFGDDIDTDAIIPGAYLKTTDPKELASHCMAGIDEKFSTKVK

DGDIIVAGENFGCGSSREQAPISIKHTGIKAVVAESFARIFYRNCINIGL

IPITCEGINEQIQNLKDGDTIEIDLQNETIKINSMMLNCGAPKGIEKEIL

DAGGLVQYTKNKLKK

The amino acid sequence of *Methanococcus aeolicus* AksF is:

(SEQ ID NO: 25)
MKIPKICVIEGDGIGKEVIPETVRILKEIGDFEFIYEHAGYECFKRCGDA

IPEKTLKTAKECDAILFGAVSTPKLDETERKPYKSPILTLRKELDLYANV

RPIHKLDNSDSSNNIDFIIIRENTEGLYSGVEYYDEEKELAISERHISKK

GSKRIIKFAFEYAVKHHRKKVSCIHKSNILRITDGLFLNIFNEFKEKYKN

EYNIEGNDYLVDATAMYILKSPQMFDVIVTTNLFGDILSDEASGLLGGLG

LAPSANIGDNYGLFEPVHGSAPDIAGKGVANPIAAVLSASMMLYYLDMKE

KSRLLKDAVKQVLAHKDITPDLGGNLKTKEVSDKIIEELRKIS

REFERENCES CITED

1. PCI-Nylon. 2011. Polyamide 6. website for pcinylon.com/index.php/markets-covered/polyamide-6. Accessed 2015-10-08.
2. Liu P, Zhang H, Lv M, Hu M, Li Z, Gao C, Xu P, Ma C. 2014. Enzymatic production of 5-aminovalerate from L-lysine using L-lysine monooxygenase and 5-aminovaleramide amidohydrolase. Sci Rep 4:5657.
3. Park S J, Kim E Y, Noh W, Park H M, Oh Y H, Lee S H, Song B K, Jegal J, Lee S Y. 2013. Metabolic engineering of *Escherichia coli* for the production of 5-aminovalerate and glutarate as C5 platform chemicals. Metab Eng 16:42-47.
4. Park S J, Oh Y H, Noh W, Kim H Y, Shin J H, Lee E G, Lee S, David Y, Baylon M G, Song B K, Jegal J, Lee S Y, Lee S H. 2014. High-level conversion of L-lysine into 5-aminovalerate that can be used for nylon 6,5 synthesis. Biotechnol J 9:1322-1328.
5. Josef Ritz, et al., doi:10.1002/14356007.a05_031.pub2. 2005. Caprolactam. Ullmann's Encyclopedia of Industrial Chemistry.
6. Kallifidas D, Thomas D, Doughty P, Paget M S. 2010. The sigmaR regulon of *Streptomyces coelicolor* A32 reveals a key role in protein quality control during disulphide stress. Microbiology 156:1661-1672.
7. Stefan C. H. J. Turk W P K, Dennis K Ninaber, Karin P. A. M Kolen, Julia Knutova, Erwin Suir, Martin Schurmann, Petronella C. Raemakers-Franken, Monica Muller, Stefaan M. A. De Wildeman, Leonie M Raamsdonk, Ruud van der Pol, Liang Wu, Margarida F Temudo, Rob van der Hoeven, Michiel Akeroyd, Roland E van der Stoel, Henk J. Noorman, Roel A. L. bovenberg, and Axel C. Trefzer. 2015. Metabolic engineering towards sustainable production of Nylon-6. ACS Synthetic Biology (Just Accepted) doi:10.1021/acssynbio.5b00129.
8. Stavila E, Loos K. 2013. Synthesis of lactams using enzyme-catalyzed aminolysis. Tetrahedron Letters 54:370-372.
9. Hui Hong T F, Peter F. Leadlay. 2013. A Common Origin for Guanidinobutanoate Starter Units in Antifungal Natural Products. Angewandte Chemie 124:13334-13337.
10. McAlpine. 2005. Microbial Genomics as a Guide to Drug Discovery and Structural Elucidation: ECO-02301, a Novel Antifungal Agent, as an Example. J Nat Prod: 493-496.
11. Zazopoulos. 2003. A genomics-guided approach for discovering and expressing cryptic metabolic pathways. Nat Biotechnol 21:187-190.
12. Zhang. 2010. A Three Enzyme Pathway for 2-Amino-3-hydroxycyclopent-2-enone Formation and Incorporation in Natural Product Biosynthesis. J AM CHEM SOC 132:6402-6411.
13. Zhang J, Kao, E., Wang G., Baidoo E. E. K., Chen, M., Keasling, J. 2016. Metabolic Engineering of *E. coli* for the biosynthesis of 2-pyrrolidone. Met Eng Comm 3:1-7.
14. Yuzawa S, Chiba N, Katz L, Keasling J D. 2012. Construction of a part of a 3-hydroxypropionate cycle for heterologous polyketide biosynthesis in *Escherichia coli*. Biochemistry 51:9779-9781.
15. Tomoya Baba T A, Miki Hasegawa, Yuki Takai, Yoshiko Okumura, Miki Baba, Kirill A Datsenko, Masaru Tomita, Barry L Wanner, Hirotada Mori. 2006. Construction of *Escherichia coli* K-12 in-frame, single-gene knockout mutants: the Keio collection. Molecular Systems Biology 2.
16. Lee T S, Krupa R A, Zhang F, Hajimorad M, Holtz W J, Prasad N, Lee S K, Keasling J D. 2011. BglBrick vectors and datasheets: A synthetic biology platform for gene expression. J Biol Eng 5:12.
17. Studier W. 2005. Protein production by auto-induction in high-density shaking cultures. Protein Expression and Purification 41:207-234.
18. Zhang W, Heemstra J R, Jr., Walsh C T, Imker H J. 2010. Activation of the pacidamycin PacL adenylation domain by MbtH-like proteins. Biochemistry 49:9946-9947.
19. Zhang W, Tang Y. 2009. Chapter 16 In Vitro Analysis of Type II Polyketide Synthase. 459:367-393.
20. Gregory Bokinsky EEKB, Swetha Akella, Helcio Burd, Daniel Weaver, Jorge Alonso-Gutierrez, Héctor Garcia-Martin, Taek Soon Lee, Jay D. Keasling. 2013. HipA-Triggered Growth Arrest and β-Lactam Tolerance in *Escherichia coli* Are Mediated by RelA-Dependent ppGpp Synthesis. Journal of Bacteriology 195:3173-3182

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

Example 1

Application of an Acyl-CoA Synthetase from *Streptomyces aizunensis* for Lactam Biosynthesis ε-caprolactam and δ-valerolactam are important commodity chemicals used in the manufacture of nylons, with millions of tons produced every year. Biological production of these high valued chemicals has not been possible due to a lack of enzymes that will cyclize the ω-amino fatty acid precursors to the corresponding lactams under ambient conditions. In this study, we demonstrated proof of these bioconversions by in vitro enzyme assays. We found that ORF27, an enzyme involved in the biosynthesis of ECO-02301 in *Streptomyces aizunensis*, has a broad substrate spectrum and can not only cyclize γ-aminobutyric acid into butyrolactam, but also 5-aminovaleric acid (5-AVA) into 6-valerolactam and 6-aminohexanoic acid (6-AHA) into ε-caprolactam. The ORF27 lactam formation reaction was characterized by product analysis, and ORF27's activity on the three ω-amino fatty acids were compared. Recombinant *E. coli* expressing ORF27 produced valerolactam and caprolactam when 5-AVA and 6-AHA, respectively, were added to the culture medium. Upon co-expressing ORF27 with a metabolic pathway that produced 5-aminovaleric acid from lysine, we were able to demonstrate production of 6-valerolactam from lysine or directly from glucose.

In this study, we overexpressed ORF27 in *Escherichia coli* and purified it by affinity chromatography. This enabled us to explore the catalytic properties of this enzyme. ORF27 was confirmed to possess 4-guanidinylbutyryl-CoA ligase (4GBL) activity. ORF27 had broad substrate specificity: it could act on linear or branched acid substrates with positively charged or neutral functional groups on the ω-terminal end, yet the enzyme was selective against negatively charged groups on the substrate's ω-terminal end. Intriguingly, ORF27's activity for w-amino fatty acids activation led to its application as a general lactam synthase, enabling biosynthesis of caprolactam, valerolactam and butyrolactam. Comparative study of ORF27's reaction products for different w-amino fatty acid precursors was performed to better understand this enzyme's activity as a lactam synthase.

To apply ORF27 for renewable chemical production, ORF27 was overexpressed in *E. coli*, and both valerolactam and caprolactam were formed in vivo by feeding their respective precursors, 5-aminovaleric acid (5-AVA) and 6-aminohexanoic acid (6-AHA). To achieve renewable production of valerolactam from sugar, we introduced a two-gene pathway into *E. coli* that converts lysine to 5-AVA. The pathway contains an L-lysine monoxygenase (davB from *Pseudomonas putida* KT2440) and a 5-aminovaleramide amidohydrolase (davA from *Pseudomonas putida* KT2440). Introducing the genes encoding the 5-AVA biosynthetic pathway and a gene encoding a fusion of ORF27 with maltose binding protein, MBP-ORF27, enabled *E. coli* to produce valerolactam from lysine or directly from glucose.

Materials and Methods

Strains and Plasmids.

All the strains and plasmids utilized in this study are listed in Table 1. The sequences for the plasmids are listed herein.

TABLE 1

*E. coli* strains, plasmids and oligonucleotides used.

| Name Host Strains | Relevant genotype | Reference |
|---|---|---|
| DH10B | F⁻ mcrA Δ(mrr-hsdRMS-mcrBC) φ80lacZΔM15 ΔlacX74 recA1 endA1 araD139 Δ(ara, leu)7697 galU galK λ⁻ rpsL nupG | Life Technologies (Carlsbad, CA) |
| BL21 Star (DE3) | F⁻ ompT hsdSB (rB⁻ mB⁻) gal dcm rne131 (DE3) | Life Technologies (Carlsbad, CA) |
| JW2637-4 | F-, Δ(araD-araB)567, ΔlacZ4787(::rrnB-3), λ⁻, ΔgabT743::kan, rph-1, Δ(rhaD-rhaB)568, hsdR514 | CGSC #11775 |

| Engineered Strains | plasmids | Host |
|---|---|---|
| JZ-171 | pBbE2C-ORF27 | JW2637-4 |
| JZ-172 | pBbE2C-RFP | JW2637-4 |
| JZ-440 | pBbA7a-DavB-DavA | BL21(DE3) star |
| JZ-441 | pBbA7a-DavB-DavA + pET28a-MBP-ORF27 | BL21(DE3) star |

| Constructed Plasmid | Backbone Source (restriction site) | Gene Source (direct digestion or PCR) | PCR primers |
|---|---|---|---|
| pBbE2C-ORF27 | pBbE2C-RFP (BglII, XhoI) | pDNA2.0-ORF27 (BglII, XhoI) | N/A |
| pET28b-N-ORF27 | pET28b (NdeI, XhoI) | pDNA2.0-ORF27 (NdeI, XhoI) | N/A |
| pET28b-C-ORF27 | pET28b (NcoI, XhoI) | pDNA2.0-ORF27 PCR | JZ_27_C6xHis_f, JZ_27_C6xHis_r |
| pET28a-MBP-ORF27 | pET28a-MBP (NdeI, XhoI) | pDNA2.0-ORF27 (NdeI, XhoI) | N/A |
| pBbA7a-DavB-DavA | pBbA7a-RFP (BglII, XhoI) | DavB, DavA gBlock | N/A |

TABLE 1-continued

*E. coli* strains, plasmids and oligonucleotides used.

| Oligonucleotides | 5'→ 3' Sequence, restriction site underlied, synthesized by Integrated DNA Technologies, Inc (Coralville, IA) | Target Gene |
|---|---|---|
| JZ_27_C6xHis_f | GCGCGccatgg gc ATGCGCCCAATGACCGCTAAAATCTTCG (SEQ ID NO: 11) | C-6xHis-ORF27 |
| JZ_27_C6xHis_r | GCGCGctcgagTTCTGCCGCCATACGGGTCAGC (SEQ ID NO: 12) | C-6xHis-ORF27 |

ORF27 Protein Expression and Purification.

The gene encoding ORF27 (GenBank: AAX98201.1) was purchased from DNA 2.0 (Menlo Park, Calif.). The synthetic gene was optimized with *E. coli* codon usage and delivered in pDNA2.0-ORF27. For expression and purification of ORF27, the pDNA2.0-ORF27 plasmid was digested with NdeI and XhoI and cloned into pET28b in order to produce ORF27 with an N-terminal 6xHis tag. The resulting plasmid, pET28b-N-ORF27, was transformed into *E. coli* BL21 Star (DE3) for ORF27 overexpression. To place a C-terminal His-tag on ORF27, primers JZ_27_C6xHis_f and JZ_27_C6xHis_r were used to amplify ORF27 from pDNA2.0-ORF27. The resulting PCR product was digested with NcoI and XhoI and cloned into pET28b.

For N-terminal 6xHis ORF27 expression, the overnight culture was inoculated (1:100 v/v) into 1 L LB medium containing 5 µg/ml kanamycin. The culture was grown at 37° C. until the O.D. reached 0.6 and cooled on ice for 20 min. 0.5 mM IPTG was added to induce N-6xHis ORF27 overexpression for 16 h at 18° C. The cells were harvested by centrifugation (8000×g, 6 min, 4° C.), resuspended in 30 mL of lysis buffer (50 mM HEPES, pH 8.0, 0.5 M NaCl, and 10 mM imidazole), and lysed by sonication on ice. Cellular debris was removed by centrifugation (20,000×g, 30 min, 4° C.). Ni-NTA agarose resin was added to the supernatant (1 mL/L of culture), and the solution was rocked at 4° C. for 1 h. The protein resin mixture was loaded onto a gravity flow column, and proteins were washed with washing buffer (50 mM HEPES, pH 8.0, 0.5 M NaCl, and 20 mM imidazole) and eluted with elution buffer (50 mM HEPES, pH 8.0, 0.5 M NaCl, and 250 mM imidazole). Purified proteins (60 mg from 1 L culture) were concentrated to 280 mg/mL and buffer exchanged into storage buffer (50 mM HEPES, pH 8.0, 8% glycerol). The final proteins were aliquoted and flash frozen in liquid nitrogen and stored at −80° C. C-terminal 6xHis ORF27 (65 mg/L LB culture) was produced using BL21 Star (DE3) transformed with pET28b-C-ORF27, purified by Ni-NTA agarose resin and stocked at 220 mg/mL in storage buffer (50 mM HEPES, pH 8.0, 8% glycerol).

Figure 4:
FIG. 4. SDS-PAGE of ORF27 purified from *E. coli*. Ready gel for Tris-Glycine Gel (10% precast, Bio-Rad) was used. For molecular weight determination, PageRuler™ Prestained Protein Ladder (10 to 180 kDa, ThermoFisher Scientific) was used as protein ladder.

Nickel nitrilotriacetic acid agarose (Ni-NTA) resin and SDS-PAGE gels were purchased from Qiagen and Biorad, respectively. Protein samples were concentrated using 10 KDa MMCO Amicon Ultra filters (Millipore). DNA and protein concentrations were determined using a Nanodrop 1000 spectrophotometer (Thermo Scientific). The purified ORF27 was checked on SDS-PAGE gel for purity (FIG. 4).

ATP-PPi Release Assays for ORF27.

The substrate range of ORF27 was determined by ATP-PPi release assays as previously described (12). Without prior knowledge about the reaction pathways, the ATP-PPi assay served a semi-quantitative method to compare substrate induced acceleration of ATP consumption. For kinetic investigation of ORF27 activity with different substrates, the inorganic pyrophosphate released by enzymatic reaction was measured continuously using the EnzChek Pyrophosphate Assay Kit (Invitrogen). A typical assay contained in a total volume of 150 µL: 5 µM of ORF27, 0-20 mM substrates, 1 mM ATP, 1 mM CoASH and 1 mM Mg(Cl)$_2$ in 100 mM HEPES, pH 7.5. 2-amino-6-mercapto-7-methylpurine ribonucleoside (MESG) substrate, purine nucleoside phosphorylase and inorganic pyrophosphatase were added according to the protocol. Reactions were initiated by the addition of ATP and monitored at 360 nm with SpectraMax M2 (Molecular Devices, Sunnyvale, Calif.). Initial velocities were calculated using the standard curve for inorganic pyrophosphate. For each concentration, control reactions were carried out without enzyme or without ATP. The rates of PPi release were converted to observed rates, and the Michaelis-Menten kinetic parameters were obtained.

The acids assayed were glutamic acid, γ-aminobutyrate (GABA), 4-guanidinobutyric acid, (S)-3-hydroxyl-butyric acid, valeric acid, 4-methyl-hexanoic acid, 3-aminobutyric acid, 6-aminocaproic acid, 6-guanidinohexanoic acid, glutaric acid, adipic acid, 2-aminobutyric acid and (Sigma-Aldrich, St. Louis, Mo.). During preparation of substrate stock solution, 6-guanidinohexanoic acid has low solubility under neutral pH, and HCl was added to obtain 100 mM stock solution in pH ~2.0.

4-Guanidinobutyryl CoA Product Identification.

To confirm ORF27's native activity as a 4-guanidinobutyryl CoA synthetase, the quenched reaction with 4-guanidinobutyric acid was analyzed for CoA products as described previously (14). The mass measurements were carried out in the TOF-Scan monitoring mode for the detection of [M−H]$^-$ ions (4-guanidinobutyrl-CoA, m/z=893.1825). Negative controls were carried out using no enzyme, no ATP, no substrate or no CoASH.

Product Analysis of In Vitro ORF27 Lactam Formation.

To compare formation of various lactams by ORF27, a reaction mixture containing 57 M of ORF27, 5 mM ω-amino fatty acids substrates, 1 mM ATP or ADP, 0.5 mM CoASH and 1 mM Mg(Cl)$_2$ in 100 mM HEPES (pH=8) was incubated at 25° C. The reactions were quenched by addition of methanol to a final concentration of 50% (v/v) at multiple time points (0 min, 15 min, 1 h, 2 h, 4 h and 19 h). The resulting quenched reactions were kept at 4° C. and filtered through 10 K Amicon Ultra-0.5 mL Centrifugal Filters (Millipore) at 8000×g for 30 min. The filtered solutions were analyzed for lactams and nucleotides using HPLC-MS. Control reactions were carried out without enzyme, without substrate, without ATP, without CoASH or without MgCl$_2$ (supplying additional 0.2 mM EDTA to chelate Mg$^{2+}$ ions from purified protein stock). Caprolactam, valerolactam and butyrolactam, AMP, ADP and ATP were purchased as standards from Sigma-Aldrich. The pH dependence of ORF27-catalyzed butrylactam formation was determined using an end-point assay, and the amount of butyrolactam was determined using the HPLC-MS method described above.

Lactam Production In Vivo.

E. coli JW2637-4 contains a knockout of gabT, which encodes a GABA transaminase (15). This host was initially used to confirm production of valerolactam and caprolactam in vivo. E. coli JZ-171 (ORF27) and JZ-172 (RFP negative control) were grown in LB medium containing 1 mM 5-AVA and 6-AHA. Cultures were propagated in Luria-Bertani (LB) medium, which was prepared from dehydrated powder according to the manufacturer's instructions (BD Biosciences, San Jose, Calif.). To analyze caprolactam production, the culture was pelleted and supernatant was filtered before mixing with 1 volume of MeOH.

In Vivo Valerolactam Biosynthesis.

The davA and davB genes were ordered as gBlocks (Integrated Dna Technologies, Coralville, Iowa) and cloned into the BglII and XhoI sites on pBbA7, a biobrick vector, to generate plasmid pBbA7a-DavB-DavA(16). To circumvent ORF27's limited solubility during incubation, MBP-ORF27 was utilized (13). For high-density shake flask cultures, Studier's autoinduction ZYM-5052 medium was prepared according to the published protocol (17). Lysine at various concentrations (0 g/L, 1 g/L, 5 g/L and 10 g/L) was included in the ZYM-5052 medium. Kanamycin (20 μg/ml) and ampicillin (100 μg/ml) were added where desired to provide selective pressure for plasmid maintenance.

E. coli strains (JZ-441) harboring plasmids containing genes encoding davA, davB and MBP-ORF27 were inoculated into 10 mL of LB overnight. On day 2, the overnight culture was inoculated 1:100 (v/v) into 25 mL Studier's autoinduction ZYM-5052 medium with various concentrations of lysine (0 g/L to 10 g/L) and appropriate antibiotics (17). The culture was incubated at 37° C. When the O.D. reached around 0.6, the culture was cooled to 25° C. The culture was then placed at 25° C. incubator and the valerolactam titer was analyzed at 24 h, 48 h and 72 h. JZ-440, which contains only davA and davB, served as a negative control.

Caprolactam, Valerolactam and Butyrolactam Analytical Method

Liquid chromatography (LC) separation of lactams were conducted at 55° C. with an Inertsil ODS-3 reverse-phase C18 column (250 mm length, 2.1 mm internal diameter, 3 M particle size; GL Sciences) using a 1100 series high-performance LC system (Agilent Technologies). The mobile phase was composed of 0.1% formic acid in $H_2O$ (solvent A) and 0.1% formic acid in MeOH (solvent B). Butyrolactam was separated with the following gradient: 40% to 60% B for 4.5 min, 60% to 100% B for 0.5 min, 100% to 40% B for 0.5 min, held at 10% B for 8.5 min. A flow rate of 0.18 mL/min was used throughout.

Time-of-Flight Mass Spectrometry Method for Lactam Accurate Mass Monitoring

The LC system was coupled to an Agilent Technologies 6210 electrospray time-of-flight (TOF) mass spectrometer. Nitrogen gas was used as both the nebulizing and drying gas to facilitate the production of gas-phase ions. The drying and nebulizing gases were set to 11 L/min and 25 psig, respectively, and a drying gas temperature of 320° C. was used throughout. ESI was conducted in the positive-ion mode with a capillary voltage of 3.5 kV. Mass measurements were carried out in the TOF-Scan monitoring mode for the detection of $[M+H]^+$ ions (2-pyrrolidone, m/z=86.0600; 2-piperidinone, m/z=100.07569; caprolactam, m/z=114.09134). The instrument was tuned for a range of m/z 70 to 300. Data acquisition and processing were performed using MassHunter Workstation (Agilent Technologies).

ATP, ADP, AMP Analytical Method

Nucleotide product analysis studies was analyzed using an expedited modification of the HILIC method previously described (20). Liquid chromatography (LC) separation of lactams were conducted at 40° C. with an SeQuant Zic-pHILIC column (150 mm length, 2.1 mm internal diameter, 5 μM particle size; GL Sciences) using a 1100 series high-performance LC system (Agilent Technologies). The mobile phase was composed of 50 mM $(NH_4)_2CO_3$ in $H_2O$ (solvent A) and acetonitrile (solvent B). ATP, ADP, AMP and CoAs were separated with the following gradient: 73% to 43% B for 6 min (flow rate 0.25 mL/min), 43% to 73% B for 0.2 min (flow rate 0.25 mL/min), hold at 73% B for 1 min (flow rate 0.3 mL/min), hold at 73% 0.2 min (flow rate 0.3 mL/min), held at 73% B for 5.1 min (flow rate of 0.38 mL/min). The HPLC system was coupled to TOF MS. ESI was conducted in the negative ion mode, and a capillary voltage of 3.5 kV was utilized. Fragmentor, skimmer, and OCT1 RF voltages were set to 200 V, 65 V, and 300 V, respectively. Mass measurements were carried out in the TOF-Scan monitoring mode for the detection of $[M-H]^-$ ions (ATP, m/z=505.9885; ADP, m/z=426.0221; AMP, m/z=346.0558; CoASH, m/z=766.1079). MS experiments were carried out in the full-scan mode (m/z 100 to 1000).

ORF27 Biochemistry and Implications on ECO-02301 Loading Mechanism

By exploring its substrate specificity, 4-guanidinobutyric acid is confirmed to be its natural substrate. This is consistent with previous hypothesis that ECO-02301 biosynthesis uses 4-guanidinobutyric acid as a starter unit. The inability to isolate activated 4-aminobutyryl esters in the enzymatic reaction showed the transient nature of the intermediate. This suggests that the proposed amidinohydrolase (ORF33) in the gene cluster may hydrolyze the ureido group later during ECO-02301 biosynthesis rather than before loading onto the first ACP domain.

Results

ORF27 Biochemistry.

The sensitivity of the ATP-PPi release assay (5 μM Pi) allowed the initial velocity to be determined within the first 2 min of reaction incubation. During this time period, ATP hydrolysis activity by ORF27 was not observed according to the ATP-PPi assay (ATP hydrolysis was observed over longer period of time though, see discussion below). The ATP-PPi release assay revealed that ORF27 has a broad substrate specificity. The $K_m$ and $k_{cat}$ values of various substrates activation are shown in Table 2.

TABLE 2

Steady State Parameters of ORF27[a]

| Substrate | Structure | Product[b] | $K_m$ (mM) | $k_{cat}$ (min$^{-1}$) | $k_{cat}/K_m$ ($M^{-1}min^{-1}$) |
|---|---|---|---|---|---|
| γ-Amino-butyrate | 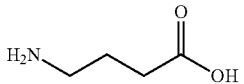 | 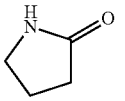 | 17.2 | 0.35 | 20.26 |

TABLE 2-continued

Steady State Parameters of ORF27[a]

| Substrate | Structure | Product[b] | $K_m$ (mM) | $k_{cat}$ (min$^{-1}$) | $k_{cat}/K_m$ (M$^{-1}$min$^{-1}$) |
|---|---|---|---|---|---|
| 4-Guanidinobutyric acid | [structure] | [structure] | 0.013 | 0.12 | 9434 |
| Glutamate[c] | [structure] | ND | ND | ND | ND |
| (S)-3-hydroxylbutyric acid | [structure] | ND | ND | ND | ND |
| Valeric acid | [structure] | [structure] | 52.2 | 1.70 | 32.6 |
| 4-Methylhexanoic acid | [structure] | [structure] | 12.1 | 1.3 | 107.8 |
| 3-Aminobutyric acid | [structure] | ND | ND | ND | ND |
| 6-Aminocaproic acid | [structure] | [structure] | 0.056 | 0.17 | 2962.6 |
| 6-Guanidinohexanoic acid | [structure] | [structure] | 0.11 | 0.33 | 2939.7 |
| Glutaric acid | [structure] | ND | ND | ND | ND |
| Adipic acid | [structure] | ND | ND | ND | ND |
| 2-Aminobutyric acid | [structure] | [structure] | 1.63 | 0.036 | 22.2 |

[a]The kinetic parameters of ORF27 were determined in a 100 mM HEPES, pH 7.5 at 25° C. using the ATP-PPi release Assays
[b]Other non-product forming pathways could occur such as ATP hydrolysis or acyl-OAMP intermediate hydrolysis.
[c]ND not determined.

Figure 5A:
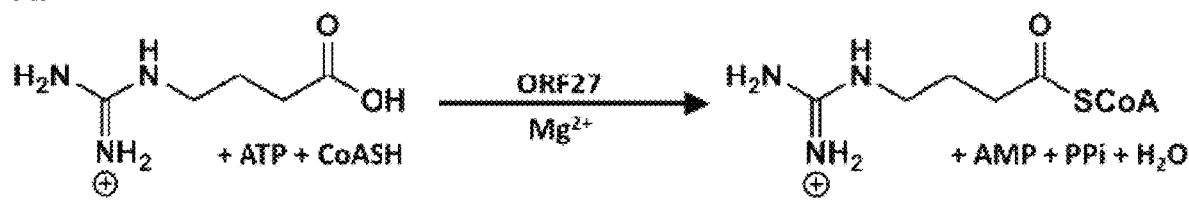
FIG. 5A. LC-MS analysis of 4-guanidinobutyrl-CoA formation catalyzed by ORF27. 4-guanidinobutyrl-CoA synthetase reaction.
Figure 5B:
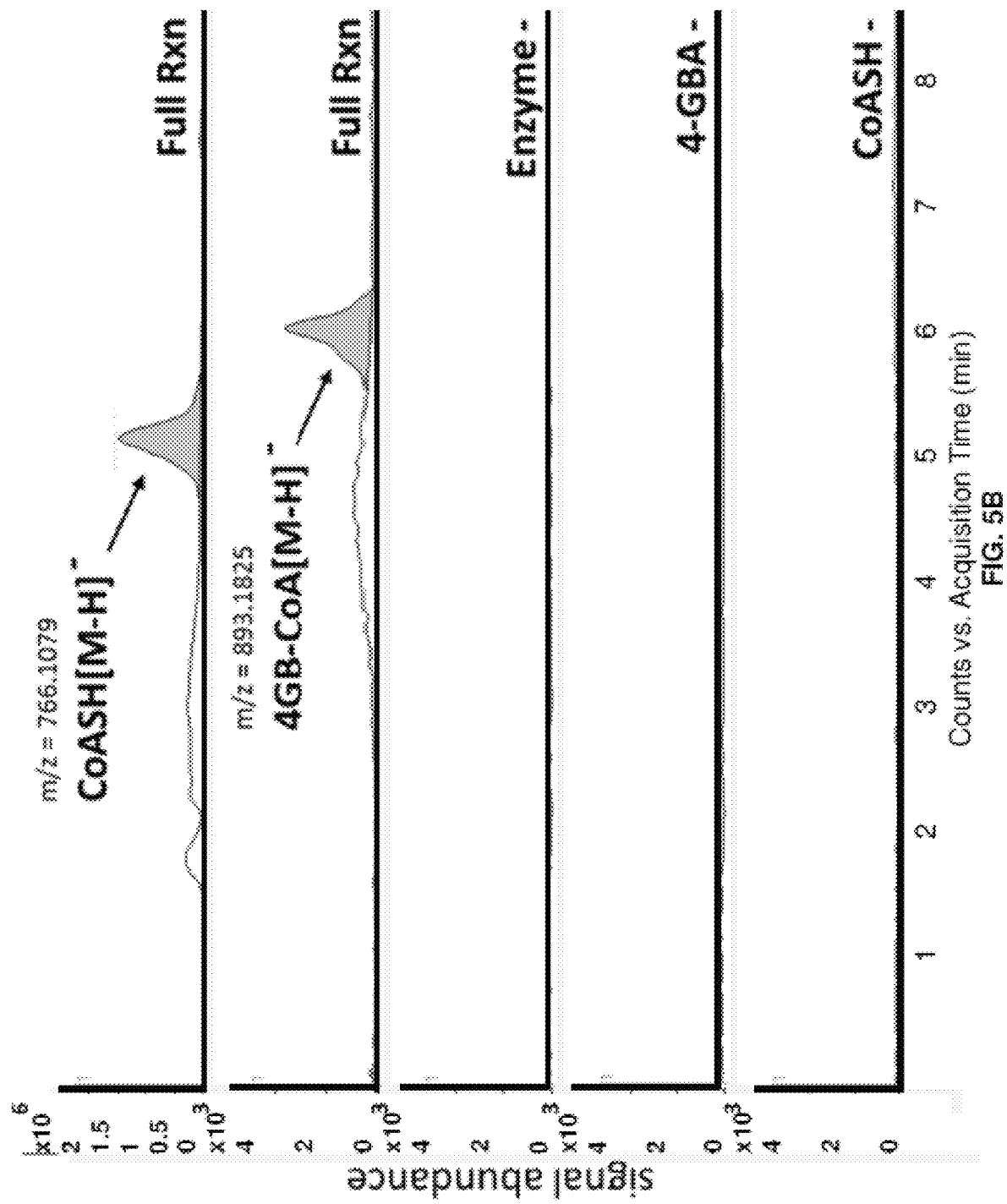
FIG. 5B. LC-MS analysis of 4-guanidinobutyrl-CoA formation catalyzed by ORF27. LC-MS confirmed that the reaction system requires ORF27, 4-guanidino butyric acid (4-GBA) and CoASH for 4-guanidinobutyryl-CoA (4 GB-CoA) product formation.

HPLC-MS confirmed that ORF27 catalyzes 4-guanidinobutyryl-CoA formation (FIGS. 5A and 5B). The ability of ORF27 to accept a broad range of substrates, especially ω-amino fatty acids, implies an interesting biotechnology application. Once the acid group of ω-amino fatty acids has been activated, amide bond formation through intramolecular cyclization is theoretically thermodynamically favored, suggesting that ORF27 might be utilized as a lactam synthase to produce industrially important chemicals, such as caprolactam, valerolactam and butyrolactam (FIG. 1).

Figure 2:
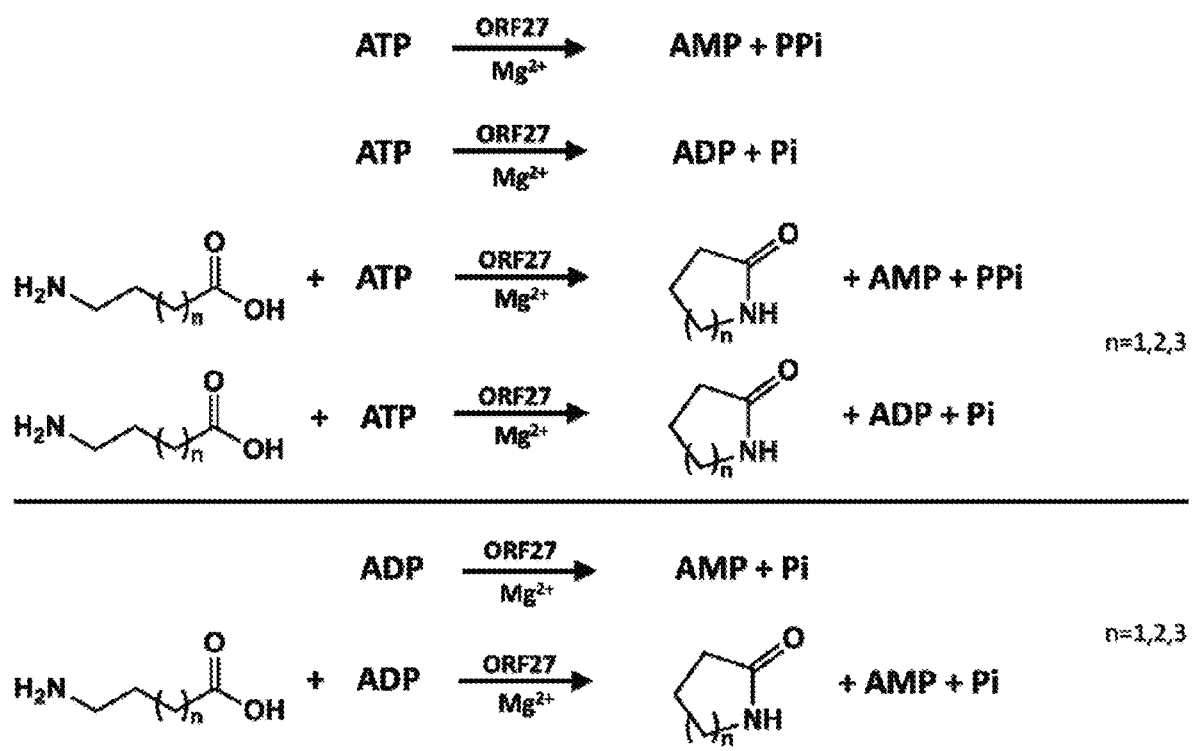
FIG. 2. ORF27 catalyzes multiple reaction pathways.
Figure 6A:
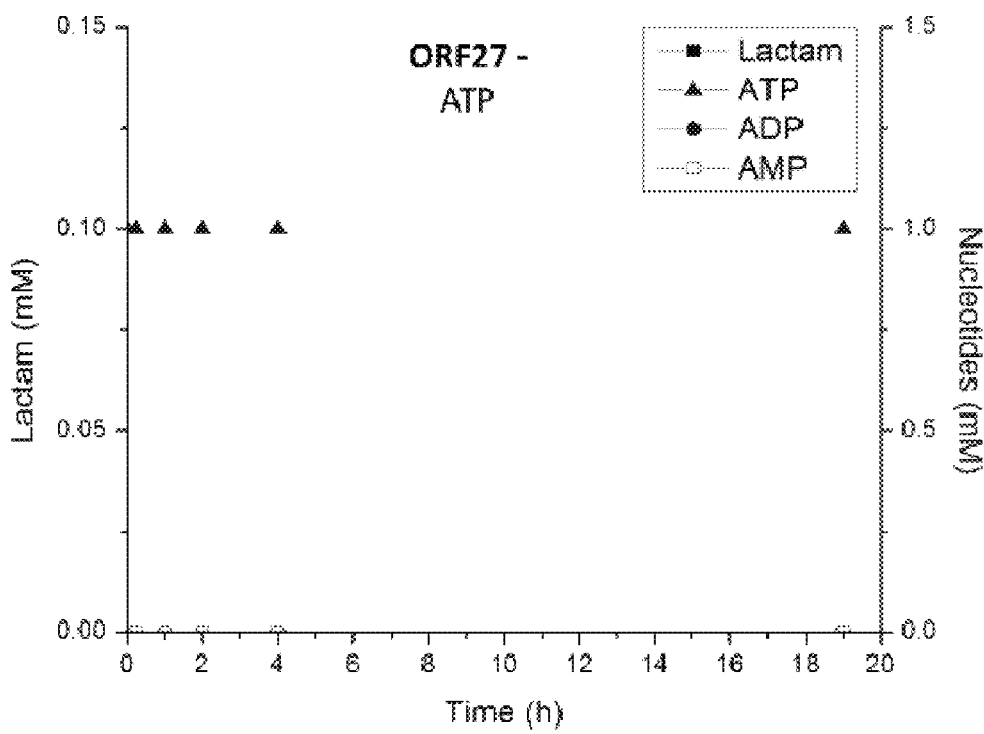
FIG. 6A. Nucleotide and lactam product analysis of ORF27 catalyzed lactam formation. ORF27 minus, ATP for activation, CoASH plus.
Figure 6B:
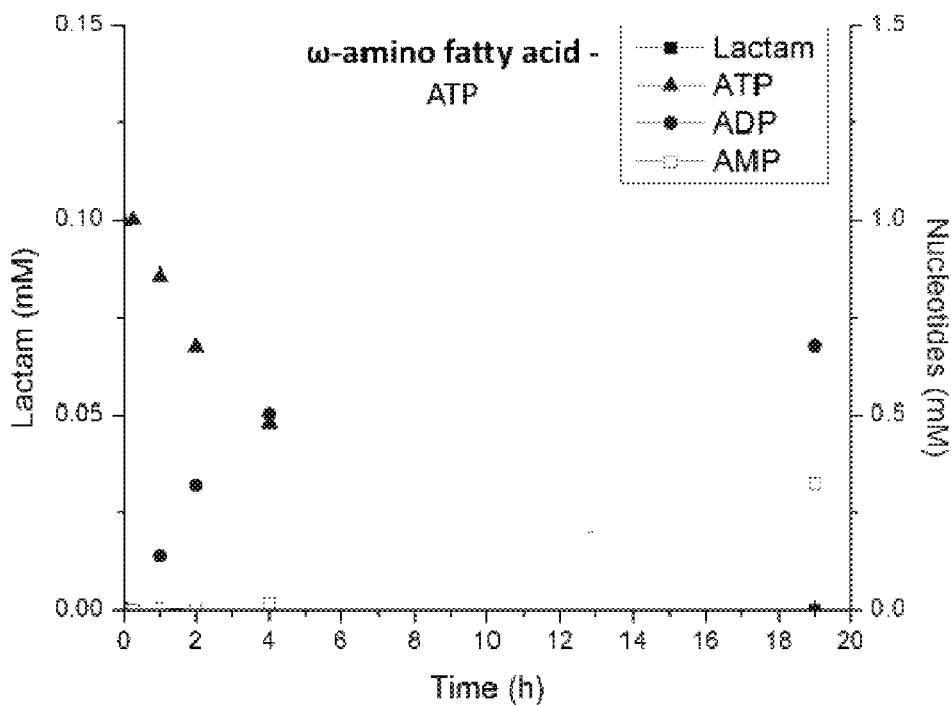
FIG. 6B. Nucleotide and lactam product analysis of ORF27 catalyzed lactam formation. ω-amino fatty acid minus, ATP, CoASH plus.
Figure 6C:
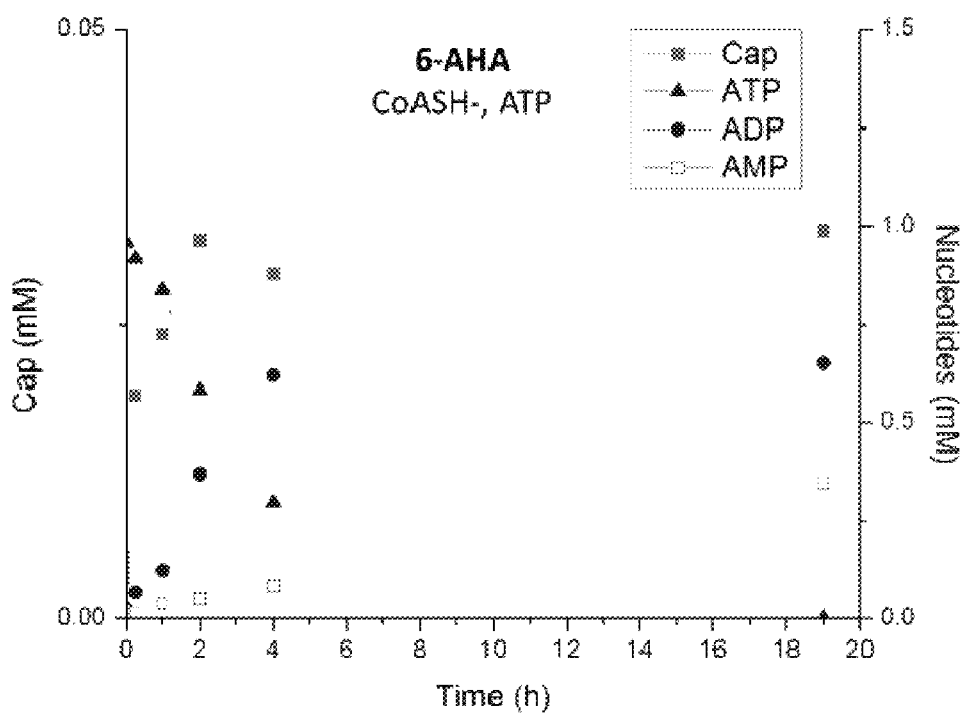
FIG. 6C. Nucleotide and lactam product analysis of ORF27 catalyzed lactam formation. 6-AHA, ATP, CoASH minus.
Figure 6D:
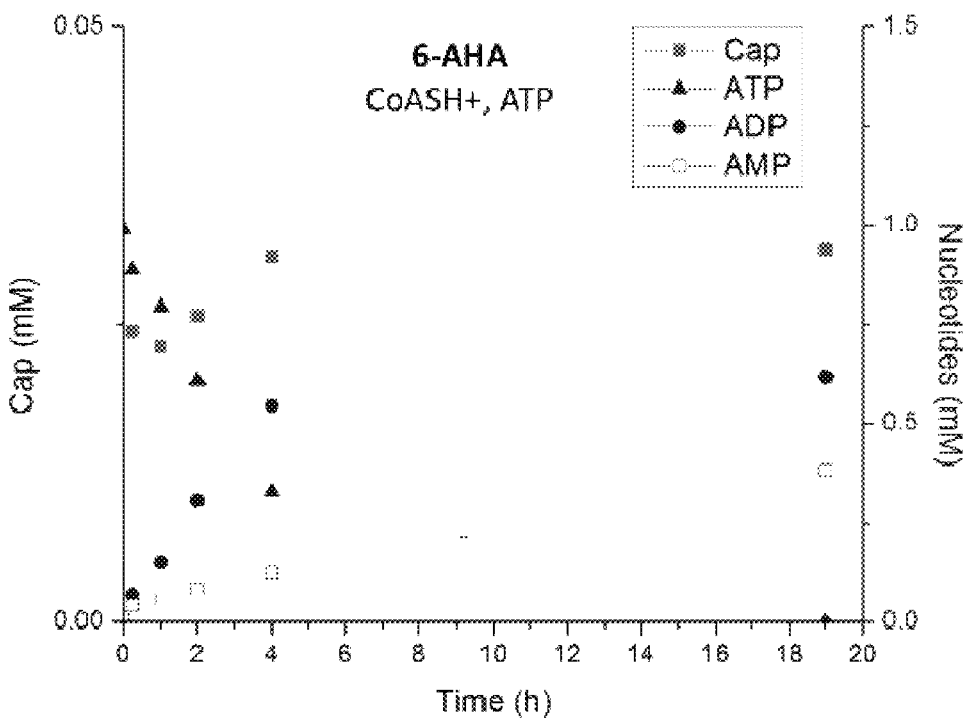
FIG. 6D. Nucleotide and lactam product analysis of ORF27 catalyzed lactam formation. 6-AHA, ATP, CoASH plus.
Figure 6E:
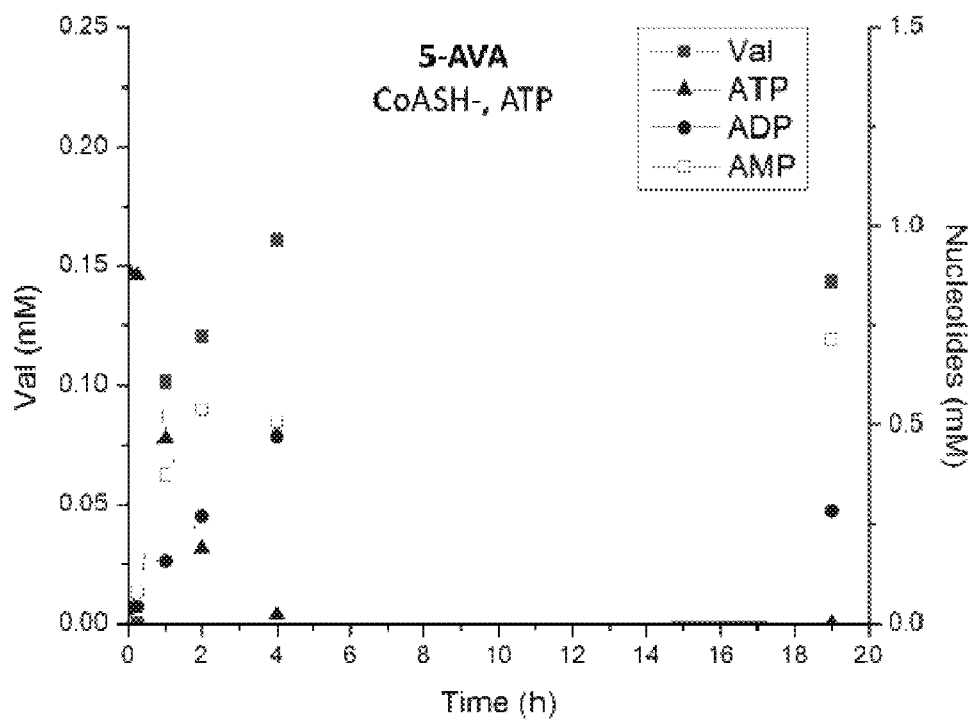
FIG. 6E. Nucleotide and lactam product analysis of ORF27 catalyzed lactam formation. 5-AVA, ATP, CoASH minus.
Figure 6F:
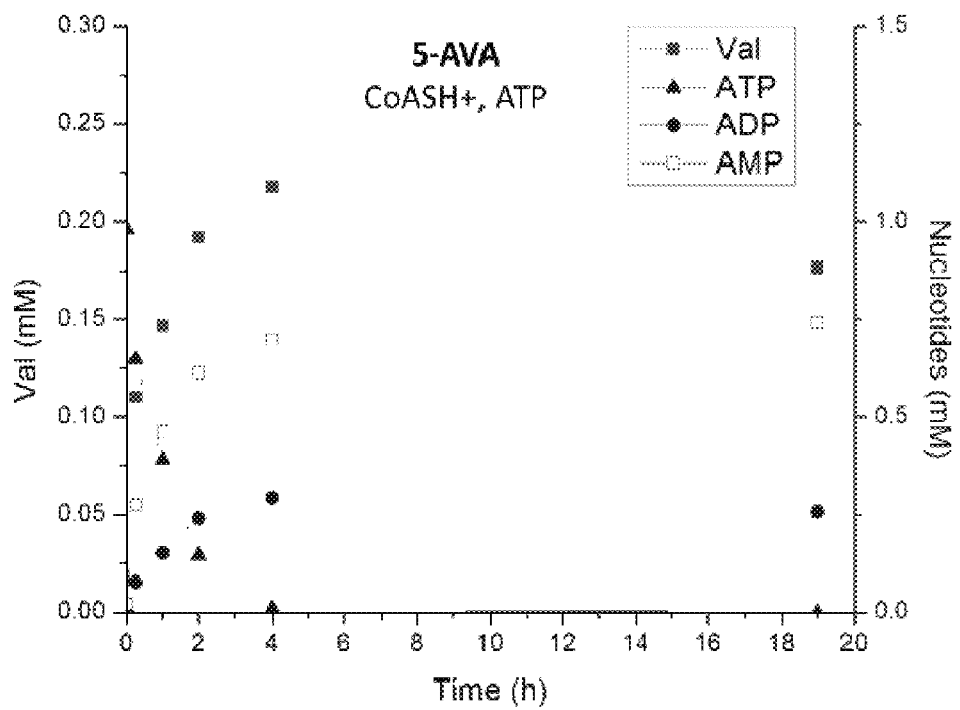
FIG. 6F. Nucleotide and lactam product analysis of ORF27 catalyzed lactam formation. 5-AVA, ATP, CoASH plus.
Figure 6G:
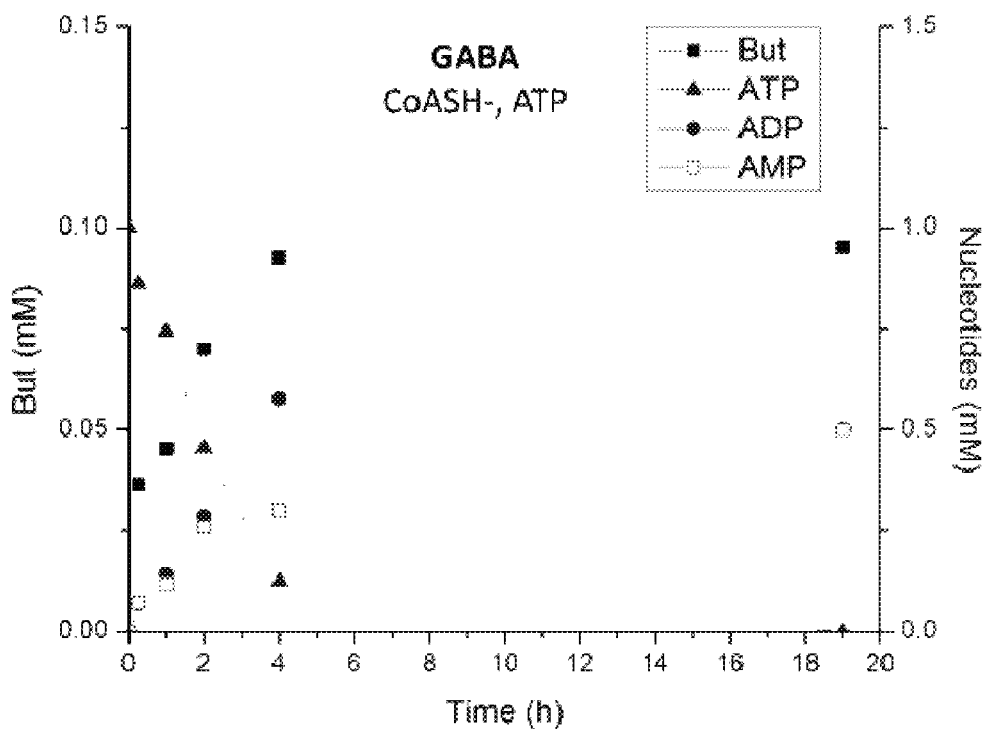
FIG. 6G. Nucleotide and lactam product analysis of ORF27 catalyzed lactam formation. GABA, ATP, CoASH minus. H) GABA, ATP, CoASH plus. I) 6-AHA, ADP, CoASH plus. J) 5-AVA, ADP, CoASH plus. K) GABA, ADP, CoASH plus.
Figure 6H:
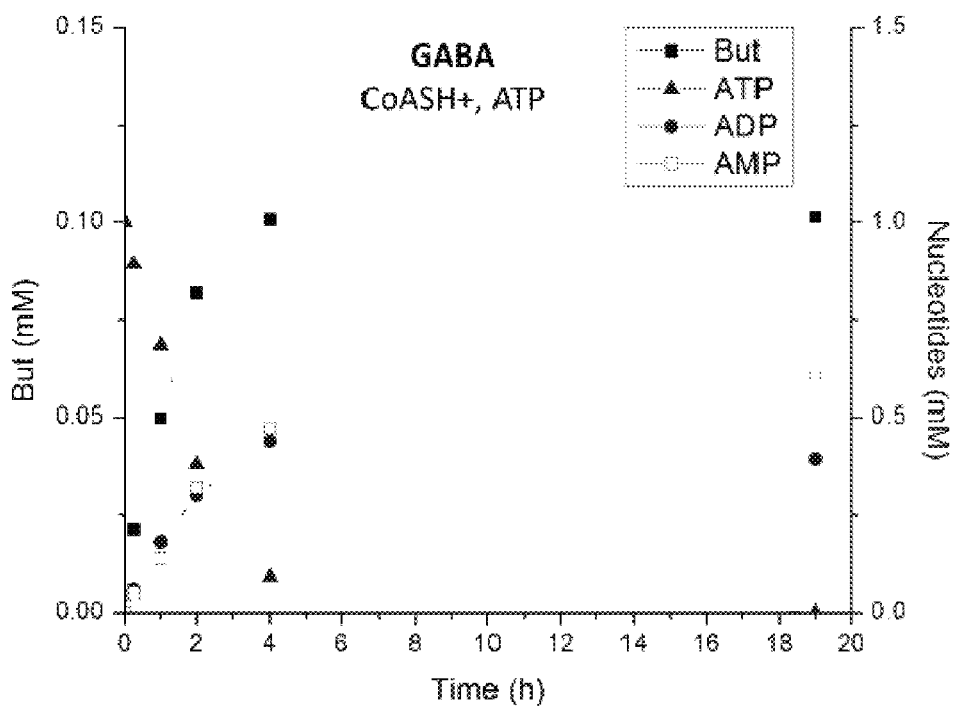
FIG. 6H. Nucleotide and lactam product analysis of ORF27 catalyzed lactam formation. GABA, ATP, CoASH plus.

The ORF27-catalyzed lactam formation reaction in vitro was monitored for both nucleotide and lactam products, using either ATP or ADP as the energy source. LC-MS analysis of nucleotides (ATP, ADP, AMP) showed that ORF27 catalyzed a series of reactions (FIG. 2). In the absence of ORF27, ATP remained stable throughout the reaction (FIG. 6A). In the absence of ω-amino fatty acids, ORF27 predominantly hydrolyzed ATP over long term incubation, forming mainly ADP plus Pi and slightly AMP and PPi (FIG. 6B). This seeming contradiction with previous negative control ATP-PPi assay result was because: due to the slow kinetics of the in vitro reaction, ATP-PPi assay was not sensitive enough to detect Pi released caused by enzymatic ATP hydrolysis into ADP and Pi during the first 2 minutes (FIG. 6B). When ω-amino fatty acids were added into the reaction mixture, they facilitate ATP hydrolysis, as well as routing hydrolysis pathway towards forming AMP and PPi rather than ADP plus Pi. Therefore, the observed signal increase in the presence of substrate for the ATP-PPi assay was due to both increased ATP consumption, and having more PPi release instead of Pi release without ω-amino fatty acid substrates.

Figure 7B:
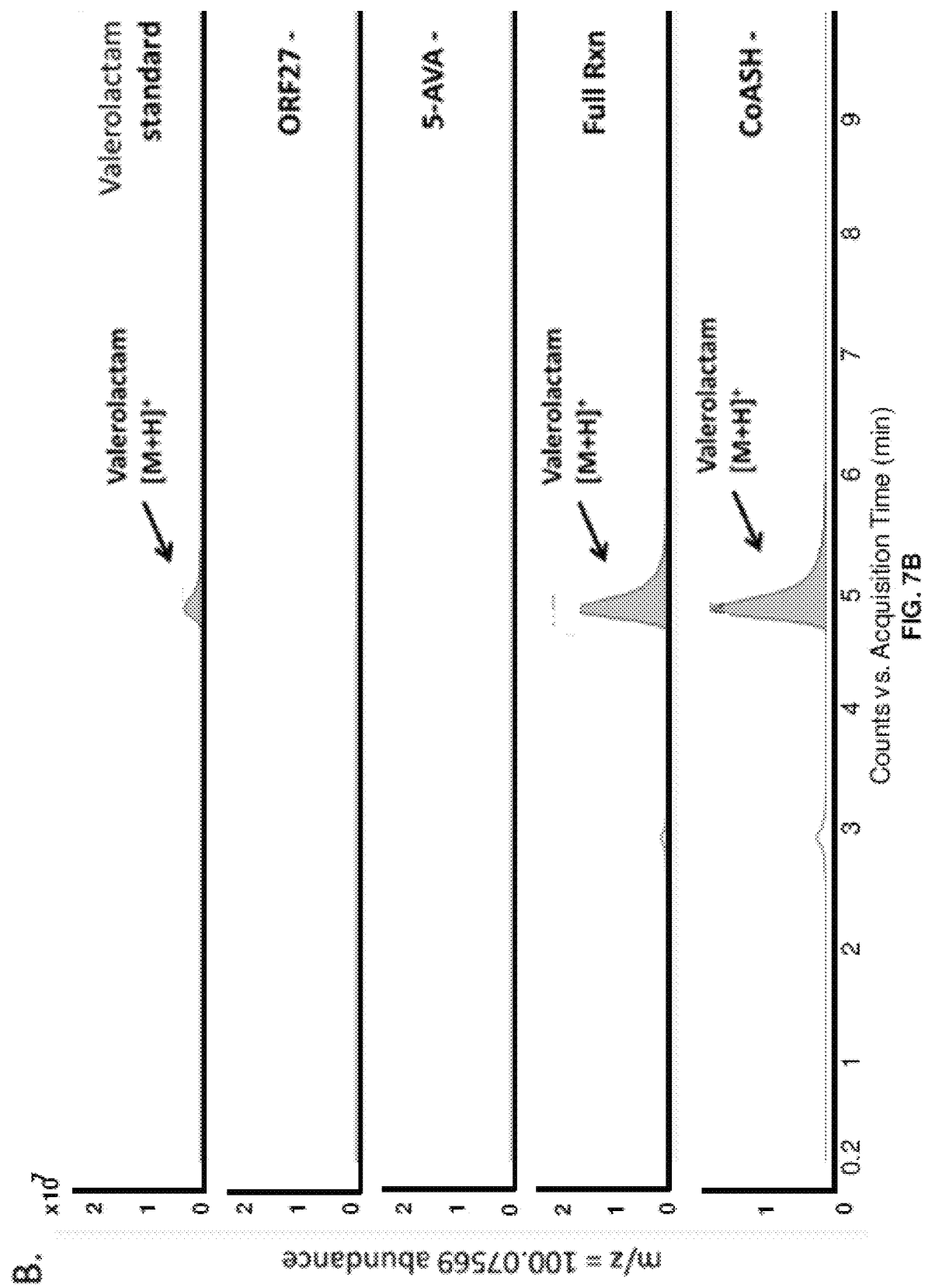
FIG. 7B. ORF27 catalyzed valerolactam formation. A reaction mixture containing 57 μM of ORF27, 5 mM w-amino fatty acids substrates, 1 mM ATP or ADP, 0.5 mM CoASH and 1 mM Mg(Cl)$_2$ in 100 mM HEPES (pH=8) was incubated at 25° C. for 19 h and quenched with methanol. The quenched reaction was filtered to get rid of protein aggregates before loading onto LC-MS.
Figure 7C:
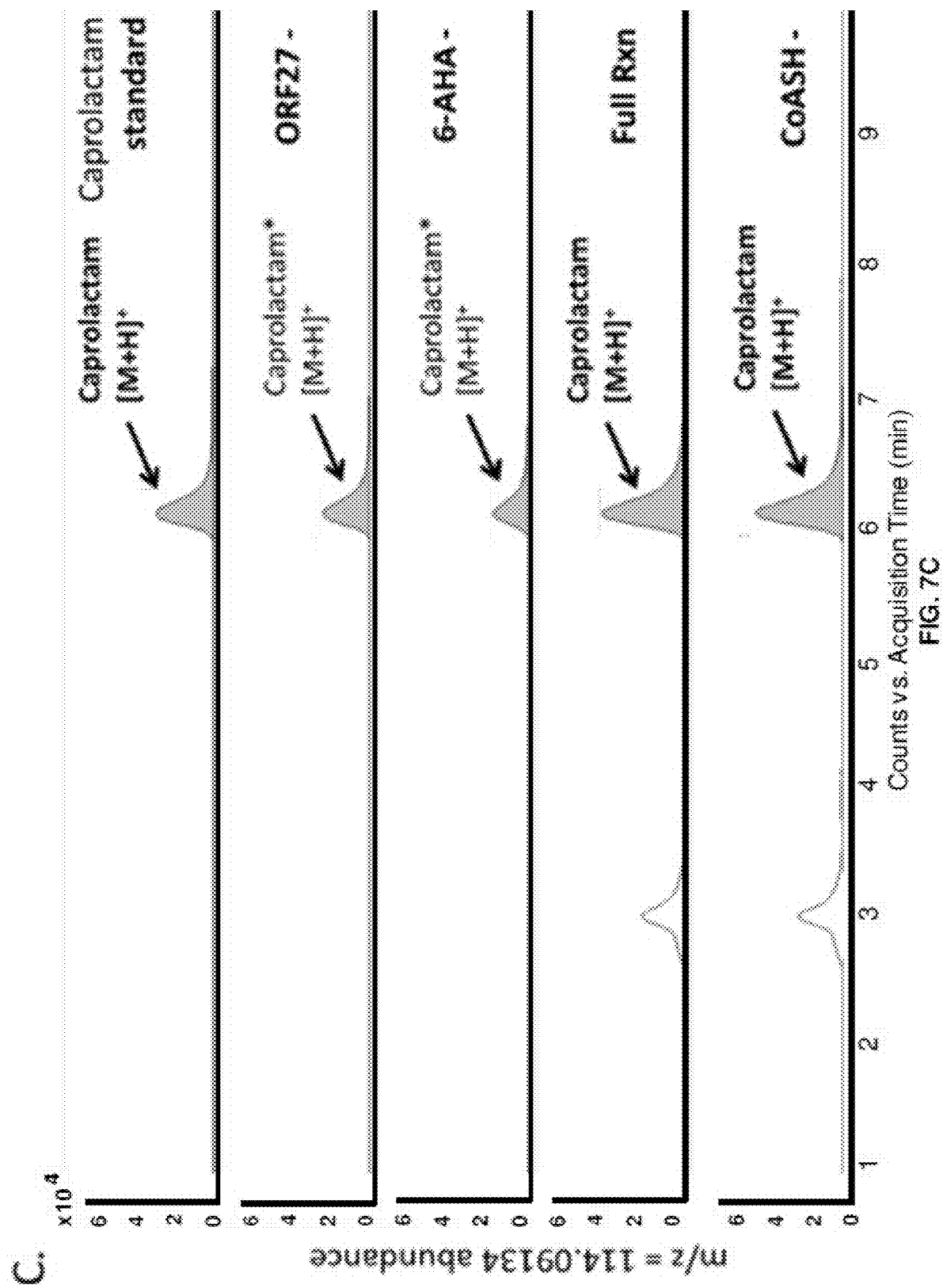
FIG. 7C. ORF27 catalyzed caprolactam formation. A reaction mixture containing 57 μM of ORF27, 5 mM co-amino fatty acids substrates, 1 mM ATP or ADP, 0.5 mM CoASH and 1 mM Mg(Cl)$_2$ in 100 mM HEPES (pH=8) was incubated at 25° C. for 19 h and quenched with methanol. The quenched reaction was filtered to get rid of protein aggregates before loading onto LC-MS.

Although ORF27 was predicted to be an acyl-CoA synthetase, CoASH was not required for lactam formation (FIGS. 6C to 6H). The minimal lactam formation system constituted w-amino fatty acids, ORF27, ATP and $Mg^{2+}$ (FIGS. 7A to 7C). Lactam formation is most rapid for valerolactam, followed by butyrolactam and caprolactam. ADP appeared earlier in in reactions containing ω-amino fatty acids but not in control reactions without the substrates, suggesting ω-amino fatty acids dependent ATP hydrolysis into ADP and Pi also occurred during the reaction.

When CoASH was added to the corresponding reactions, no 4-aminobutyryl-CoA or 5-aminovaleryl-CoA was detected and barely distinguishable 6-aminohexanoyl-CoA mass ions, corresponding to 0.6% of CoASH signal abundance, were detected (data not shown). Mass ions corresponding to other off-pathway products, such as the ω-amino fatty acids dimers or trimers, were not observed.

Figure 6I:
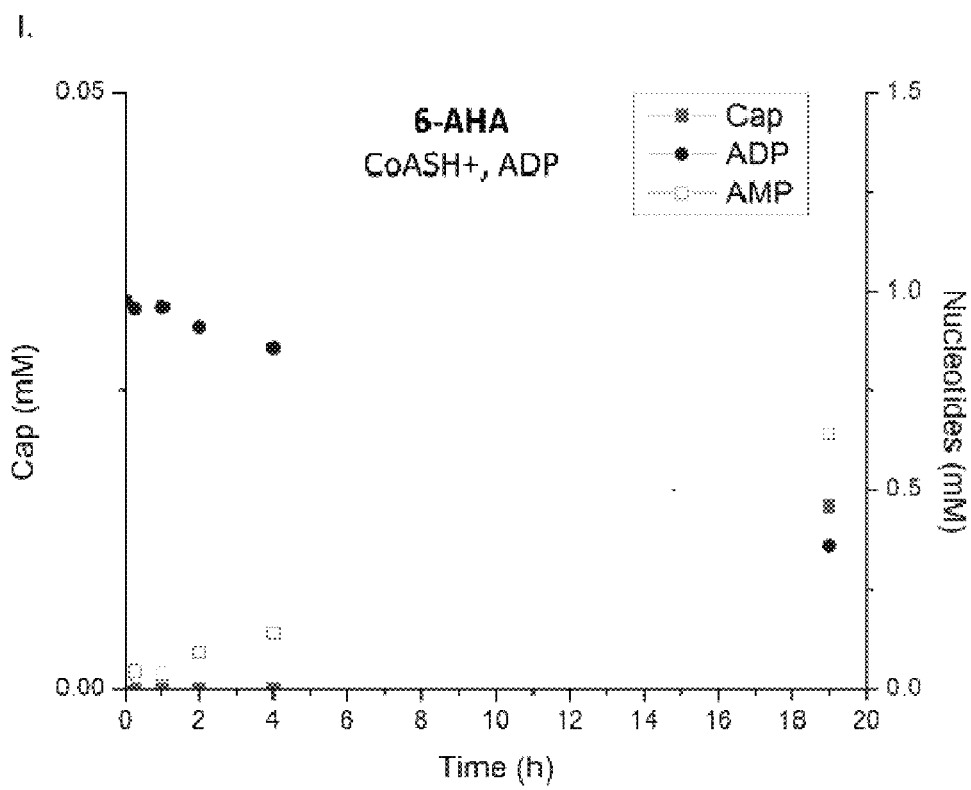
FIG. 6. Nucleotide and lactam product analysis of ORF27 catalyzed lactam formation. 6-AHA, ADP, CoASH plus.
FIG. 6J. Nucleotide and lactam product analysis of ORF27 catalyzed lactam formation. 5-AVA, ADP, CoASH plus.
FIG. 6K. Nucleotide and lactam product analysis of ORF27 catalyzed lactam formation. GABA, ADP, CoASH plus.
Figure 6J:
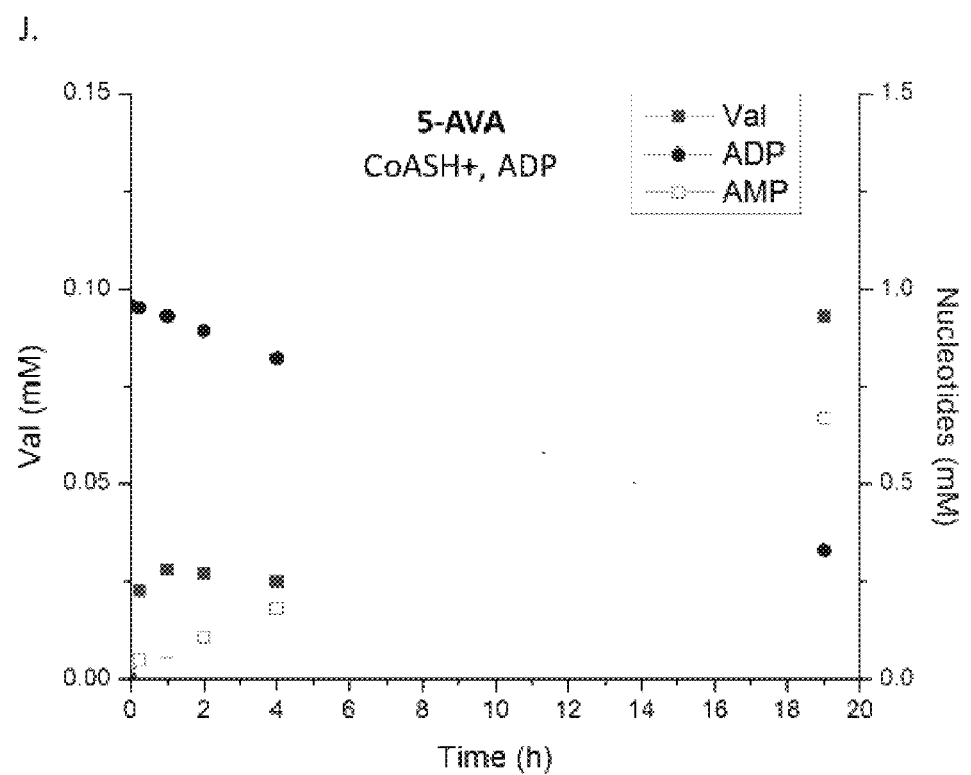
Figure 6K:
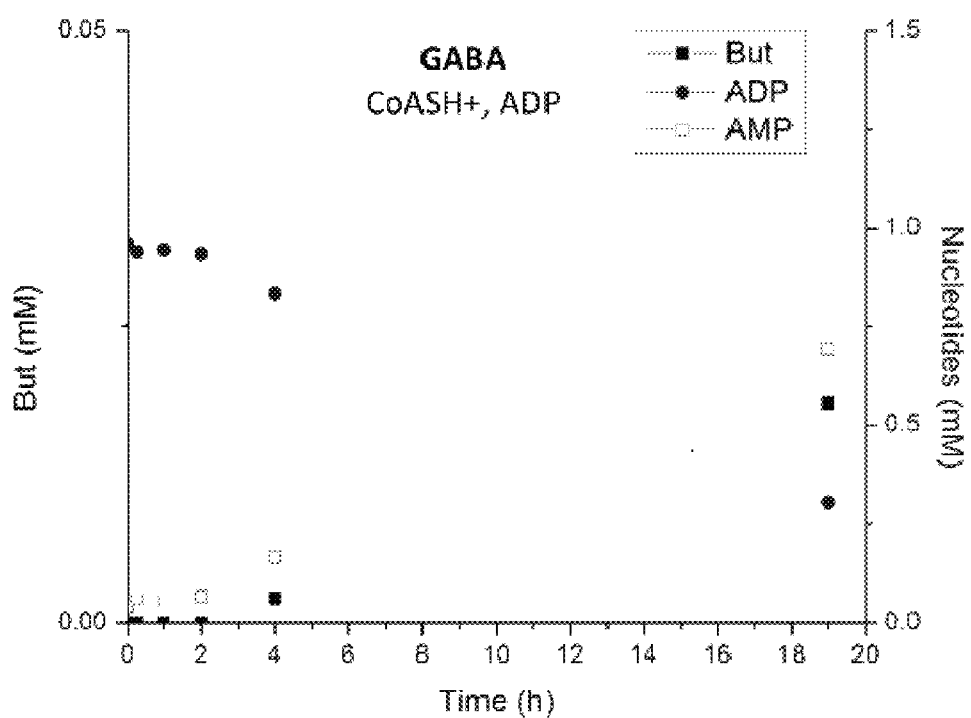

In additional to using ATP, ORF27 could also utilize ADP to activate ω-amino fatty acids and catalyze lactam formation, although the reaction occurred at only 20-50% of the rate of the similar reaction when ATP was the substrate (FIGS. 6I to 6K).

Figure 8:
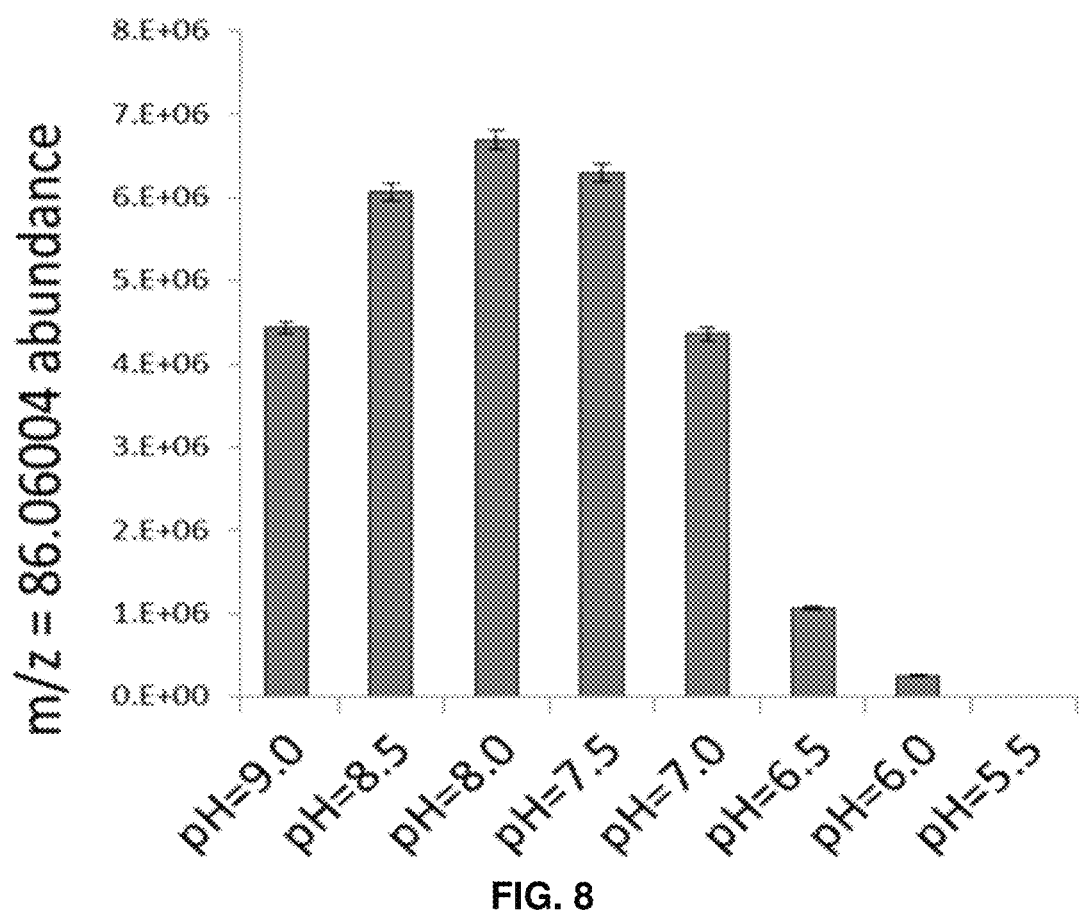
FIG. 8. pH profile of ORF27 catalyzed butyrolactam formation. A reaction mixture containing 5 µM ORF27, 1 mM GABA, 1 mM ATP, 1 mM CoASH and 1 mM $Mg(Cl)_2$ in 100 mM HEPES (pH 7.5) was incubated at 25° C. for 30 min. The reaction was quenched by equal volume of methanol, and the filtered solution was analyzed by analytical method described above.

The pH profile of ORF27 activity was determined for butyrolactam, and the enzyme had a pH optimum of 8.0. The enzyme precipitated and became inactive when the pH dropped below 6.0 (FIG. 8).

Valerolactam and Caprolactam Production In Vivo.

Figure 9A:
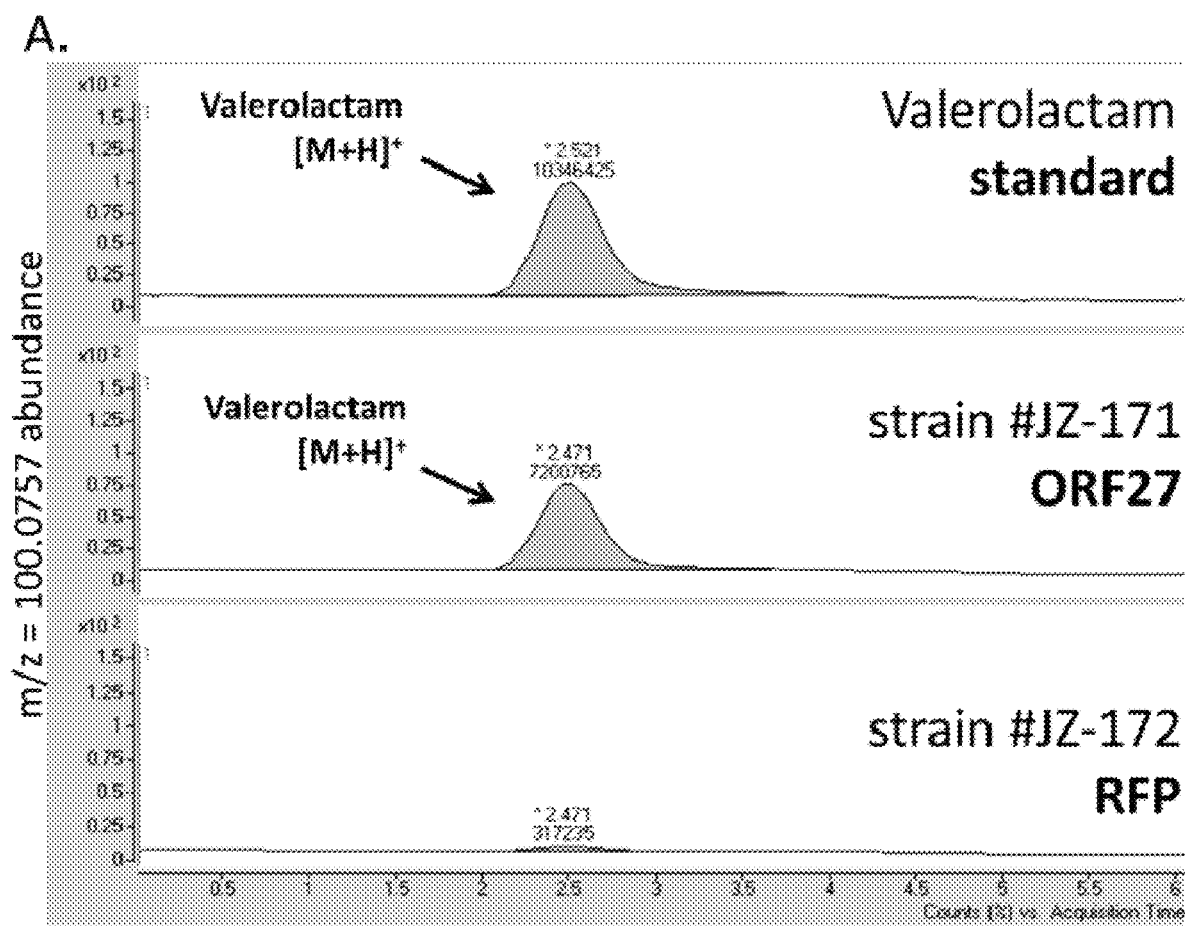
FIG. 9A. Production of industrial lactam via biosynthesis. LC-MS analysis of valerolactam production from recombinant E. coli expressing ORF27 with 1 mM 5-AVA feeding.
Figure 9B:
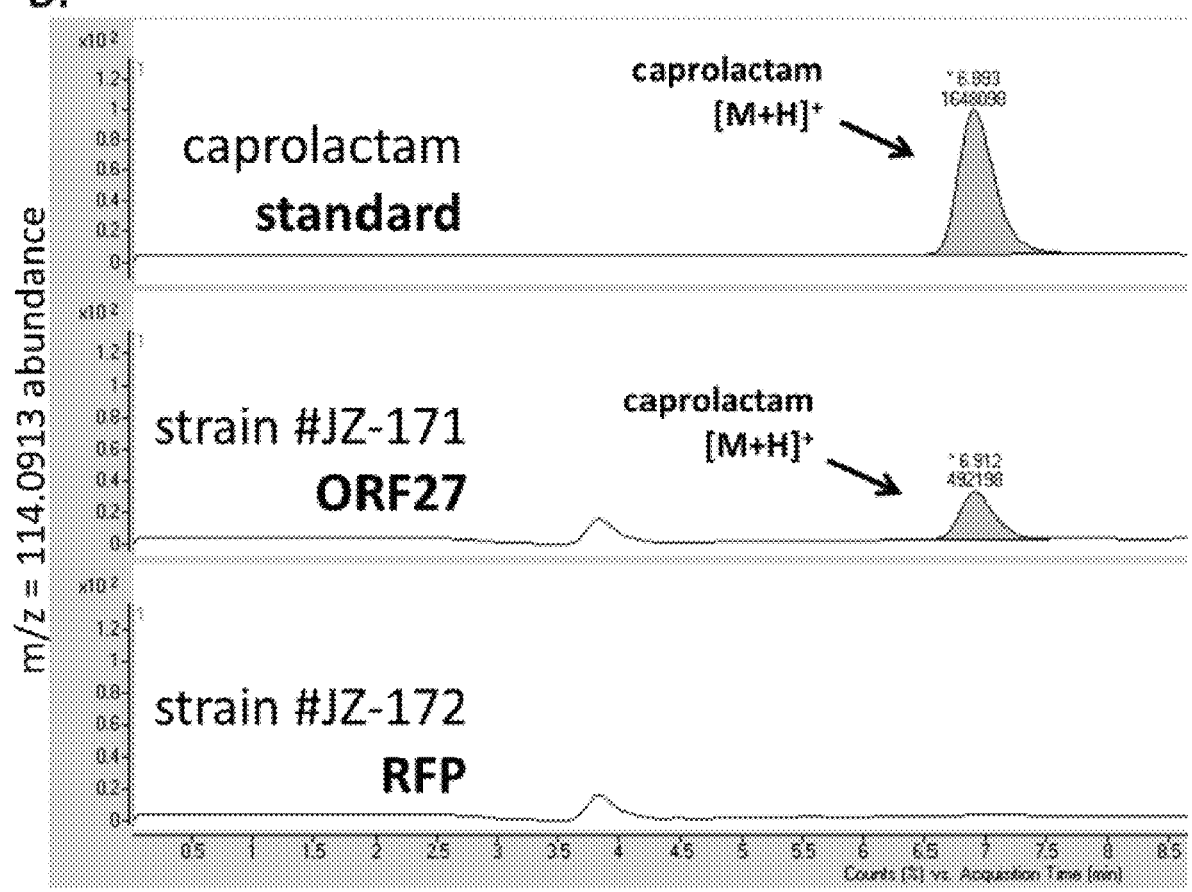
FIG. 9B. Production of industrial lactam via biosynthesis. LC-MS analysis of caprolactam production from recombinant E. coli expressing ORF27 with 1 mM 6-AHA feeding.

To demonstrate that valerolactam or caprolactam can be produced using whole-cell catalysts, we fed the respective precursors, 5-AVA or 6-AHA, to E. coli JZ-171, which overexpressed ORF27. Valerolactam (5-AVA fed) or caprolactam (6-AHA fed) was observed in the medium upon ORF27 expression (FIGS. 9A and 9B).

Figure 3A:
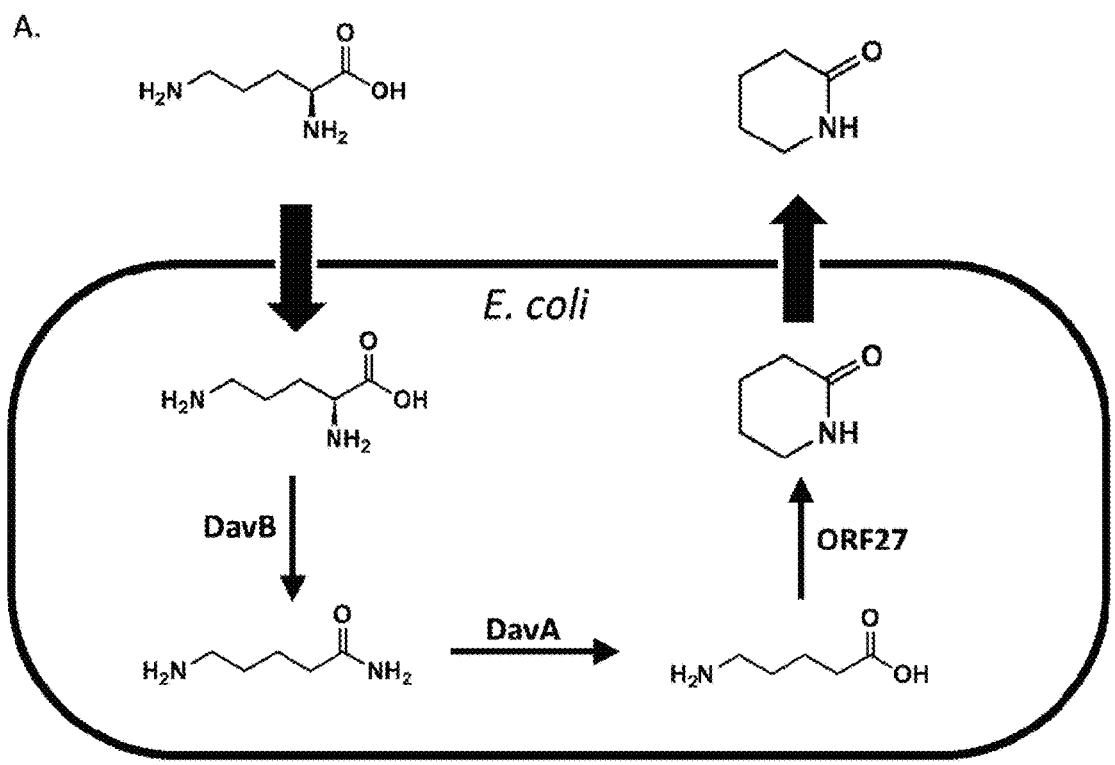
FIG. 3A. Valerolactam production in recombinant *E. coli*. Valerolactam biosynthesis pathway.
Figure 3B:
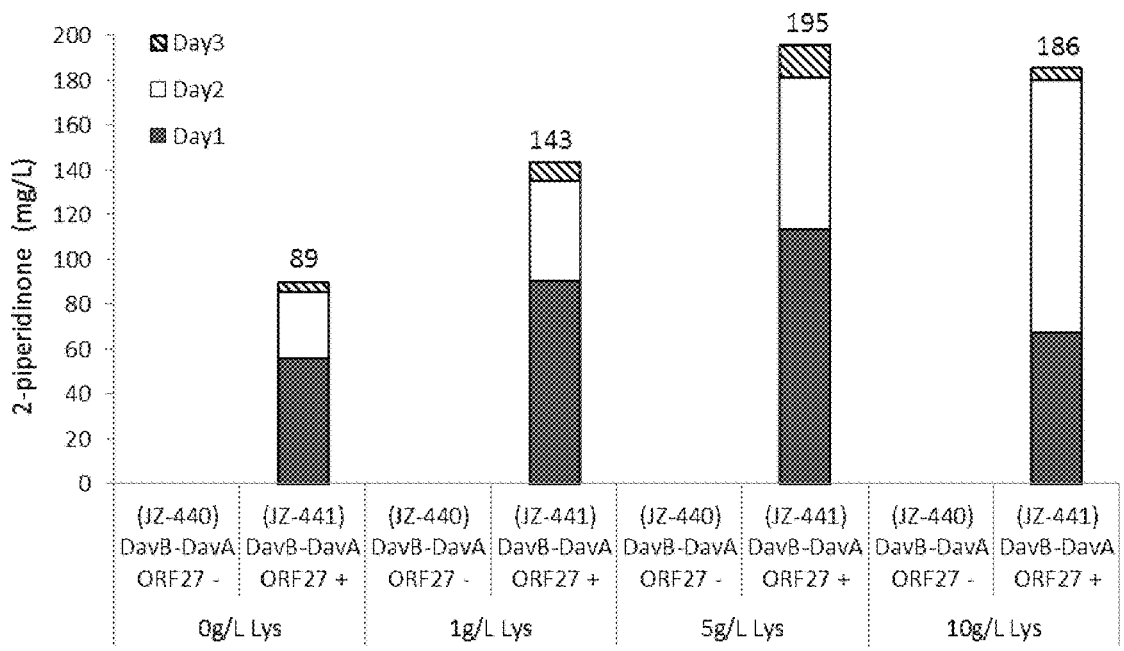
FIG. 3B, Valerolactam production in recombinant *E. coli*. Production of valerolactam via fermentation. Titer gain by day 1-3 after induction in strains JZ-440 (ORF27 negative control) and JZ-441 from 0 g/L, 1 g/L, 5 g/L and 10 g/L lysine feeding.

To demonstrate that valerolactam could be produced directly from glucose with no ω-amino fatty acid feeding, we introduced a pathway for 5-AVA biosynthesis into E. coli BL21(DE3)star, resulting in strain JZ-441(2-4). Valerolactam was produced directly from lysine when davA and davB were introduced into E. coli (FIG. 3A). Cells growing in medium supplemented with 5 g/L of lysine produced a maximum of 195 mg/L (2 mM) valerolactam. Increasing lysine supplementation to 10 g/L caused a reduction in bacterial growth and caused a delayed and decreased production of valerolactam. At 0 g/L lysine feeding, JZ-441 produced 89 mg/L of valerolactam (FIG. 3B). JZ-440, which lacks MBP-ORF27, produced no measurable valerolactam.

Discussion

Natural product biosynthesis continues to be a rich source of enzyme candidates with novel activities. ORF27, an enzyme in the *Streptomyces aizunensis* ECO-02301 biosynthetic cluster, was identified to be a 4-guanidinobutyryl-CoA synthetase, which has interesting implications for the ECO-02301 loading mechanism (12, 18, 19).

ORF27 accepted a wide range of short chain fatty acid substrates and their functionalized analogs. Both linear and branched fatty acid substrates were accepted as substrates. However, the enzyme seems to have little tolerance of polar groups at C3 position. Positively charged substrates, such as the ω-amino fatty acids or the ω-guanidino fatty acids are well tolerated, despite the fact that some substrates such as 6-guanidinohexanoic acid have two more carbons in their backbone than the native substrate. However, enzyme activity on substrates that have a negatively charged group on the ω-terminal end, such as a carboxylic acid group, was not observed, even though glutaric acid and adipic acid have similar steric hindrance as 6-guanidinohexanoic acid. This suggests that ORF27 has strict substrate selection residues around it binding pocket and preferentially favors substrates with a positively charged group on the w-terminal end.

The ability of ORF27 to accept various ω-amino fatty acids was explored for lactam biosynthesis. For lactam formation, ORF27 does not require CoASH as substrate and utilizes multiple reaction pathways. The activation of ω-amino fatty acids by ATP facilitates cyclization. This enables five-membered, six-membered and even seven-membered ring formation at mild temperatures, resulting in the production of important industrial lactams such as valerolactam and caprolactam via fermentation. Unlike the reversible aminolysis enzyme CALB that was previously described, ORF27 performs the reaction under milder condition in an irreversible fashion. The lactam product observed is exclusively cyclized monomers, without dimer or trimer contaminants. These novel features make ORF27 an ideal candidate for lactam biosynthesis. However, the enzyme catalyzed significant ATP and ADP hydrolysis during the reaction. Directed evolution of ORF27 towards less futile ATP and ADP hydrolysis could potentially improve ORF27 as a lactam synthase.

By introducing davB and davA into E. coli, we demonstrated valerolactam biosynthesis from lysine. Valerolactam production in autoinduction medium was lysine dependent. At concentrations of lysine below 5 g/L, valerolactam production correlated with lysine concentration. However, high concentrations of lysine (e.g., 10 g/L) inhibited bacterial growth and resulted in decreased valerolactam production. Even without lysine feeding, direct lysine production from glucose was sufficient to produce 50% of the valerolactam produced when 5 g/L lysine was fed to the culture. Interestingly, in the absence of ORF27, a slight amount of valerolactam was observed. Since 5-AVA does not cyclize when incubated in medium at 25° C., the observed valerolactam could result from catalysis by innate E. coli enzymes.

Caprolactam was also biosynthesized by feeding its precursor 6-aminohexanoic acid. With the recent publication of 6-aminohexanoic acid biosynthetic pathway in E. coli, ORF27 holds the promise to enable full caprolactam biosynthesis in a microbial host (7). This opens the door to substitute the current petrochemical process with a renewable bioprocess for a bulk chemical with four million ton annual production, potentially could make huge positive impact on our environment.

CONCLUSION

ORF27 is an enzyme in the ECO-02301 biosynthetic cluster. It was identified to catalyze 4-guanidinobutyryl-CoA formation, and was able to activate a wide range of substrates. While acting on ω-amino fatty acids, ORF27 can catalyze the ring closing reaction to produce lactams. Biosynthesis of polymer precursors such as caprolactam, valerolactam and butyrolactam were demonstrated from their respective ω-amino fatty acids. For in vivo production of valerolactam from lysine or glucose, the lysine to 5-AVA pathway was introduced into an E. coli strain harboring the gene encoding ORF27.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A genetically modified host cell comprising a 2-pyrrolidone synthase heterologous to the host cell, or thereof linked to a saccharide binding protein, wherein the 2-pyrrolidone synthase catalyzes the following reaction:

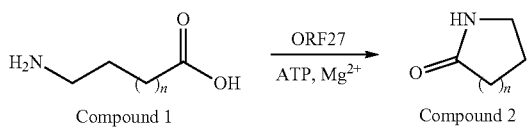

Compound 1           Compound 2 or reaction (2):

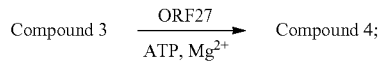

wherein Compound 3 is a "Substrate" and Compound 4 is a "Product" as indicated in Table 2 herein; wherein the genetically modified host cell is a yeast or prokaryotic cell, and comprises 5-aminovaleric acid (5-AVA), 6-aminohexanoic acid (6-AHA), 4-quanidinobutyric acid, valeric acid, 4-methyl-hexanoic acid, 6-aminocaproic acid, 6-quanidinohexanoic acid, or 2-aminobutyric acid.

2. The genetically modified host cell of claim 1, wherein the 2-pyrrolidone synthase comprises an amino acid sequence having at least 70% identity with SEQ ID NO:1, wherein the amino acid sequence comprises one or more of the following conserved amino acid motifs or sites: acyl-activating enzyme (AAE) consensus motif (residues 137, 140-145, and 147-148), acyl-activating enzyme (AAE) consensus motif (residues 140, 257-258, 279-284, 357, 369, 372, 382, and 458), AMP binding site (residues 140, 180-181, 227, 229-230, 233, 257-258, 279-284, 357, 369, 372, 379-382, and 439), and CoA binding site (residues 180, 229-230, 233, 257, 379-381, 433, and 439).

3. The genetically modified host cell of claim 2, wherein host cell is capable of synthesizing Compound 1 or uptaking Compound 1 from the environment or culture.

4. The genetically modified host cell of claim 3, wherein host cell further comprises one or more enzymes of a pathway for synthesizing Compound 1 from a carbon source.

5. The genetically modified host cell of claim 4, wherein pathway for synthesizing Compound 1 from a carbon source that is native to the host cell.

6. The genetically modified host cell of claim 4, wherein pathway for synthesizing Compound 1 from a carbon source that is heterologous to the host cell.

7. The genetically modified host cell of claim 1, wherein host cell lacks betaine-CoA ligase.

8. The genetically modified host cell of claim 2, wherein n is an integer from 1 to 20.

9. The genetically modified host cell of claim 8, wherein n is an integer from 1 to 10.

10. The genetically modified host cell of claim 9, wherein n is an integer from 1 to 7.

11. The genetically modified host cell of claim 10, wherein n is an integer from 1 to 3.

12. A method of producing a Compound 2 in a genetically modified host cell, comprising: (a) providing the genetically modified host cell of claim 1, (b) culturing the genetically modified host cell in a medium under a suitable condition such that the culturing results in the genetically modified host cell producing a Compound 2.

13. The method of claim 12, further comprising introducing one or more nucleic acid(s) into the host cell encoding the enzyme operably linked to a suitable promoter capable of transcription in the host cell, and optionally encoding the one or more enzyme(s) of a pathway for synthesizing Compound 1 from a carbon source, wherein the introducing step is prior to the culturing step.

14. The method of claim 12, further comprising separating Compound 2 from the host cell and/or the medium, wherein the separating step is subsequent, concurrent or partially concurrent with the culturing step.

15. The genetically modified host cell of claim 1, wherein the genetically modified host cell comprises 5-aminovaleric acid (5-AVA) or 6-aminohexanoic acid (6-AHA).

16. The genetically modified host cell of claim 1, wherein the genetically modified host cell is a *Yarrowia, Candida, Bebaromyces, Saccharomyces, Schizosaccharomyces* or *Pichia* cell.

17. The genetically modified host cell of claim 1, wherein the genetically modified host cell is a *Escherichia, Bacillus, Salmonella, Klebsiella, Enterobacter, Pseudomonas, Streptomyces, Cynechocystis, Cynechococcus, Sinorhizobium*, and *Caulobacter* cell.

* * * * *